United States Patent
Seo et al.

(10) Patent No.: US 9,391,289 B2
(45) Date of Patent: Jul. 12, 2016

(54) LIGHT-EMITTING DEVICE, ELECTRONIC DEVICE AND LIGHT DEVICE EACH COMPRISING LIGHT-EMITTING LAYER WITH MIXED ORGANIC COMPOUNDS CAPABLE OF FORMING AN EXCIPLEX

(71) Applicant: Semiconductor Energy Laboratory Co., Ltd., Atsugi-shi, Kanagawa-ken (JP)

(72) Inventors: Hiromi Seo, Sagamihara (JP); Satoko Shitagaki, Isehara (JP); Satoshi Seo, Sagamihara (JP); Takahiro Ushikubo, Ashikaga (JP); Toshiki Sasaki, Atsugi (JP); Shogo Uesaka, Atsugi (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 176 days.

(21) Appl. No.: 13/795,712

(22) Filed: Mar. 12, 2013

(65) Prior Publication Data

US 2014/0061604 A1  Mar. 6, 2014

(30) Foreign Application Priority Data

Apr. 6, 2012 (JP) ................. 2012-087050

(51) Int. Cl.
*H01L 51/50* (2006.01)
*C09K 11/06* (2006.01)
(Continued)

(52) U.S. Cl.
CPC ............ *H01L 51/5016* (2013.01); *C09K 11/06* (2013.01); *H01L 51/504* (2013.01);
(Continued)

(58) Field of Classification Search
None
See application file for complete search history.

(56) References Cited

U.S. PATENT DOCUMENTS 5,409,783 A  4/1995  Tang et al.
5,420,288 A  5/1995  Ohta et al.
(Continued)

FOREIGN PATENT DOCUMENTS

CN  001447629 A  10/2003
CN  1550540  12/2004
(Continued)

OTHER PUBLICATIONS

Baldo.M et al., "Very High-Efficiency Green Organic Light-Emitting Devices Based on Electrophosphorescence," Appl. Phys. Lett. (Applied Physics Letters), Jul. 5, 1999, vol. 75, No. 1, pp. 4-6.
(Continued)

*Primary Examiner* — Michael Jung
(74) *Attorney, Agent, or Firm* — Eric J. Robinson; Robinson Intellectual Property Law Office, P.C.

(57) ABSTRACT

A light-emitting element having high external quantum efficiency is provided. A light-emitting element having a long lifetime is provided. A light-emitting layer is provided between a pair of electrodes. The light-emitting layer is a stack of a first light-emitting layer, which contains at least a first phosphorescent compound, a first organic compound having an electron-transport property, and a second organic compound having a hole-transport property and is provided on the anode side, and a second light-emitting layer, which contains at least a second phosphorescent compound and the first organic compound having an electron-transport property. A combination of the first organic compound and the second organic compound forms an exciplex.

19 Claims, 27 Drawing Sheets

(51) Int. Cl.
- *H01L 51/52* (2006.01)
- *H01L 27/32* (2006.01)
- *H01L 51/00* (2006.01)

(52) U.S. Cl.
CPC ......... *H01L51/5028* (2013.01); *H01L 27/3206* (2013.01); *H01L 27/3209* (2013.01); *H01L 51/006* (2013.01); *H01L 51/0059* (2013.01); *H01L 51/0072* (2013.01); *H01L 51/0074* (2013.01); *H01L 51/0085* (2013.01); *H01L 51/5265* (2013.01)

(56) References Cited

U.S. PATENT DOCUMENTS

| | | |
|---|---|---|
| 5,597,890 A | 1/1997 | Jenekhe |
| 5,597,925 A | 1/1997 | Ohta et al. |
| 5,610,309 A | 3/1997 | Ohta et al. |
| 5,656,401 A | 8/1997 | Ohta et al. |
| 5,709,492 A | 1/1998 | Yasunaga et al. |
| 6,097,147 A | 8/2000 | Baldo et al. |
| 6,863,997 B2 | 3/2005 | Thompson et al. |
| 6,869,695 B2 | 3/2005 | Thompson et al. |
| 6,951,694 B2 | 10/2005 | Thompson et al. |
| 7,175,922 B2 | 2/2007 | Jarikov et al. |
| 7,183,010 B2 | 2/2007 | Jarikov |
| 7,553,557 B2 | 6/2009 | Thompson et al. |
| 7,572,522 B2 | 8/2009 | Seo et al. |
| 7,906,226 B2 | 3/2011 | Matsuura et al. |
| 7,943,925 B2 | 5/2011 | Yamazaki |
| 8,105,701 B2 | 1/2012 | Matsuura et al. |
| 8,247,086 B2 | 8/2012 | Inoue et al. |
| 8,853,680 B2 | 10/2014 | Yamazaki et al. |
| 9,269,920 B2 | 2/2016 | Yamazaki et al. |
| 2003/0189401 A1 | 10/2003 | Kido et al. |
| 2004/0076853 A1 | 4/2004 | Jarikov |
| 2004/0214040 A1 | 10/2004 | Lee et al. |
| 2005/0048310 A1 | 3/2005 | Cocchi et al. |
| 2005/0064237 A1 | 3/2005 | Kato et al. |
| 2005/0106415 A1 | 5/2005 | Jarikov et al. |
| 2005/0196775 A1 | 9/2005 | Swager et al. |
| 2006/0134464 A1 | 6/2006 | Nariyuki |
| 2006/0228577 A1 | 10/2006 | Nagara |
| 2007/0222374 A1 | 9/2007 | Egawa et al. |
| 2007/0244320 A1 | 10/2007 | Inoue et al. |
| 2007/0247829 A1 | 10/2007 | Fiedler et al. |
| 2008/0160345 A1 | 7/2008 | Inoue et al. |
| 2008/0217604 A1 | 9/2008 | Yokoyama et al. |
| 2008/0286604 A1 | 11/2008 | Inoue et al. |
| 2009/0153035 A1 | 6/2009 | Shin et al. |
| 2010/0052527 A1 | 3/2010 | Ikeda et al. |
| 2010/0145044 A1 | 6/2010 | Inoue et al. |
| 2010/0184942 A1 | 7/2010 | Chen et al. |
| 2011/0001146 A1 | 1/2011 | Yamazaki et al. |
| 2011/0210316 A1 | 9/2011 | Kadoma et al. |
| 2011/0215714 A1 | 9/2011 | Seo et al. |
| 2012/0061651 A1* | 3/2012 | Osaka et al. ............... 257/40 |
| 2012/0098417 A1 | 4/2012 | Inoue et al. |
| 2012/0132896 A1* | 5/2012 | Kawata et al. ............ 257/40 |
| 2012/0153267 A1 | 6/2012 | Matsuura et al. |
| 2012/0205632 A1 | 8/2012 | Shitagaki et al. |
| 2012/0205687 A1 | 8/2012 | Yamazaki et al. |
| 2012/0206035 A1 | 8/2012 | Shitagaki et al. |
| 2012/0217486 A1 | 8/2012 | Takemura et al. |
| 2012/0217487 A1 | 8/2012 | Yamazaki et al. |
| 2012/0242219 A1 | 9/2012 | Seo et al. |
| 2012/0248421 A1 | 10/2012 | Yamazaki et al. |
| 2012/0256535 A1 | 10/2012 | Seo et al. |
| 2012/0267618 A1 | 10/2012 | Monkman et al. |
| 2013/0048964 A1 | 2/2013 | Takeda et al. |
| 2013/0069077 A1* | 3/2013 | Song ................ H01L 51/5278 257/76 |
| 2013/0075782 A1 | 3/2013 | Ikeda et al. |
| 2013/0240851 A1 | 9/2013 | Seo et al. |
| 2013/0240859 A1* | 9/2013 | Arakane ................ C09K 11/06 257/40 |
| 2013/0270531 A1 | 10/2013 | Seo et al. |
| 2013/0292656 A1 | 11/2013 | Seo et al. |
| 2013/0292664 A1* | 11/2013 | Nishimura ............. C09B 57/00 257/40 |
| 2014/0014933 A1* | 1/2014 | Sasaki ................ H01L 51/5044 257/40 |
| 2014/0246663 A1* | 9/2014 | Kambe ............... H01L 51/5278 257/40 |
| 2014/0306207 A1* | 10/2014 | Nishimura ........... C07D 401/14 257/40 |

FOREIGN PATENT DOCUMENTS

| | | |
|---|---|---|
| CN | 102190653 | 9/2011 |
| CN | 102668149 | 9/2012 |
| CN | 103518268 A | 1/2014 |
| EP | 1351558 A | 10/2003 |
| EP | 1718122 A | 11/2006 |
| EP | 2363398 A | 9/2011 |
| EP | 2366753 A | 9/2011 |
| JP | 07-085972 A | 3/1995 |
| JP | 07-142169 A | 6/1995 |
| JP | 10-003990 A | 1/1998 |
| JP | 2003-272860 A | 9/2003 |
| JP | 2004-210785 A | 7/2004 |
| JP | 2006-203172 A | 8/2006 |
| JP | 2007-073620 A | 3/2007 |
| JP | 2009-108096 A | 5/2009 |
| JP | 2010-080435 A | 4/2010 |
| JP | 2010-135689 A | 6/2010 |
| JP | 2010-182699 | 8/2010 |
| JP | 2011-153269 A | 8/2011 |
| JP | 2011-201869 A | 10/2011 |
| JP | 2011-204673 A | 10/2011 |
| JP | 2011-216628 A | 10/2011 |
| JP | 2012-004526 A | 1/2012 |
| JP | 2012-238888 A | 12/2012 |
| JP | 2013-509670 A | 3/2013 |
| KR | 2004-0019177 A | 3/2004 |
| KR | 2004-0060527 A | 7/2004 |
| KR | 10-0624406 B | 9/2006 |
| KR | 2010-0027073 A | 3/2010 |
| KR | 2011-0099173 A | 9/2011 |
| KR | 2011-0099645 A | 9/2011 |
| KR | 2012-0103571 A | 9/2012 |
| TW | I271119 | 1/2007 |
| WO | WO-00/70655 | 11/2000 |
| WO | WO-2005/079118 | 8/2005 |
| WO | WO-2011/042443 | 4/2011 |
| WO | WO-2012/132809 | 10/2012 |

OTHER PUBLICATIONS

Choong.V et al., "Organic Light-Emitting Diodes With a Bipolar Transport Layer," Appl. Phys. Lett. (Applied Physics Letters), Jul. 12, 1999, vol. 75, No. 2, pp. 172-174.

Itano.K et al., "Exciplex formation at the organic solid-state interface: Yellow emission in organic light-emitting diodes using green-fluorescent tris(8-quinolinolato)aluminum and hole-transporting molecular materials with low ionization potentials," Appl. Phys. Lett. (Applied Physics Letters), Feb. 9, 1998, vol. 72, No. 6, pp. 636-638.

Kondakova.M et al., "High-efficiency, low-voltage phosphorescent organic light-emitting diode devices with mixed host," J. Appl. Phys. (Journal of Applied Physics), 2008, vol. 104, pp. 094501-1-094501-17.

Seo.J et al., "Efficient blue-green organic light-emitting diodes based on heteroleptic tris-cyclometalated iridium(III) complexes," Thin Solid Films, 2009, vol. 517, No. 5, pp. 1807-1810.

Hino.Y et al., "Red Phosphorescent Organic Light-Emitting Diodes Using Mixture System of Small-Molecule and Polymer Host,", Jpn. J. Appl. Phys. (Japanese Journal of Applies Physics), 2005, vol. 44, No. 4B, pp. 2790-2794.

International Search Report (Application No. PCT/JP2013/059429) Dated Jul. 2, 2013.

Written Opinion (Application No. PCT/JP2013/059429) Dated Jul. 2, 2013.

(56) References Cited

OTHER PUBLICATIONS

Adachi.C et al., "Nearly 100% Internal Phosphorescence Efficiency in an Organic Light Emitting Device", J. Appl. Phys. (Journal of Applied Physics), Nov. 15, 2001, vol. 90, No. 10, pp. 5048-5051.

Markham.J et al., "High-efficiency green phosphorescence from spin-coated single-layer dendrimer light-emitting diodes", Appl. Phys. Lett. (Applied Physics Letters), Apr. 15, 2002, vol. 80, No. 15, pp. 2645-2647.

Fujita.M et al., "Reduction of operating voltage in organic light-emitting diode by corrugated photonic crystal structure", Appl. Phys. Lett. (Applied Physics Letters), Dec. 6, 2004, vol. 85, No. 23, pp. 5769-5771

Baldo.M et al., "Prospects for Electrically Pumped Organic Lasers", Phys. Rev. B (Physical Review. B), Jul. 1, 2002, vol. 66, pp. 035321-1-035321-16.

Gu.G et al., "Transparent Organic Light Emitting Devices", Appl. Phys. Lett. (Applied Physics Letters), May 6, 1996, vol. 68, No. 19, pp. 2606-2608.

Baldo.M et al., "Highly Efficient Phosphorescent Emission From Organic Electroluminescent Devices", Nature, Sep. 10, 1998, vol. 395, pp. 151-154.

King.K et al., "Excited-state properties of a triply ortho-metalated iridium(III) complex", J. Am. Chem. Soc. (Journal of the American Chemical Society), Mar. 1, 1985, vol. 107, No. 5, pp. 1431-1432, ACS(American Chemical Society)

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Chinese Office Action (Application No. 201380018856.5) Dated Feb. 1, 2016.

* cited by examiner

- - Fluorescent spectrum of 1st or 2nd organic compound
- - - Phosphorescent spectrum of 1st or 2nd organic compound
—— Absorption spectrum of phosphorescent compound
—— Emission spectrum of exciplex

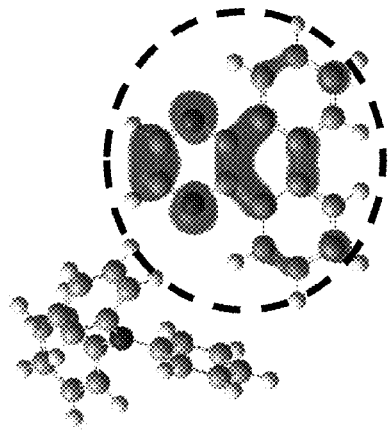
FIG. 3A1
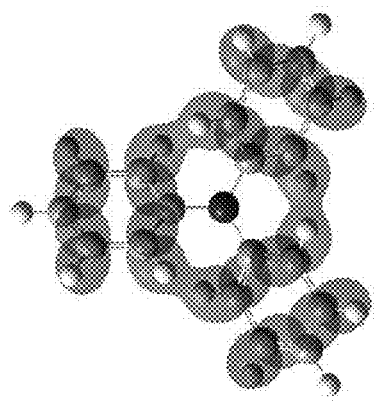
FIG. 3B1
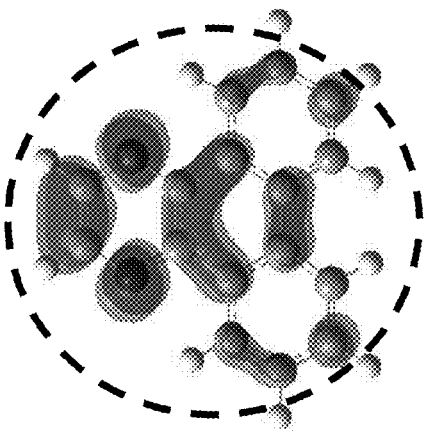
FIG. 3C1
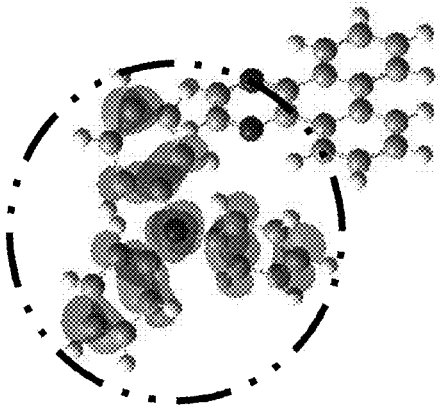
FIG. 3A2
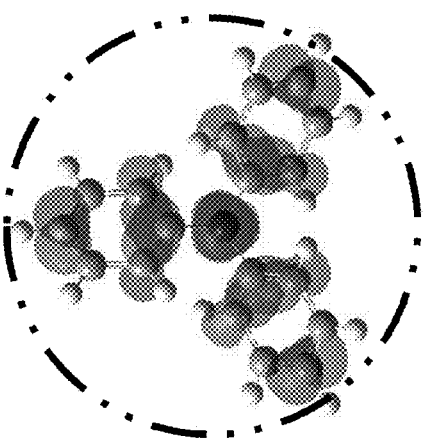
FIG. 3B2
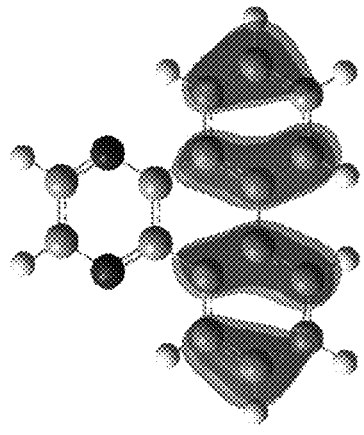
FIG. 3C2

LIGHT-EMITTING DEVICE, ELECTRONIC DEVICE AND LIGHT DEVICE EACH COMPRISING LIGHT-EMITTING LAYER WITH MIXED ORGANIC COMPOUNDS CAPABLE OF FORMING AN EXCIPLEX

TECHNICAL FIELD

One embodiment of the present invention relates to a light-emitting element in which an organic compound capable of providing light emission by application of an electric field is provided between a pair of electrodes, and also relates to a light-emitting device, an electronic device, and a lighting device including such a light-emitting element.

BACKGROUND ART

Light-emitting elements including an organic compound as a luminous body, which have features such as thinness, lightness, high-speed response, and DC driving at low voltage, are expected to be applied to next-generation flat panel displays. In particular, display devices in which light-emitting elements are arranged in a matrix are considered to have advantages of a wide viewing angle and high visibility over conventional liquid crystal display devices.

It is said that the light emission mechanism of a light-emitting element is as follows: when a voltage is applied between a pair of electrodes with an EL layer including a luminous body provided therebetween, electrons injected from the cathode and holes injected from the anode are recombined in the light emission center of the EL layer to form molecular excitons, and energy is released and light is emitted when the molecular excitons relax to the ground state. A singlet excited state and a triplet excited state are known as the excited states, and it is thought that light emission can be obtained through either of the excited states.

In order to improve element characteristics of such light-emitting elements, improvement of an element structure, development of a material, and the like have been actively carried out (see, for example, Patent Document 1).

REFERENCE

[Patent Document 1] Japanese Published Patent Application No. 2010-182699

DISCLOSURE OF INVENTION

However, it is said that the light extraction efficiency of a light-emitting element at present is approximately 20% to 30%. Even considering light absorption by a reflective electrode and a transparent electrode, the external quantum efficiency of a light-emitting element including a phosphorescent compound has a limit of approximately 25% at most.

In one embodiment of the present invention, a light-emitting element with high external quantum efficiency is provided. In another embodiment of the present invention, a light-emitting element having a long lifetime is provided.

One embodiment of the present invention is a light-emitting element including a light-emitting layer between a pair of electrodes (an anode and a cathode). The light-emitting layer has a stacked-layer structure including a first light-emitting layer, which contains at least a first phosphorescent compound (guest material), a first organic compound (host material) having an electron-transport property, and a second organic compound (assist material) having a hole-transport property and is provided on the anode side, and a second light-emitting layer, which contains at least a second phosphorescent compound (guest material) and the first organic compound (host material) having an electron-transport property. In the first light-emitting layer, a combination of the first organic compound and the second organic compound forms an exciplex.

Another embodiment of the present invention is a light-emitting element including a light-emitting layer between an anode and a cathode, a hole-transport layer between the anode and the light-emitting layer, and an electron-transport layer between the cathode and the light-emitting layer. The light-emitting layer is a stack of a first light-emitting layer, which contains at least a first phosphorescent compound, a first organic compound having an electron-transport property, and a second organic compound having a hole-transport property and is in contact with the hole-transport layer, and a second light-emitting layer, which contains at least a second phosphorescent compound and the first organic compound having an electron-transport property and is in contact with the electron-transport layer. A combination of the first organic compound and the second organic compound forms an exciplex.

Note that in each of the above embodiments, the emission wavelength of the exciplex formed by the first organic compound (host material) and the second organic compound (assist material) is located on the longer wavelength side with respect to the emission wavelength (fluorescent wavelength) of each of the first and second organic compounds (host and assist materials). Therefore, by formation of the exciplex, the fluorescent spectrum of the first organic compound (host material) and the fluorescent spectrum of the second organic compound (assist material) can be converted into an emission spectrum which is located on the longer wavelength side.

Accordingly, owing to the formation of the exciplex in the first light-emitting layer, the light-emitting element of one embodiment of the present invention can transfer energy by utilizing an overlap between the emission spectrum of the exciplex which is located on the longer wavelength side with respect to the emission wavelength (fluorescent wavelength) of each of the first and second organic compounds and the absorption spectrum of the first phosphorescent compound (guest material), and thus the light-emitting element can achieve high energy transfer efficiency and high external quantum efficiency. In the presence of the second organic compound (assist material) only in the first light-emitting layer, the hole-transport property in the second light-emitting layer can be lower than that in the first light-emitting layer, and a light-emitting region in the light-emitting layer owing to the exciplex can be controlled so as to be formed in the vicinity of the interface between the first light-emitting layer and the second light-emitting layer. Furthermore, when the exciplex is formed in the first light-emitting layer, holes which do not contribute to the formation of the exciplex can be made to contribute to light emission from the second phosphorescent compound (guest material) existing in the second light-emitting layer. Accordingly, the light-emitting element can have high emission efficiency and can be prevented from deteriorating due to a local increase in carrier density. In addition, since the second light-emitting layer has a low hole-transport property, a decrease in emission efficiency due to passage of holes to the cathode side can be reduced.

Note that in each of the above embodiments, the first phosphorescent compound (guest material) contained in the first light-emitting layer and the second phosphorescent compound (guest material) contained in the second light-emitting layer may be the same or different. Note that when different phosphorescent compounds are contained, light emitted from the first light-emitting layer owing to the first phosphorescent compound (guest material) has a shorter wavelength than light emitted from the second light-emitting layer owing to the second phosphorescent compound (guest material).

Note that in the first light-emitting layer of each of the above embodiments, the exciplex may be formed from an anion of the first organic compound and a cation of the second organic compound.

In each of the above embodiments, the phosphorescent compounds (the first phosphorescent compound and the second phosphorescent compound) may be organometallic complexes, the first organic compound may be mainly an electron-transport material having an electron mobility of $10^{-6}$ cm$^2$/Vs or more, specifically a π-electron deficient heteroaromatic compound, and the second organic compound may be mainly a hole-transport material having a hole mobility of $10^{-6}$ cm$^2$/Vs or more, specifically a π-electron rich heteroaromatic compound or an aromatic amine compound.

Further, the present invention includes, in its scope, electronic devices and lighting devices including light-emitting devices, as well as light-emitting devices including light-emitting elements. The light-emitting device in this specification refers to an image display device and a light source (e.g., a lighting device). In addition, the light-emitting device includes all the following modules: a module in which a connector, such as a flexible printed circuit (FPC) or a tape carrier package (TCP), is attached to a light-emitting device; a module in which a printed wiring board is provided at the end of a TCP; and a module in which an integrated circuit (IC) is directly mounted on a light-emitting device by a chip-on-glass (COG) method.

Note that, owing to the formation of the exciplex in the light-emitting layer, the light-emitting element of one embodiment of the present invention can transfer energy by utilizing an overlap between the emission spectrum of the exciplex which is located on the longer wavelength side with respect to the emission wavelength (fluorescent wavelength) of each of the first and second organic compounds and the absorption spectrum of the phosphorescent compound (guest material), and thus the light-emitting element can achieve high energy transfer efficiency and high external quantum efficiency.

Furthermore, the light-emitting layer in one embodiment of the present invention has a stacked-layer structure including the first light-emitting layer and the second light-emitting layer. The first light-emitting layer contains the first phosphorescent compound (guest material), the first organic compound (host material) having an electron-transport property, and the second organic compound (assist material) having a hole-transport property, and the second light-emitting layer contains the second phosphorescent compound (guest material) and the first organic compound (host material) having an electron-transport property. Therefore, the hole-transport property in the second light-emitting layer can be lower than that in the first light-emitting layer, and a light-emitting region in the light-emitting layer owing to the exciplex can be controlled so as to be formed in the vicinity of the interface between the first light-emitting layer and the second light-emitting layer. Furthermore, when the exciplex is formed in the first light-emitting layer, holes which do not contribute to the formation of the exciplex can be made to contribute to light emission from the second phosphorescent compound (guest material) existing in the second light-emitting layer. Accordingly, the light-emitting element can have high emission efficiency and can be prevented from deteriorating due to a local increase in carrier density. In addition, since the second light-emitting layer has a low hole-transport property, a decrease in emission efficiency due to passage of holes to the cathode side can be reduced.

BRIEF DESCRIPTION OF DRAWINGS

FIGS. 3A1, 3A2, 3B1, 3B2, 3C1, and 3C2 show calculation results according to one embodiment of the present invention.

BEST MODE FOR CARRYING OUT THE INVENTION

Figure 1A:
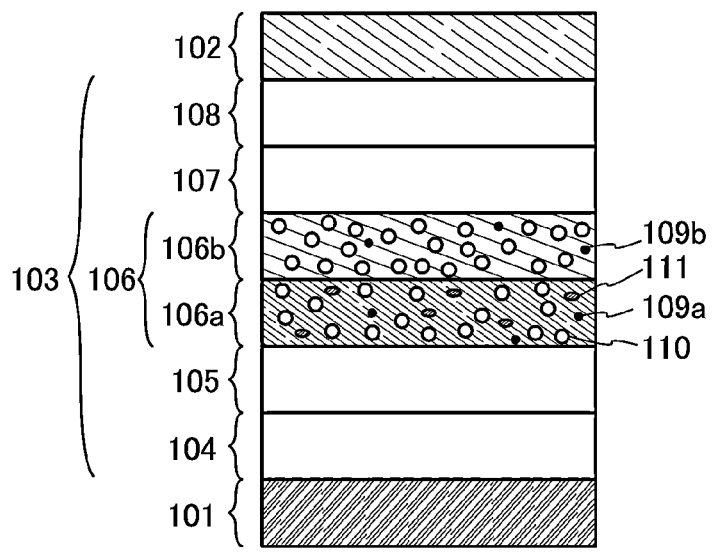
FIGS. 1A and 1B illustrate a concept of one embodiment of the present invention.

Embodiments of the present invention will be described below with reference to the drawings. Note that the present invention is not limited to the following description, and various changes and modifications can be made without departing from the spirit and scope of the invention. Therefore, the present invention should not be construed as being limited to the description in the following embodiments.

(Elementary Process of Light Emission in Light-emitting Element)

First, a description is given of general elementary processes of light emission in a light-emitting element using a phosphorescent compound as a guest material. Note that a molecule providing excitation energy is referred to as a host molecule, while a molecule receiving the excitation energy is referred to as a guest molecule.

(1) The case where an electron and a hole are recombined in a guest molecule, and the guest molecule is excited (direct recombination process).

(1-1) When the excited state of the guest molecule is a triplet excited state, the guest molecule emits phosphorescence.

(1-2) When the excited state of the guest molecule is a singlet excited state, the guest molecule in the singlet excited state undergoes intersystem crossing to a triplet excited state and emits phosphorescence.

In other words, in the direct recombination process in (1), as long as the efficiency of intersystem crossing and the phosphorescence quantum yield of the guest molecule are high, high emission efficiency can be obtained. Note that the $T_1$ level of the host molecule is preferably higher than the $T_1$ level of the guest molecule.

(2) The case where an electron and a hole are recombined in a host molecule and the host molecule is put in an excited state (energy transfer process).

(2-1) When the excited state of the host molecule is a triplet excited state and the $T_1$ level of the host molecule is higher than the $T_1$ level of the guest molecule, excitation energy is transferred from the host molecule to the guest molecule, and thus the guest molecule is put in a triplet excited state. The guest molecule in the triplet excited state emits phosphorescence. Note that energy transfer from the $T_1$ level of the host molecule to a singlet excitation energy level ($S_1$ level) of the guest molecule is forbidden unless the host molecule emits phosphorescence, and is unlikely to be a main energy transfer process; therefore, a description thereof is omitted here. In other words, energy transfer from the host molecule in the triplet excited state (3H*) to the guest molecule in the triplet excited state (3G*) is important as represented by Formula (2-1) below (where 1G represents the singlet ground state of the guest molecule and 1H represents the singlet ground state of the host molecule).

$$3H^* + 1G \rightarrow 1H + 3G^* \qquad (2\text{-}1)$$

(2-2) When the excited state of the host molecule is a singlet excited state and the $S_1$ level of the host molecule is higher than the $S_1$ level and $T_1$ level of the guest molecule, excitation energy is transferred from the host molecule to the guest molecule, and thus, the guest molecule is put in a singlet excited state or a triplet excited state. The guest molecule in the triplet excited state emits phosphorescence. In addition, the guest molecule in the singlet excited state undergoes intersystem crossing to a triplet excited state, and emits phosphorescence.

In other words, there can be a process where energy is transferred from the host molecule in the singlet excited state (1H*) to the guest molecule in the singlet excited state (1G*) and then the guest molecule is put in the triplet excited state (3G*) by intersystem crossing, as represented by Formula (2-2A) below, and a process where energy is directly transferred from the host molecule in the singlet excited state (1H*) to the guest molecule in the triplet excited state (3G*), as represented by Formula (2-2B) below.

$$1H^* + 1G \rightarrow 1H + 1G^* \rightarrow (\text{Intersystem crossing}) \rightarrow 1H + 3G^* \qquad (2\text{-}2A)$$

$$1H^* + 1G \rightarrow 1H + 3G^* \qquad (2\text{-}2B)$$

When all the energy transfer processes described above in (2) occur efficiently, both the triplet excitation energy and the singlet excitation energy of the host molecule are efficiently converted into the triplet excited state (3G*) of the guest molecule. Thus, high-efficiency light emission is possible. In contrast, before the excitation energy of the host molecule is transferred to the guest molecule, when the host molecule itself is deactivated by emitting the excitation energy as light or heat, the emission efficiency is decreased.

Next, factors controlling the above-described processes of intermolecular energy transfer between the host molecule and the guest molecule are described. As mechanisms of the intermolecular energy transfer, the following two mechanisms are proposed.

One mechanism is Förster mechanism (dipole-dipole interaction) in which energy transfer does not require direct contact between molecules and energy is transferred through a resonant phenomenon of dipolar oscillation between a host molecule and a guest molecule. By the resonant phenomenon of dipolar oscillation, the host molecule provides energy to the guest molecule, and thus, the host molecule is put in a ground state and the guest molecule is put in an excited state. Note that the rate constant $k_{h^* \rightarrow g}$ of Förster mechanism is expressed by Formula (1).

[Formula 1]

$$k_{h^* \rightarrow g} = \frac{9000 \, c^4 K^2 \phi \ln 10}{128 \, \pi^5 n^4 N \tau R^6} \int \frac{f'_h(v) \varepsilon_g(v)}{v^4} dv \qquad (1)$$

In Formula (1), v denotes a frequency, $f'_h(v)$ denotes a normalized emission spectrum of a host molecule (a fluorescent spectrum in energy transfer from a singlet excited state, and a phosphorescent spectrum in energy transfer from a triplet excited state), $\varepsilon_g(v)$ denotes a molar absorption coefficient of a guest molecule, N denotes Avogadro's number, n denotes a refractive index of a medium, R denotes an intermolecular distance between the host molecule and the guest molecule, $\tau$ denotes a measured lifetime of an excited state (fluorescence lifetime or phosphorescence lifetime), c denotes the speed of light, $\phi$ denotes a luminescence quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the host molecule and the guest molecule. Note that $K^2 = 2/3$ in random orientation.

The other is Dexter mechanism (electron exchange interaction) in which a host molecule and a guest molecule are close to a contact effective range where their orbitals overlap, and the host molecule in an excited state and the guest molecule in a ground state exchange their electrons, which leads to energy transfer. Note that the rate constant $k_{h^* \to g}$ of Dexter mechanism is expressed by Formula (2).

[Formula 2]

$$k_{h^* \to g} = \left(\frac{2\pi}{h}\right) K'^2 \exp\left(-\frac{2R}{L}\right) \int f'_h(v) \varepsilon'_g(v) dv \quad (2)$$

In Formula (2), h denotes a Planck constant, K' denotes a constant having an energy dimension, v denotes a frequency, $f'_h(v)$ denotes a normalized emission spectrum of a host molecule (a fluorescent spectrum in energy transfer from a singlet excited state, and a phosphorescent spectrum in energy transfer from a triplet excited state), $\varepsilon'_g(v)$ denotes a normalized absorption spectrum of a guest molecule, L denotes an effective molecular radius, and R denotes an intermolecular distance between the host molecule and the guest molecule.

Here, the efficiency of energy transfer from the host molecule to the guest molecule (energy transfer efficiency $\Phi_{ET}$) is thought to be expressed by Formula (3). In the formula, $k_r$ denotes a rate constant of a light-emission process (fluorescence in energy transfer from a singlet excited state, and phosphorescence in energy transfer from a triplet excited state) of a host molecule, $k_n$ denotes a rate constant of a non-light-emission process (thermal deactivation or intersystem crossing) of a host molecule, and $\tau$ denotes a measured lifetime of an excited state of a host molecule.

[Formula 3]

$$\Phi_{ET} = \frac{k_{h^* \to g}}{k_r + k_n + k_{h^* \to g}} \quad (3)$$
$$= \frac{k_{h^* \to g}}{\left(\frac{1}{\tau}\right) + k_{h^* \to g}}$$

According to Formula (3), it is found that the energy transfer efficiency $\Phi_{ET}$ can be increased by increasing the rate constant $k_{h^* \to g}$ of energy transfer so that another competing rate constant $k_r + k_n$ ($=1/\tau$) becomes relatively small.

(Energy Transfer Efficiency in (2-1))

Here, the energy transfer process in (2-1) is considered first. Since Förster mechanism (Formula (1)) is forbidden in this case, only Dexter mechanism (Formula (2)) should be considered. According to Formula (2), in order to increase the rate constant $k_{h^* \to g}$, it is preferable that an emission spectrum of a host molecule (here, a phosphorescent spectrum because energy transfer from a triplet excited state is discussed) largely overlap with an absorption spectrum of a guest molecule (absorption corresponding to direct transition from a singlet ground state to a triplet excited state).

In one embodiment of the present invention, a phosphorescent compound is used as a guest material. In an absorption spectrum of the phosphorescent compound, absorption corresponding to direct transition from a singlet ground state to a triplet excited state is observed in some cases, which is an absorption band on the longest wavelength side. In particular, light-emitting iridium complexes have a broad absorption band at around 500 nm to 600 nm as the absorption band on the longest wavelength side (as a matter of fact, the broad absorption band can be on a shorter or longer wavelength side depending on emission wavelengths). This absorption band is mainly based on a triplet MLCT (metal to ligand charge transfer) transition. Note that it is considered that the absorption band also includes absorptions based on a triplet π-π* transition and a singlet MLCT transition, and that these absorptions overlap each other to form a broad absorption band on the longest wavelength side in the absorption spectrum. In other words, the difference between the lowest singlet excited state and the lowest triplet excited state is small, and absorptions based on these states overlap each other to form a broad absorption band on the longest wavelength side in the absorption spectrum. Therefore, when an organometallic complex (especially iridium complex) is used as the guest material, the broad absorption band on the longest wavelength side largely overlaps with the phosphorescent spectrum of the host material as described above, whereby the rate constant $k_{h^* \to g}$ can be increased and energy transfer efficiency can be increased.

Furthermore, a fluorescent compound is generally used as the host material; thus, phosphorescence lifetime ($\tau$) is a millisecond or longer which is extremely long (i.e., $k_r + k_n$ is low). This is because the transition from the triplet excited state to the ground state (singlet) is a forbidden transition. Formula (3) shows that this is favorable to energy transfer efficiency $\Phi_{ET}$.

The above description also suggests that energy transfer from the host material in the triplet excited state to the guest material in the triplet excited state, i.e., the process in Formula (2-1), is generally likely to occur as long as the phosphorescent spectrum of the host material overlaps with the absorption spectrum corresponding to the direct transition of the guest material from the singlet ground state to the triplet excitation state.

(Energy Transfer Efficiency in (2-2))

Next, the energy transfer process in (2-2) is considered. The process in Formula (2-2A) is affected by the efficiency of intersystem crossing of the guest material. Therefore, in order to maximize emission efficiency, the process in Formula (2-2B) is considered to be important. Since Dexter mechanism (Formula (2)) is forbidden in this case, only Förster mechanism (Formula (1)) should be considered.

When $\tau$ is eliminated from Formula (1) and Formula (3), it can be said that the energy transfer efficiency $\Phi_{ET}$ is higher when the quantum yield $\phi$ (here, a fluorescent quantum yield because energy transfer from a singlet excited state is discussed) is higher. However, in practice, a more important factor is that the emission spectrum of the host molecule (here, a fluorescent spectrum because energy transfer from a singlet excited state is discussed) largely overlaps with the absorption spectrum of the guest molecule (absorption corresponding to the direct transition from the singlet ground state to the triplet excited state) (note that it is preferable that the molar absorption coefficient of the guest molecule be also high). This means that the fluorescent spectrum of the host material overlaps with the absorption band of the phosphorescent compound used as the guest material which is on the longest wavelength side.

However, this has conventionally been very difficult to achieve. The reason is that, in order to enable both of the above-described processes (2-1) and (2-2) to occur efficiently, it is clear from the above discussion that the host material should be designed so as to have not only its phosphorescent spectrum but also its fluorescent spectrum overlapping with the absorption band of the guest material which is on the longest wavelength side. In other words, the host material should be designed so as to have its fluorescent spectrum in a position similar to that of the phosphorescent spectrum.

However, in general, the $S_1$ level differs greatly from the $T_1$ level ($S_1$ level>$T_1$ level); therefore, the fluorescence emission wavelength also differs greatly from the phosphorescence emission wavelength (fluorescence emission wavelength<phosphorescence emission wavelength). For example, 4,4'-di(N-carbazolyl)biphenyl (abbreviation: CBP), which is commonly used as a host material in a light-emitting element including a phosphorescent compound, has a phosphorescent spectrum at around 500 nm and has a fluorescent spectrum at around 400 nm, which are largely different by about 100 nm. This example also shows that it is extremely difficult to design a host material so as to have its fluorescent spectrum in a position similar to that of its phosphorescent spectrum. Therefore, it is very important to improve efficiency in energy transfer from the host material in the singlet excited state to the guest material.

Therefore, one embodiment of the present invention provides a useful technique which can overcome such a problem of the efficiency of the energy transfer from the host material in the singlet excited state to the guest material. Specific embodiments thereof will be described below.

(Embodiment 1)

In this embodiment, a structural concept of a light-emitting element in one embodiment of the present invention and a specific structure of the light-emitting element will be described. Note that the light-emitting element in one embodiment of the present invention is formed such that an EL layer including a light-emitting layer is provided between a pair of electrodes and the light-emitting layer has a stacked-layer structure including a first light-emitting layer, which contains at least a first phosphorescent compound (guest material), a first organic compound (host material) having an electron-transport property, and a second organic compound (assist material) having a hole-transport property, and a second light-emitting layer, which contains at least a second phosphorescent compound (guest material) and the first organic compound (host material) having an electron-transport property.

First, an element structure of a light-emitting element which is an example of the present invention is described with reference to FIG. 1A.

In the element structure illustrated in FIG. 1A, an EL layer 103 including a light-emitting layer 106 is provided between a pair of electrodes (an anode 101 and a cathode 102), and the EL layer 103 has a structure in which a hole-injection layer 104, a hole-transport layer 105, the light-emitting layer 106 (106a and 106b), an electron-transport layer 107, an electron-injection layer 108, and the like are sequentially stacked over the anode 101.

The light-emitting layer 106 in one embodiment of the present invention has a structure in which a first light-emitting layer 106a containing at least a first phosphorescent compound (guest material) 109a, a first organic compound (host material) 110 having an electron-transport property, and a second organic compound (assist material) 111 having a hole-transport property and a second light-emitting layer 106b containing at least a second phosphorescent compound (guest material) 109b and the first organic compound (host material) 110 having an electron-transport property are stacked as illustrated in FIG. 1A. An electron-transport material having an electron mobility of $10^{-6}$ cm$^2$/Vs or more is mainly used as the first organic compound 110, and a hole-transport material having a hole mobility of $10^{-6}$ cm$^2$/Vs or more is mainly used as the second organic compound 111. In this specification, the first organic compound 110 is referred to as a host material, and the second organic compound 111 is referred to as an assist material.

A feature is that a combination of the first organic compound (host material) 110 and the second organic compound (assist material) 111 in the first light-emitting layer 106a forms an exciplex (also referred to as an excited complex). In addition, the emission wavelength of the exciplex formed is located on the longer wavelength side with respect to the emission wavelength (fluorescent wavelength) of each of the first and second organic compounds (host and assist materials) 110 and 111. Therefore, the fluorescent spectrum of the first organic compound (host material) 110 and the fluorescent spectrum of the second organic compound (assist material) 111 can be converted into an emission spectrum which is located on the longer wavelength side.

Note that in the above structure, it is preferable that the level of a triplet excitation energy ($T_1$ level) of each of the first and second organic compounds (host and assist materials) 110 and 111 be higher than the $T_1$ level of the first phosphorescent compound (guest material) 109a. This is because, when the $T_1$ level of the first organic compound 110 (or the second organic compound 111) is lower than the $T_1$ level of the first phosphorescent compound (guest material) 109a, the triplet excitation energy of the first phosphorescent compound (guest material) 109a, which contributes to light emission, is quenched by the first organic compound 110 (or the second organic compound 111) and accordingly the emission efficiency is decreased.

In addition, in the first light-emitting layer 106a included in the light-emitting layer 106, either the first organic compound (host material) 110 or the second organic compound (assist material) 111 may be contained in a higher proportion, and the present invention includes both cases in its scope.

Note that, when the proportion of the second organic compound (assist material) 111 that is a hole-transport material in the light-emitting layer 106 (the first light-emitting layer 106a and the second light-emitting layer 106b) is too high in the above structure with respect to the formation of the exciplex, carriers (holes) are likely to pass through the light-emitting layer 106, which results in a decrease in recombination efficiency. However, when the structure in one embodiment of the present invention described with reference to FIG. 1A is employed, carriers (holes) having passed through the first light-emitting layer 106a can be made to contribute to the formation of the exciton in the second light-emitting layer 106b. As a result, the light-emitting element can have high emission efficiency and can be prevented from deteriorating due to a local increase in carrier density.

Figure 1B:
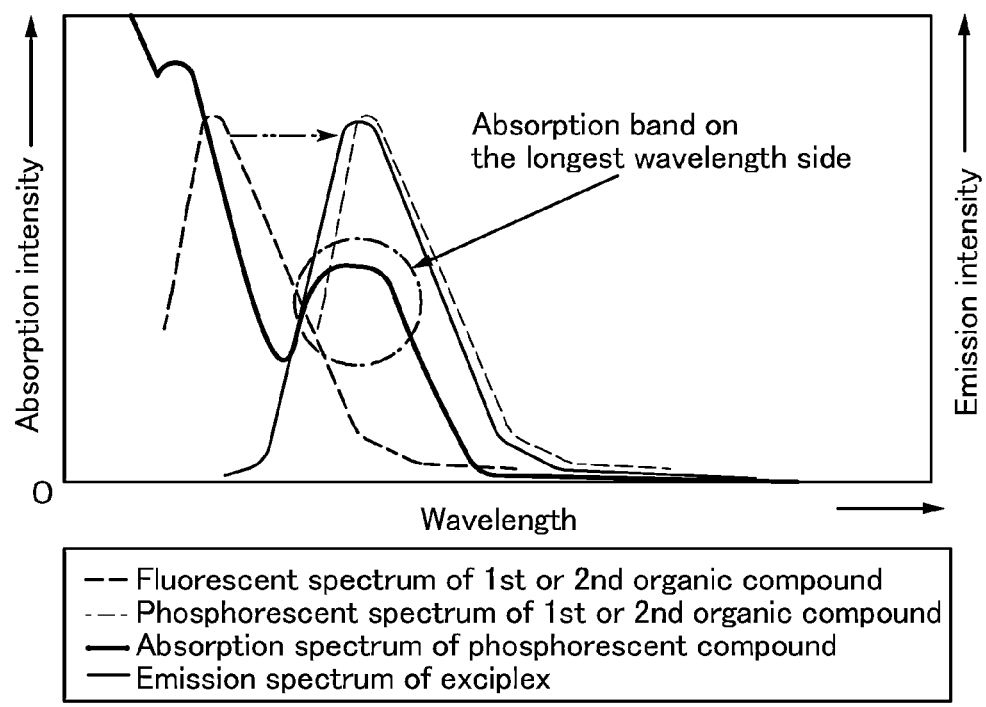

As described above, owing to the formation of the exciplex, the fluorescent spectrum of the first organic compound (host material) 110 and the fluorescent spectrum of the second organic compound (assist material) 111 can be converted into an emission spectrum which is located on the longer wavelength side. This means that, as illustrated in FIG. 1B, even when the fluorescent spectrum of the first organic compound 110 (or the second organic compound 111) is located on the shorter wavelength side with respect to the absorption band of the first phosphorescent compound (guest material) 109a which is located on the longest wavelength side, and does not have an overlap with the absorption band of the first phosphorescent compound (guest material) 109a which is located on the longest wavelength side, the emission spectrum of the exciplex and the absorption band can have a large overlap. Accordingly, the energy transfer efficiency in Formula (2-2B) above can be increased.

Furthermore, the exciplex is considered to have an extremely small difference between singlet excited energy and triplet excited energy. In other words, the emission spectrum of the exciplex from the single state and the emission spectrum thereof from the triplet state are highly close to each other. Accordingly, in the case where a design is implemented such that the emission spectrum of the exciplex (generally the emission spectrum of the exciplex from the singlet state) overlaps with the absorption band of the first phosphorescent compound (guest material) which is located on the longest wavelength side as described above, the emission spectrum of the exciplex from the triplet state (which is not observed at room temperature and not observed even at low temperature in many cases) also overlaps with the absorption band of the first phosphorescent compound (guest material) which is located on the longest wavelength side. In other words, not only the efficiency of the energy transfer from the singlet excited state ((2-2)) but also the efficiency of the energy transfer from the triplet excited state ((2-1)) can be increased, and as a result, energy from both the singlet and triplet excited states can be efficiently converted into light emission.

Thus, molecular orbital calculations were performed as described below to verify whether or not an exciplex actually has such characteristics. In general, a combination of a heteroaromatic compound and an aromatic amine often forms an exciplex under the influence of the lowest unoccupied molecular orbital (LUMO) level of the heteroaromatic compound which is deeper than the LUMO level of the aromatic amine (the property of easily accepting electrons) and the highest occupied molecular orbital (HOMO) level of the aromatic amine which is shallower than the HOMO level of the heteroaromatic compound (the property of easily accepting holes). Thus, calculations were performed using a combination of dibenzo[f,h]quinoxaline (abbreviation: DBq), which is a typical skeleton forming the LUMO of a heteroaromatic compound and is a model of the first organic compound 110 in one embodiment of the present invention, and triphenylamine (abbreviation: TPA), which is a typical skeleton forming the HOMO of an aromatic amine and is a model of the second organic compound 111 in one embodiment of the present invention.

First, the optimal molecular structures and the excitation energies of one molecule of DBq (abbreviation) and one molecule of TPA (abbreviation) in the lowest singlet excited state ($S_1$) and the lowest triplet excited state ($T_1$) were calculated using the time-dependent density functional theory (TD-DFT). Furthermore, the excitation energy of a dimer of DBq (abbreviation) and TPA (abbreviation) was also calculated.

In the DFT (density functional theory), the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable high-speed and high-accuracy calculations. Here, B3LYP which was a hybrid functional was used to specify the weight of each parameter related to exchange-correlation energy.

In addition, as a basis function, 6-311 (a basis function of a triple-split valence basis set using three contraction functions for each valence orbital) was applied to all the atoms.

By the above basis function, for example, 1s to 3s orbitals are considered in the case of hydrogen atoms, while 1s to 4s and 2p to 4p orbitals are considered in the case of carbon atoms. Furthermore, to improve calculation accuracy, the p function and the d function as polarization basis sets were added to hydrogen atoms and atoms other than hydrogen atoms, respectively.

Note that Gaussian 09 was used as a quantum chemistry computational program. A high performance computer (Altix 4700, manufactured by SGI Japan, Ltd.) was used for the calculations.

Figure 2:
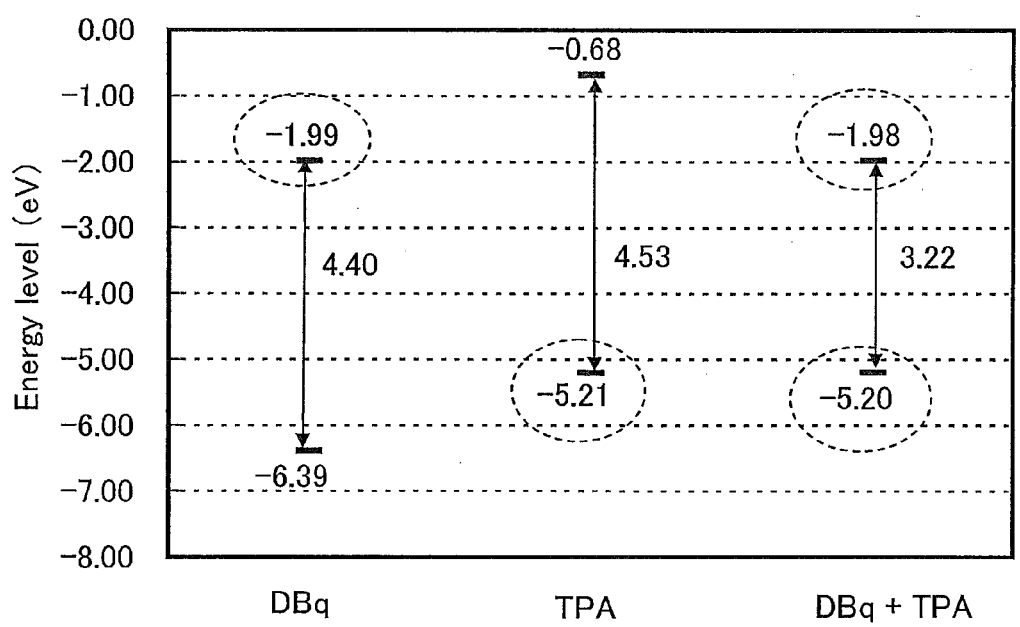
FIG. 2 shows calculation results according to one embodiment of the present invention.

First, the HOMO levels and the LUMO levels of one molecule of DBq (abbreviation), one molecule of TPA (abbreviation), and a dimer of DBq (abbreviation) and TPA (abbreviation) were calculated. FIG. 2 shows the HOMO levels and the LUMO levels, and FIGS. 3A1, 3A2, 3B1, 3B2, 3C1, and 3C2 show HOMO and LUMO distributions.

FIG. 3A1 shows the LUMO distribution of one molecule of DBq (abbreviation); FIG. 3A2, the HOMO distribution of one molecule of DBq (abbreviation); FIG. 3B1, the LUMO distribution of one molecule of TPA (abbreviation); FIG. 3B2, the HOMO distribution of one molecule of TPA (abbreviation); FIG. 3C1, the LUMO distribution of the dimer of DBq (abbreviation) and TPA (abbreviation); and FIG. 3C2, the HOMO distribution of the dimer of DBq (abbreviation) and TPA (abbreviation).

As shown in FIG. 2, it is suggested that the dimer of DBq (abbreviation) and TPA (abbreviation) forms an exciplex of DBq (abbreviation) and TPA (abbreviation) under the influence of the LUMO level (−1.99 eV) of DBq (abbreviation) which is deeper (lower) than the LUMO level of TPA (abbreviation) and the HOMO level (−5.21 eV) of TPA (abbreviation) which is shallower (higher) than the HOMO level of DBq (abbreviation). In fact, as is clear from FIGS. 3C1 and 3C2, the LUMO of the dimer of DBq (abbreviation) and TPA (abbreviation) is distributed on the DBq (abbreviation) side, and the HOMO thereof is distributed on the TPA (abbreviation) side.

Next, excitation energies obtained from the optimal molecular structures of one molecule of DBq (abbreviation) at $S_1$ and $T_1$ levels will be shown. Here, the excitation energies at the $S_1$ and $T_1$ levels correspond to fluorescence and phosphorescence wavelengths, respectively, obtained from one molecule of DBq (abbreviation). The excitation energy at the $S_1$ level of one molecule of DBq (abbreviation) is 3.294 eV, and the fluorescence wavelength is 376.4 nm. The excitation energy at the $T_1$ level of one molecule of DBq (abbreviation) is 2.460 eV, and the phosphorescence wavelength is 504.1 nm.

In addition, excitation energies obtained from the optimal molecular structures of one molecule of TPA (abbreviation) at $S_1$ and $T_1$ levels will be shown. Here, the excitation energies at the $S_1$ and $T_1$ levels correspond to fluorescence and phosphorescence wavelengths, respectively, obtained from one molecule of TPA (abbreviation). The excitation energy at the $S_1$ level of one molecule of TPA (abbreviation) is 3.508 eV, and the fluorescence wavelength is 353.4 nm. The excitation energy at the $T_1$ level of one molecule of TPA (abbreviation) is 2.610 eV, and the phosphorescence wavelength is 474.7 nm.

Furthermore, excitation energies obtained from the optimal molecular structures of the dimer of DBq (abbreviation) and TPA (abbreviation) at $S_1$ and $T_1$ levels will be shown. The excitation energies at the $S_1$ and $T_1$ levels correspond to fluorescence and phosphorescence wavelengths, respectively, obtained from the dimer of DBq (abbreviation) and TPA (abbreviation). The excitation energy at the $S_1$ level of the dimer of DBq (abbreviation) and TPA (abbreviation) is 2.036 eV, and the fluorescence wavelength is 609.1 nm. The excitation energy at the $T_1$ level of the dimer of DBq (abbreviation) and TPA (abbreviation) is 2.030 eV, and the phosphorescence wavelength is 610.0 nm.

It is found from the above that each of the phosphorescence wavelengths of one molecule of DBq (abbreviation) and one molecule of TPA (abbreviation) is shifted to the longer wavelength side by about 100 nm. This result shows a tendency similar to that of CBP (abbreviation) (measured values) described above and supports the validity of the calculations.

On the other hand, it is found that the fluorescence wavelength of the dimer of DBq (abbreviation) and TPA (abbreviation) is located on the longer wavelength side with respect to the fluorescence wavelengths of one molecule of DBq (abbreviation) and one molecule of TPA (abbreviation). It is also found that the difference between the fluorescence wavelength and the phosphorescence wavelength of the dimer of DBq (abbreviation) and TPA (abbreviation) is only 0.9 nm and that these wavelengths are substantially the same.

These results indicate that the exciplex can integrate the singlet excitation energy and the triplet excitation energy into substantially the same energy. Therefore, it is indicated as described above that the exciplex can efficiently transfer energy to the phosphorescent compound from both the singlet state and the triplet state thereof.

In the above manner, the light-emitting element in one embodiment of the present invention transfers energy by utilizing an overlap between the emission spectrum of the exciplex formed in the light-emitting layer and the absorption spectrum of the first phosphorescent compound (guest material) and thus has high energy transfer efficiency. Therefore, the light-emitting element can achieve high external quantum efficiency.

In addition, the exciplex exists only in an excited state and thus has no ground state capable of absorbing energy. Therefore, a phenomenon in which the first phosphorescent compound (guest material) is deactivated by energy transfer from the first phosphorescent compound (guest material) in the singlet excited state and triplet excited state to the exciplex before light emission (i.e., emission efficiency is lowered) is not considered to occur in principle. This also contributes to improvement of external quantum efficiency.

Note that the above-described exciplex is formed by an interaction between dissimilar molecules in excited states. The exciplex is generally known to be easily formed between a material having a relatively deep LUMO level and a material having a relatively shallow HOMO level.

An emission wavelength of the exciplex depends on a difference in energy between the HOMO level and the LUMO level. As a general tendency, when the energy difference is large, the emission wavelength is short, and when the energy difference is small, the emission wavelength is long.

Therefore, the HOMO levels and LUMO levels of the first organic compound (host material) 110 and the second organic compound (assist material) 111 in this embodiment are different from each other. Specifically, the energy levels vary in the following order: the HOMO level of the first organic compound 110<the HOMO level of the second organic compound 111<the LUMO level of the first organic compound 110<the LUMO level of the second organic compound 111 (see FIG. 4).

Figure 4:
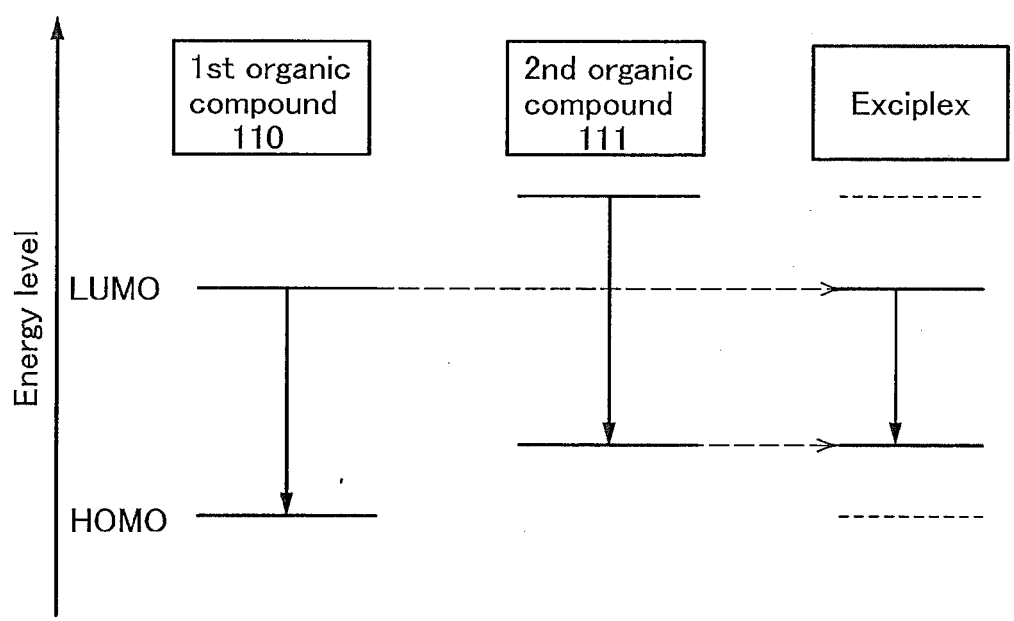
FIG. 4 illustrates energy levels of an exciplex applied to one embodiment of the present invention.

When the exciplex is formed by these two organic compounds, the LUMO level and the HOMO level of the exciplex originate from the first organic compound (host material) 110 and the second organic compound (assist material) 111, respectively (see FIG. 4). Therefore, the energy difference of the exciplex is smaller than the energy difference of the first organic compound (host material) 110 and the energy difference of the second organic compound (assist material) 111. In other words, the emission wavelength of the exciplex is longer than the emission wavelengths of the first organic compound (host material) 110 and the second organic compound (assist material) 111.

Note that the process of the exciplex formation in one embodiment of the present invention can be either of the following two processes.

One formation process is that an exciplex is formed from the first organic compound (host material) and the second organic compound (assist material) having carriers (cation or anion).

In general, when an electron and a hole are recombined in a host material, excitation energy is transferred from the host material in an excited state to a guest material, whereby the guest material is brought into an excited state to emit light. Before the excitation energy is transferred from the host material to the guest material, the host material itself emits light or the excitation energy turns into thermal energy, which leads to partial deactivation of the excitation energy. In particular, when the host material is in a singlet excited state, energy transfer is unlikely to occur as described in (2-2). Such deactivation of excitation energy is one of causes for a decrease in lifetime of a light-emitting element.

However, in one embodiment of the present invention, an exciplex is formed from the first organic compound (host material) and the second organic compound (assist material) having carriers (cation or anion); therefore, formation of a singlet exciton of the first organic compound (host material) can be suppressed. In other words, there can be a process where an exciplex is directly formed without formation of a singlet exciton. Thus, deactivation of the singlet excitation energy can be inhibited. Accordingly, a light-emitting element having a long lifetime can be obtained.

For example, in the case where the first organic compound 110 is an electron-trapping compound having the property of easily capturing electrons (carrier) (having a deep LUMO level) among electron-transport materials and the second organic compound 111 is a hole-trapping compound having the property of easily capturing holes (carrier) (having a shallow HOMO level) among hole-transport materials, an exciplex is formed directly from an anion of the first organic compound and a cation of the second organic compound. An exciplex formed through such a process is particularly referred to as an electroplex. A light-emitting element having high emission efficiency can be obtained by suppressing the generation of the singlet excited state of the first organic compound (host material) and transferring energy from an electroplex to the phosphorescent compound (guest material), in the above-described manner. Note that in this case, the generation of the triplet excited state of the first organic compound (host material) is similarly suppressed and an exciplex is directly formed; therefore, energy transfer is considered to occur from the exciplex to the first phosphorescent compound (guest material).

The other formation process is an elementary process where one of the first and second organic compounds (host and assist materials) forms a singlet exciton and then interacts with the other in the ground state to form an exciplex. Unlike an electroplex, a singlet excited state of the first organic compound (host material) or the second organic compound (assist material) is temporarily generated in this case, but this is rapidly converted into an exciplex, and thus, deactivation of singlet excitation energy can be inhibited. Thus, it is possible to inhibit deactivation of excitation energy of the first organic compound (host compound) or the second organic compound (assist material). Note that in this case, it is considered that the triplet excited state of the host material is similarly rapidly converted into an exciplex and energy is transferred from the exciplex to the phosphorescent compound (guest material).

Note that, in the case where the first organic compound (host material) is an electron-trapping compound, the second organic compound (assist material) is a hole-trapping compound, and the difference between the HOMO levels and the difference between the LUMO levels of these compounds are large (specifically, 0.3 eV or more), electrons are selectively injected into the first organic compound (host material) and holes are selectively injected into the second organic compound (assist material). In this case, it is thought that the process where an electroplex is formed takes precedence over the process where an exciplex is formed through a singlet exciton.

To make the emission spectrum of the exciplex and the absorption spectrum of the first phosphorescent compound (guest material) sufficiently overlap each other, the difference between the energy of a peak of the emission spectrum and the energy of a peak of the absorption band on the lowest energy side in the absorption spectrum is preferably 0.3 eV or less. The difference is more preferably 0.2 eV or less, even more preferably 0.1 eV or less.

In the light-emitting element in one embodiment of the present invention, it is also preferable that the excitation energy of the exciplex be sufficiently transferred to the first phosphorescent compound (guest material), and that light emission from the exciplex be not substantially observed. Therefore, energy is preferably transferred to the first phosphorescent compound (guest material) through the exciplex so that the first phosphorescent compound (guest material) emits phosphorescence. Note that the first phosphorescent compound (guest material) is preferably an organometallic complex.

In the case where a phosphorescent compound is used as the first organic compound (host material) in the first light-emitting layer 106a of the light-emitting element in one embodiment of the present invention, the first organic compound (host material) itself is likely to emit light and unlikely to allow energy to be transferred to the phosphorescent compound (guest material). In this case, it is favorable if the first organic compound could emit light efficiently, but it is difficult to achieve high emission efficiency because the first organic compound (host material) (note that the same applies to the second organic compound (assist material)) causes the problem of concentration quenching. For this reason, it is preferable that at least one of the first and second organic compounds (host and assist materials) be a fluorescent compound (i.e., a compound which is likely to undergo light emission or thermal deactivation from the singlet excited state) and an exciplex be used as a medium for energy transfer.

Note that the structure described in this embodiment can be combined as appropriate with any of the structures described in the other embodiments.

(Embodiment 2)

In this embodiment, an example of a light-emitting element in one embodiment of the present invention is described with reference to FIG. 5.

Figure 5:
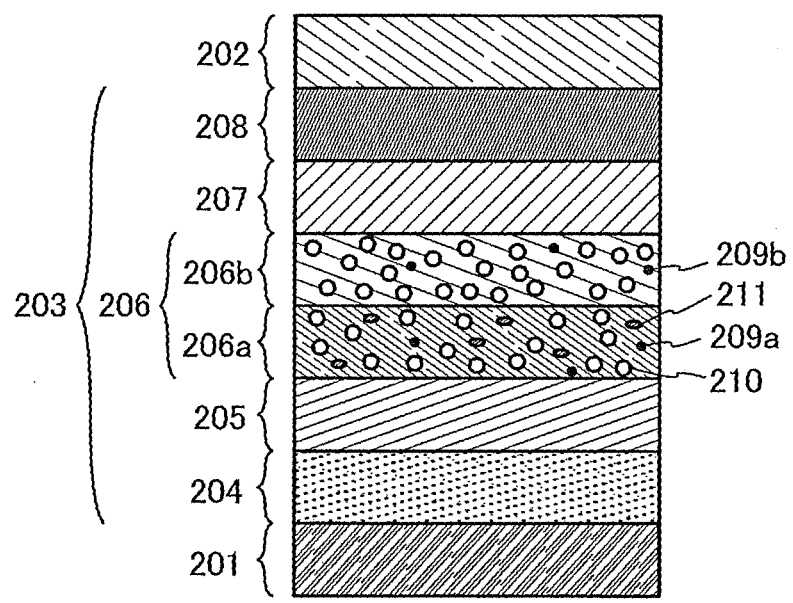
FIG. 5 illustrates a structure of a light-emitting element.

In the light-emitting element described in this embodiment, as illustrated in FIG. 5, an EL layer 203 including a light-emitting layer 206 is provided between a pair of electrodes (a first electrode (anode) 201 and a second electrode (cathode) 202), and the EL layer 203 includes a hole-injection layer 204, a hole-transport layer 205, an electron-transport layer 207, an electron-injection layer 208, and the like in addition to the light-emitting layer 206 having a stacked-layer structure including a first light-emitting layer 206a and a second light-emitting layer 206b.

Note that the light-emitting layer 206 described in this embodiment has a stacked-layer structure including the first light-emitting layer 206a and the second light-emitting layer 206b. In the light-emitting layer 206, the first light-emitting layer 206a contains a first phosphorescent compound (guest material) 209a, a first organic compound (host material) 210 having an electron-transport property, and a second organic compound (assist material) 211 having a hole-transport property, and the second light-emitting layer 206b contains a second phosphorescent compound (guest material) 209b and the first organic compound (host material) 210 having an electron-transport property.

When a structure in which the phosphorescent compounds (the first phosphorescent compound 209a and the second phosphorescent compound 209b) are dispersed in either the first organic compound (host material) 210 or the second organic compound (assist material) 211, or both, in the light-emitting layer 206 (the first light-emitting layer 206a and the second light-emitting layer 206b) is employed, crystallization of the light-emitting layer 206 can be suppressed. Further, it is possible to suppress concentration quenching due to high concentration of the phosphorescence compound, and thus the light-emitting element can have higher emission efficiency.

It is preferable that the level of a triplet excitation energy ($T_1$ level) of each of the first and second organic compounds 210 and 211 be higher than the $T_1$ level of the first phosphorescent compound 209a. This is because, when the $T_1$ level of the first organic compound 210 (or the second organic compound 211) is lower than the $T_1$ level of the first phosphorescent compound 209a, the triplet excitation energy of the first phosphorescent compound 209a, which contributes to light emission, is quenched by the first organic compound 210 (or the second organic compound 211) and accordingly the emission efficiency is decreased.

In the first light-emitting layer 206a of the light-emitting layer 206 in this embodiment, the first organic compound 210 and the second organic compound 211 form an exciplex at the time of recombination of carriers (electrons and holes) injected from the respective electrodes. Thus, a fluorescence spectrum of the first organic compound 210 and that of the second organic compound 211 in the first light-emitting layer 206a can be converted into an emission spectrum of the exciplex which is located on a longer wavelength side. Therefore, the first organic compound 210 and the second organic compound 211 are selected in such a manner that the emission spectrum of the exciplex largely overlaps with the absorption spectrum of the first phosphorescent compound 209a, in order to maximize energy transfer from a singlet excited state. It is assumed here that energy transfer from the exciplex, not the host material, occurs also in the case of a triplet excited state.

Note that the phosphorescent compounds (the first phosphorescent compound 209a and the second phosphorescent compound 209b) are preferably organometallic complexes. An electron-transport material is preferably used as the first organic compound (host material) 210. A hole-transport material is preferably used as the second organic compound (assist material) 211.

Note that examples of the organometallic complex include bis[2-(4',6'-difluorophenyl)pyridinato-N,$C^{2'}$]iridium(III)tetrakis(1-pyrazolyl)borate (abbreviation: FIr6), bis[2-(4',6'-difluorophenyl)pyridinato-N,$C^{2'}$]iridium(III)picolinate (abbreviation: FIrpic), bis[2-(3',5'-bistrifluoromethylphenyl)pyridinato-N,$C^{2'}$]iridium(III)picolinate (abbreviation:

Ir(CF₃ ppy)₂(pic)), bis[2-(4',6'-difluorophenyl)pyridinato-N, C²']iridium(III)acetylacetonate (abbreviation: FIracac), tris(2-phenylpyridinato)iridium(III) (abbreviation: Ir(ppy)₃), bis(2-phenylpyridinato)iridium(III)acetylacetonate (abbreviation: Ir(ppy)₂(acac)), bis(benzo[h]quinolinato)iridium(III)acetylacetonate (abbreviation: Ir(bzq)₂(acac)), bis(2,4-diphenyl-1,3-oxazolato-N,C²')iridium(III)acetylacetonate (abbreviation: Ir(dpo)₂(acac)), bis{2-[4'-(perfluorophenyl)phenyl]pyridinato-N,C²' }iridium(III) acetylacetonate (abbreviation: Ir(p-PF-ph)₂(acac)), bis(2-phenylbenzothiazolato-N,C²')iridium(III)acetylacetonate (abbreviation: Ir(bt)₂(acac)), bis[2-(2'-benzo[4,5-α]thienyl)pyridinato-N,C³']iridium(III)acetylacetonate (abbreviation: Ir(btp)₂(acac)), bis(1-phenylisoquinolinato-N, C²')iridium (III)acetylacetonate (abbreviation: Ir(piq)₂(acac)), (acetylacetonato)bis[2,3-bis(4-fluorophenyl)quinoxalinato]iridium (III) (abbreviation: Ir(Fdpq)₂(acac)), (acetylacetonato)bis(2,3,5-triphenylpyrazinato)iridium(III) (abbreviation: Ir(tppr)₂(acac)), 2,3,7,8,12,13,17,18-octaethyl-21H,23H-porphyrin platinum(II) (abbreviation: PtOEP), tris(acetylacetonato) (monophenanthroline)terbium(III) (abbreviation: Tb(acac)₃ (Phen)), tris(1,3-diphenyl-1,3-propanedionato) (monophenanthroline)europium(III) (abbreviation: Eu(DBM)₃(Phen)), tris[1-(2-thenoyl)-3,3,3-trifluoroacetonato](monophenanthroline)europium(III) (abbreviation: Eu(TTA)₃(Phen)), and the like.

As the electron-transport material, a π-electron deficient heteroaromatic compound such as a nitrogen-containing heteroaromatic compound is preferable, examples of which include quinoxaline derivatives and dibenzoquinoxaline derivatives such as 2-[3-(dibenzothiophen-4-yl)phenyl] dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl) phenyl]dibenzo[f,h]quinoxaline (abbreviation: 7mDBTPDBq-II), and 6-[3-(dibenzothiophen-4-yl)phenyl] dibenzo[f,h]quinoxaline (abbreviation: 6mDBTPDBq-II).

As the hole-transport material, a π-electron rich heteroaromatic compound (e.g., a carbazole derivative or an indole derivative) or an aromatic amine compound is preferable, examples of which include 4-phenyl-4'-(9-phenyl-9H-carbazol-3-yl)triphenylamine (abbreviation: PCBA1BP), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)-amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)-amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

Note that materials which can be used for the phosphorescent compound 209, the first organic compound (host material) 210, and the second organic compound (assist material) 211 are not limited to the above examples. The combination is determined so that an exciplex can be formed, the emission spectrum of the exciplex overlaps with the absorption spectrum of the first phosphorescent compound 209a, and the peak of the emission spectrum of the exciplex has a longer wavelength than the peak of the absorption spectrum of the first phosphorescent compound 209a.

In the case where an electron-transport material is used as the first organic compound 210 and a hole-transport material is used as the second organic compound 211, carrier balance can be controlled by the mixture ratio of the compounds. Specifically, the ratio of the first organic compound 210 to the second organic compound 211 is preferably 1:9 to 9:1.

Note that the phosphorescent compounds (the first phosphorescent compound 209a and the second phosphorescent compound 209b) may be replaced with a material exhibiting thermally activated delayed fluorescence, i.e., a thermally activated delayed fluorescence (TADF) material. Here, the term "delayed fluorescence" refers to light emission having a spectrum similar to normal fluorescence and an extremely long lifetime. The lifetime is $10^{-6}$ seconds or longer, preferably $10^{-3}$ seconds or longer. Specific examples of the thermally activated delayed fluorescence material include a fullerene, a derivative thereof, an acridine derivative such as proflavine, and eosin. Other examples include a metal-containing porphyrin, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCl₂(OEP)). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-α]carbazol-11-yl)-1,3,5-triazine (PIC-TRZ). Note that a material in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the energy difference between the $S_1$ level and the $T_1$ level becomes small.

A specific example in which the light-emitting element described in this embodiment is manufactured is described below.

For the first electrode (anode) 201 and the second electrode (cathode) 202, a metal, an alloy, an electrically conductive compound, a mixture thereof, or the like can be used. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), or titanium (Ti) can be used. In addition, an element belonging to Group 1 or Group 2 of the periodic table, for example, an alkali metal such as lithium (Li) or cesium (Cs), an alkaline earth metal such as magnesium (Mg), calcium (Ca), or strontium (Sr), an alloy containing such an element (e.g., MgAg or AlLi), a rare earth metal such as europium (Eu) or ytterbium (Yb), an alloy containing such an element, graphene, or the like can be used. The first electrode (anode) 201 and the second electrode (cathode) 202 can be formed by, for example, a sputtering method, an evaporation method (including a vacuum evaporation method), or the like.

Examples of a substance having a high hole-transport property which is used for the hole-injection layer 204 and the hole-transport layer 205 include aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1). Other examples include carbazole derivatives such as 4,4'-di(N-carbazolyl)biphenyl (abbreviation: CBP), 1,3,5-tris[4-(N-carbazolyl)-phenyl]benzene (abbreviation: TCPB), and 9-[4-(10-phenyl-9-anthracenyl)phenyl]-9H-carbazole (abbreviation: CzPA). The substances mentioned here are mainly substances that have a hole mobility of $10^{-6}$ cm$^2$/Vs or more. Note that other than these substances, any substance that has a property of transporting more holes than electrons may be used.

Still other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine] (abbreviation: Poly-TPD).

Further, examples of an acceptor substance which can be used for the hole-injection layer 204 include oxides of transition metals, oxides of metals belonging to Groups 4 to 8 of the periodic table, and the like. Specifically, molybdenum oxide is particularly preferable.

In the light-emitting layer 206 (206a and 206b), the first light-emitting layer 206a contains at least the phosphorescent compound 209, the first organic compound (host material) 210, and the second organic compound (assist material) 211, and the second light-emitting layer 206b contains at least the phosphorescence compound 209 and the first organic compound (host material) 210, as described above.

The electron-transport layer 207 is a layer that contains a substance having a high electron-transport property. For the electron-transport layer 207, it is possible to use a metal complex such as Alq$_3$, tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)benzothiazolato]zinc (abbreviation: Zn(BTZ)$_2$). Alternatively, it is possible to use a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs). Further alternatively, it is possible to use a high molecular compound such as poly(2,5-pyridine-diyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy). The substances mentioned here are mainly substances that have an electron mobility of $10^{-6}$ cm$^2$/Vs or more. Note that other than these substances, any substance that has a property of transporting more electrons than holes may be used for the electron-transport layer 207.

The electron-transport layer 207 is not limited to a single layer, and may be a stack of two or more layers containing any of the above substances.

The electron-injection layer 208 is a layer that contains a substance having a high electron-injection property. Examples of the substance that can be used for the electron-injection layer 208 include alkali metals, alkaline earth metals, and compounds thereof, such as lithium fluoride (LiF), cesium fluoride (CsF), calcium fluoride (CaF$_2$), and lithium oxide (LiO$_x$), and rare earth metal compounds, such as erbium fluoride (ErF$_3$). Alternatively, the above-mentioned substances for forming the electron-transport layer 207 can be used.

Alternatively, a composite material in which an organic compound and an electron donor (a donor) are mixed may be used for the electron-injection layer 208. Such a composite material, in which electrons are generated in the organic compound by the electron donor, has high electron-injection and electron-transport properties. The organic compound here is preferably a material excellent in transporting the generated electrons, and specifically any of the above substances (such as metal complexes and heteroaromatic compounds) for the electron-transport layer 207 can be used. As the electron donor, a substance showing an electron-donating property with respect to the organic compound may be used. Specifically, alkali metals, alkaline earth metals, and rare earth metals are preferable, and lithium, cesium, magnesium, calcium, erbium, ytterbium, and the like can be given. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 204, the hole-transport layer 205, the light-emitting layer 206 (206a and 206b), the electron-transport layer 207, and the electron-injection layer 208 which are mentioned above can each be formed by a method such as an evaporation method (including a vacuum evaporation method), an inkjet method, or a coating method.

Light emission obtained in the light-emitting layer 206 of the above-described light-emitting element is extracted to the outside through either the first electrode 201 or the second electrode 202 or both. Therefore, either the first electrode 201 or the second electrode 202 in this embodiment, or both, is an electrode having a light-transmitting property.

In the light-emitting element described in this embodiment, energy transfer efficiency can be improved owing to energy transfer utilizing an overlap between an emission spectrum of an exciplex and an absorption spectrum of a phosphorescent compound; accordingly, the light-emitting element can achieve high external quantum efficiency.

Note that the light-emitting element described in this embodiment is one embodiment of the present invention and is particularly characterized by the structure of the light-emitting layer. Therefore, when the structure described in this embodiment is employed, a passive matrix light-emitting device, an active matrix light-emitting device, and the like can be manufactured. Each of these light-emitting devices is included in the present invention.

Note that there is no particular limitation on the structure of a TFT in the case of manufacturing the active matrix light-emitting device. For example, a staggered TFT or an inverted staggered TFT can be used as appropriate. Further, a driver circuit formed over a TFT substrate may be formed using both an n-type TFT and a p-type TFT or either an n-type TFT or a p-type TFT. Furthermore, there is also no particular limitation on the crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 3)

In this embodiment, as one embodiment of the present invention, a light-emitting element (hereinafter referred to as tandem light-emitting element) in which a charge generation layer is provided between a plurality of EL layers will be described.

Figure 6A:
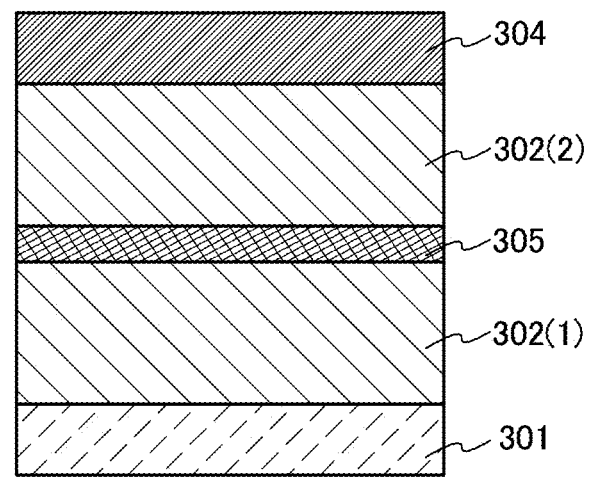
FIGS. 6A and 6B each illustrate a structure of a light-emitting element.

The light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 6A.

In this embodiment, the first electrode 301 functions as an anode, and the second electrode 304 functions as a cathode. Note that the first electrode 301 and the second electrode 304 can have structures similar to those described in Embodiment 1. In addition, all or any of the plurality of EL layers (the first EL layer 302(1) and the second EL layer 302(2)) may have structures similar to those described in Embodiment 1 or 2. In other words, the structures of the first EL layer 302(1) and the second EL layer 302(2) may be the same or different from each other and can be similar to those of the EL layers described in Embodiment 1 or 2.

Further, a charge generation layer (I) 305 is provided between the plurality of EL layers (the first EL layer 302(1) and the second EL layer 302(2)). The charge generation layer (I) 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer (I) 305 injects electrons into the first EL layer 302(1) and injects holes into the second EL layer 302(2).

Note that in terms of light extraction efficiency, the charge generation layer (I) 305 preferably has a light-transmitting property with respect to visible light (specifically, the charge generation layer (I) 305 preferably has a visible light transmittance of 40% or more). Further, the charge generation layer (I) 305 functions even if it has lower conductivity than the first electrode 301 or the second electrode 304.

The charge generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case where the electron acceptor is added to the organic compound having a high hole-transport property, examples of the organic compound having a high hole-transport property include aromatic amine compounds such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than these substances, any organic compound that has a property of transporting more holes than electrons may be used.

Examples of the electron acceptor include 7,7,8,8-tetracyano-2,3,5,6-tetrafluoroquinodimethane (abbreviation: F$_4$-TCNQ), chloranil, oxides of transition metals, and oxides of metals that belong to Groups 4 to 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting property. Among these, molybdenum oxide is especially preferable since it is stable in the air, has a low hygroscopic property, and is easy to handle.

On the other hand, in the case where the electron donor is added to the organic compound having a high electron-transport property, examples of the organic compound having a high electron-transport property which can be used are metal complexes having a quinoline skeleton or a benzoquinoline skeleton, such as Alq, Almq$_3$, BeBq$_2$, and BAlq, and the like. Other examples are metal complexes having an oxazole-based or thiazole-based ligand, such as Zn(BOX)$_2$ and Zn(BTZ)$_2$. Other than metal complexes, PBD, OXD-7, TAZ, BPhen, BCP, or the like can be used. The substances mentioned here are mainly substances that have an electron mobility of $10^{-6}$ cm$^2$/Vs or more. Note that other than these substances, any organic compound that has a property of transporting more electrons than holes may be used.

Examples of the electron donor which can be used are alkali metals, alkaline earth metals, rare earth metals, metals that belong to Group 13 of the periodic table, and oxides or carbonates thereof. Specifically, lithium (Li), cesium (Cs), magnesium (Mg), calcium (Ca), ytterbium (Yb), indium (In), lithium oxide, cesium carbonate, and the like are preferable. An organic compound, such as tetrathianaphthacene, may be used as the electron donor.

Note that forming the charge generation layer (I) 305 by using any of the above materials can suppress a drive voltage increase caused by the stack of the EL layers.

Figure 6B:
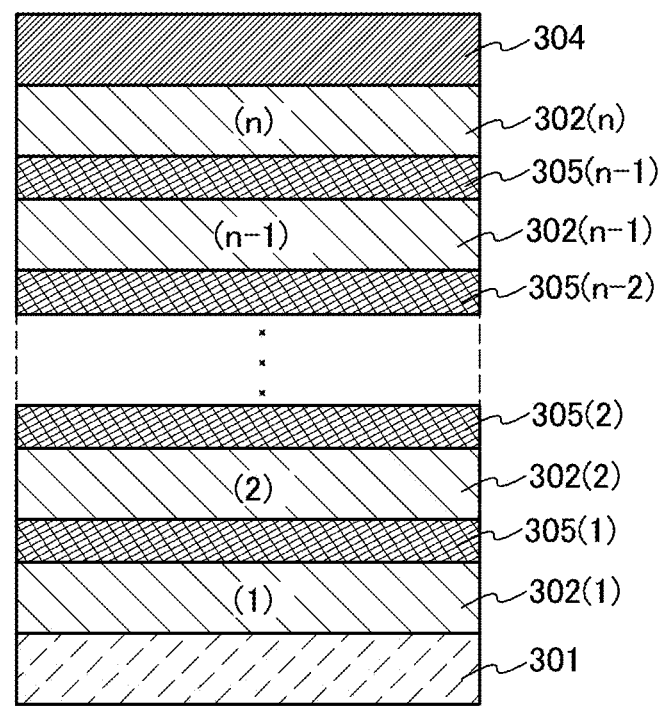

Although this embodiment shows the light-emitting element having two EL layers, the present invention can be similarly applied to a light-emitting element in which n EL layers (n is 3 or more) (302(1), 302(2), ..., 302(n−1), 302(n)) are stacked as illustrated in FIG. 6B. In the case where a plurality of EL layers is included between a pair of electrodes as in the light-emitting element according to this embodiment, by provision of the charge generation layers (I) (305(1), 305(2), ..., 305(n−2), 305(n−1))) between the EL layers, light emission in a high luminance region can be obtained with current density kept low. Since the current density can be kept low, the element can have a long lifetime. When the light-emitting element is applied to lighting, voltage drop due to resistance of an electrode material can be reduced, thereby achieving homogeneous light emission in a large area. Moreover, it is possible to achieve a light-emitting device which can be driven at a low voltage and has low power consumption.

Furthermore, by making emission colors of EL layers different, light of a desired color can be obtained from the light-emitting element as a whole. For example, the emission colors of first and second EL layers are complementary in a light-emitting element having the two EL layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors.

Further, the same applies to a light-emitting element having three EL layers. For example, the light-emitting element as a whole can emit white light when the emission color of the first EL layer is red, the emission color of the second EL layer is green, and the emission color of the third EL layer is blue.

Note that the structure described in this embodiment can be combined as appropriate with any of the structures described in the other embodiments.

(Embodiment 4)

In this embodiment, a light-emitting device which is one embodiment of the present invention is described.

Figure 7:
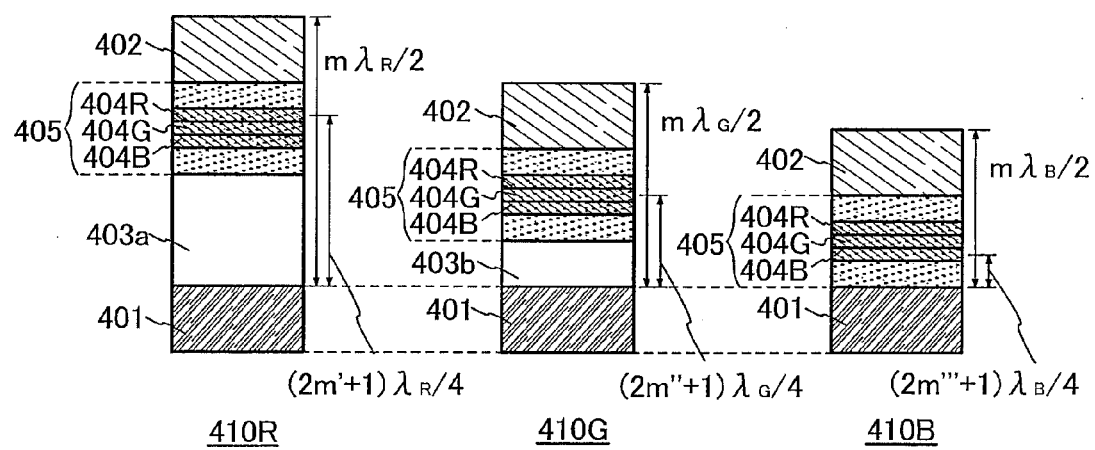
FIG. 7 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 7. Further, the EL layer 405 includes at least light-emitting layers 404 (404R, 404G, and 404B) each serving as a light-emitting region and may further include a hole-injection layer, a hole-transport layer, an electron-transport layer, an electron-injection layer, a charge generation layer (E), and the like. Note that the light-emitting layers 404 (404R, 404G, and 404B) can include the structures of light-emitting layers in one embodiment of the present invention which are described in Embodiments 1 and 2.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 7.

The first light-emitting element (R) 410R has a structure in which a first transparent conductive layer 403a; an EL layer 405 including a first light-emitting layer (B) 404B, a second light-emitting layer (G) 404G, and a third light-emitting layer (R) 404R in part; and a semi-transmissive and semi-reflective electrode 402 are sequentially stacked over a reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength region from 420 nm to 480 nm. The second light-emitting layer (G) 404G emits light ($\lambda_G$) having a peak in a wavelength region from 500 nm to 550 nm. The third light-emitting layer (R) 404R emits light ($\lambda_R$) having a peak in a wavelength region from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light region can be emitted. Note that the above wavelengths satisfy the relation of $\lambda_B < \lambda_G < \lambda_R$.

Each of the light-emitting elements described in this embodiment has a structure in which the EL layer 405 is provided between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1\times10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1\times10^{-2}$ Ωcm or lower is used.

In this embodiment, the thicknesses of the transparent conductive layers (the first transparent conductive layer 403a and the second transparent conductive layer 403b) provided in the first light-emitting element (R) 410R and the second light-emitting element (G) 410G, respectively, are varied between the light-emitting elements, whereby the light-emitting elements differ from each other in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be intensified while light with a wavelength that is not resonated therebetween can be attenuated. Thus, when the elements differ from each other in the optical path length from the reflective electrode 401 to the semi-transmissive and semi-reflective electrode 402, light with different wavelengths can be extracted.

Note that the optical path length (also referred to as optical distance) is expressed as a product of an actual distance and a refractive index, and in this embodiment, is a product of an actual thickness and n (refractive index). That is, an optical path length=actual thickness×n.

Further, the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is presumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness $((2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404. Therefore, by adjusting the optical path length from the reflective electrode 401 to the third light-emitting layer (R) 404R to the desired value $((2m'+1)\lambda_R/4$, where m' is a natural number), the phases of the first reflected light and the first incident light can be aligned with each other and the light emitted from the third light-emitting layer (R) 404R can be amplified.

Note that strictly speaking, the optical path length from the reflective electrode 401 to the third light-emitting layer (R) 404R can be the optical path length from a reflection region in the reflective electrode 401 to a light-emitting region in the third light-emitting layer (R) 404R. However, it is difficult to precisely determine the positions of the reflection region in the reflective electrode 401 and the light-emitting region in the third light-emitting layer (R) 404R; therefore, it is presumed that the above effect can be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness $((2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value $((2m''+1)\lambda_G/4$, where m'' is a natural number), the phases of the second reflected light and the second incident light can be aligned with each other and the light emitted from the second light-emitting layer (G) 404G can be amplified.

Note that strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404G; therefore, it is presumed that the above effect can be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness $((2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emitted from the first light-emitting layer (B) 404B can be amplified.

Note that strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is presumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 3 can be combined, in which case a plurality of EL layers and a charge generation layer interposed therebetween are provided in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layer, so that it is not needed to form light-emitting elements for the colors of R, G, and B. Therefore, the above structure is advantageous for full color display owing to easiness in achieving higher resolution display or the like. Note that a combination with coloring layers (color filters) is also possible. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

(Embodiment 5)

In this embodiment, a light-emitting device including a light-emitting element which is one embodiment of the present invention will be described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 8A and 8B.

Figure 8A:
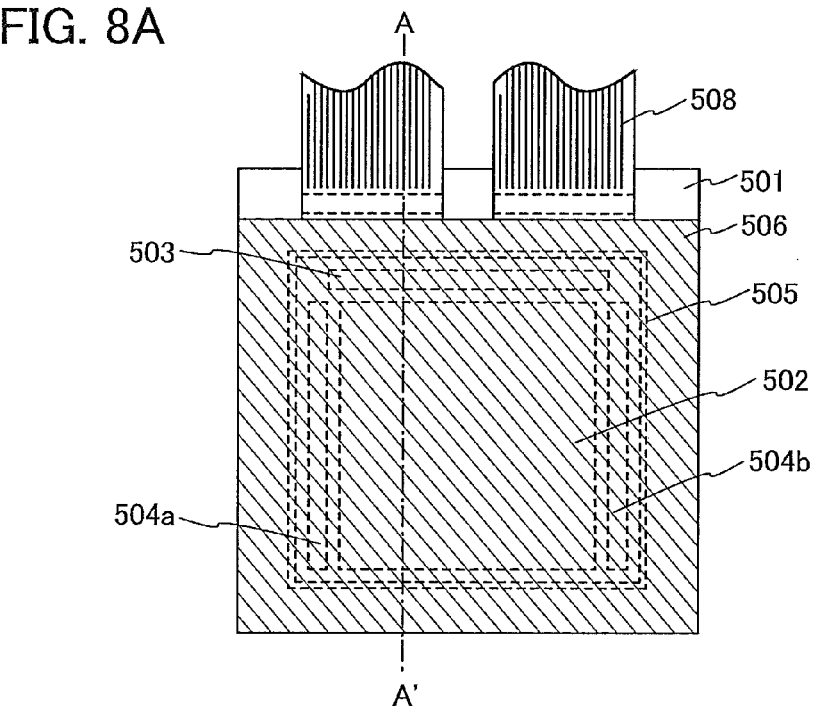
FIGS. 8A and 8B illustrate a light-emitting device.
Figure 8B:
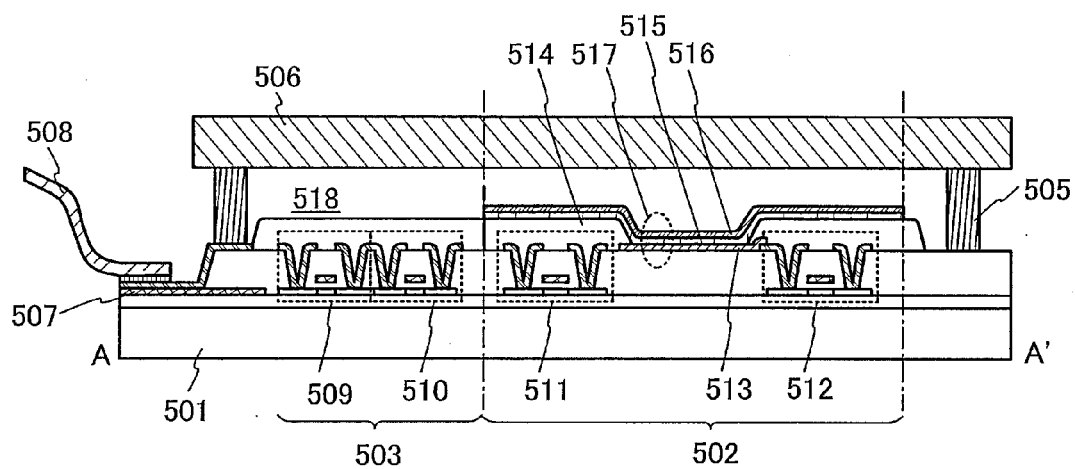

Note that FIG. 8A is a top view illustrating a light-emitting device and FIG. 8B is a cross-sectional view taken along the chain line A-A' in FIG. 8A. The active matrix light-emitting device according to this embodiment includes a pixel portion 502 provided over an element substrate 501, a driver circuit portion (a source line driver circuit) 503, and driver circuit portions (gate line driver circuits) 504 (504a and 504b). The pixel portion 502, the driver circuit portion 503, and the driver circuit portions 504 are sealed between the element substrate 501 and a sealing substrate 506 with a sealant 505.

In addition, there is provided a lead wiring 507 over the element substrate 501. The lead wiring 507 is provided for connecting an external input terminal through which a signal (e.g., a video signal, a clock signal, a start signal, or a reset signal) or a potential from the outside is transmitted to the driver circuit portion 503 and the driver circuit portions 504. Here is shown an example in which a flexible printed circuit (FPC) 508 is provided as the external input terminal. Although only the FPC is illustrated, this FPC may be provided with a printed wiring board (PWB). The light-emitting device in this specification includes, in its category, not only the light-emitting device itself but also the light-emitting device provided with the FPC or the PWB.

Next, a cross-sectional structure is described with reference to FIG. 8B. The driver circuit portions and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using any of various circuits, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 502 includes a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 µm to 3 µm) at the upper end portion. The insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided. The light-emitting layer has such a stacked-layer structure as described in Embodiment 1. Further, in the EL layer 515, a hole-injection layer, a hole-transport layer, an electron-transport layer, an electron-injection layer, a charge generation layer, and the like can be provided as appropriate in addition to the light-emitting layer.

The stacked-layer structure including the first electrode (anode) 513, the EL layer 515, and the second electrode (cathode) 516 forms a light-emitting element 517. For the first electrode (anode) 513, the EL layer 515, and the second electrode (cathode) 516, the materials described in Embodiment 2 can be used. Although not illustrated, the second electrode (cathode) 516 is electrically connected to the FPC 508 which is an external input terminal.

Although the cross-sectional view in FIG. 8B illustrates only one light-emitting element 517, a plurality of light-emitting elements is arranged in a matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device capable of full color display may be fabricated by a combination with coloring layers (color filters).

Further, the sealing substrate 506 is attached to the element substrate 501 with the sealant 505, whereby the light-emitting element 517 is provided in a space 518 surrounded by the element substrate 501, the sealing substrate 506, and the sealant 505. The space 518 may be filled with an inert gas (such as nitrogen or argon) or the sealant 505.

An epoxy-based resin or low-melting-point glass is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride (PVF), polyester, acrylic, or the like can be used.

As described above, an active matrix light-emitting device can be obtained.

Note that the structure described in this embodiment can be combined as appropriate with any of the structures described in the other embodiments.

(Embodiment 6)

In this embodiment, examples of a variety of electronic devices which are completed using a light-emitting device will be described with reference to FIGS. 9A to 9D and FIGS. 10A to 10C. The light-emitting device is fabricated using a light-emitting element which is one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices are illustrated in FIGS. 9A to 9D.

Figure 9A:
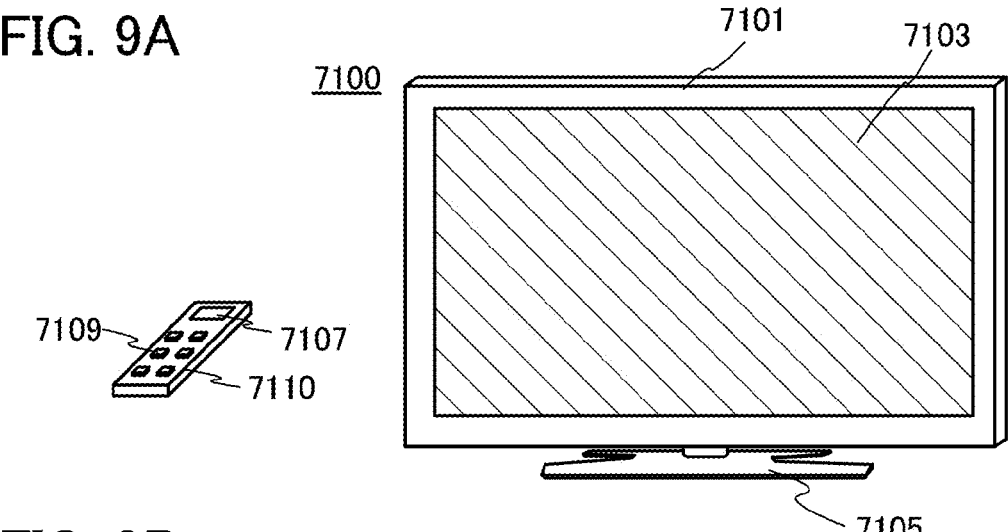
FIGS. 9A to 9D illustrate electronic devices.

FIG. 9A illustrates an example of a television device. In a television device 7100, a display portion 7103 is incorporated in a housing 7101. The display portion 7103 is capable of displaying images, and a light-emitting device can be used for the display portion 7103. In addition, here, the housing 7101 is supported by a stand 7105.

The television device 7100 can be operated with an operation switch provided in the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 9B:
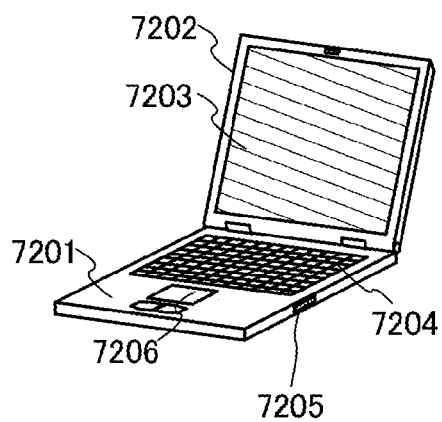

FIG. 9B illustrates a computer, which includes a main body 7201, a housing 7202, a display portion 7203, a keyboard 7204, an external connection port 7205, a pointing device 7206, and the like. Note that this computer is manufactured by using a light-emitting device for the display portion 7203.

Figure 9C:
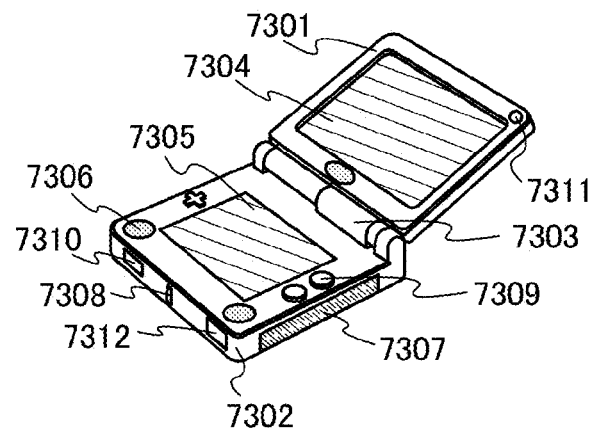

FIG. 9C illustrates a portable game machine, which includes two housings, i.e., a housing 7301 and a housing 7302, connected to each other via a joint portion 7303 so that the portable game machine can be opened or closed. A display portion 7304 is incorporated in the housing 7301 and a display portion 7305 is incorporated in the housing 7302. In addition, the portable game machine illustrated in FIG. 9C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), and a microphone 7312), and the like. It is needless to say that the structure of the portable game machine is not limited to the above structure as long as a light-emitting device is used for at least either the display portion 7304 or the display portion 7305, or both, and may include other accessories as appropriate. The portable game machine illustrated in FIG. 9C has a function of reading out a program or data stored in a storage medium to display it on the display portion, and a function of sharing information with another portable game machine by wireless communication. Note that the portable game machine illustrated in FIG. 9C can have a variety of functions without limitation to those above.

Figure 9D:
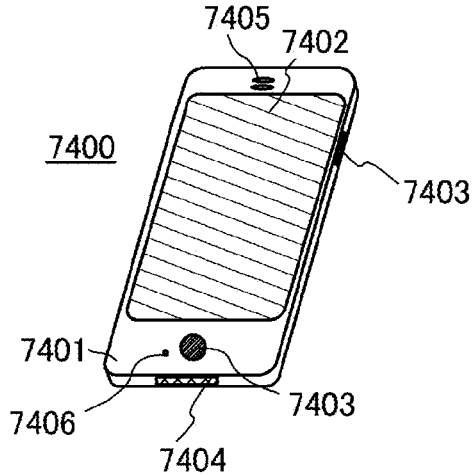

FIG. 9D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured using a light-emitting device for the display portion 7402.

When the display portion 7402 of the cellular phone 7400 illustrated in FIG. 9D is touched with a finger or the like, data can be input to the cellular phone 7400. Further, operations such as making a call and creating e-mail can be performed by touch on the display portion 7402 with a finger or the like.

There are mainly three screen modes for the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a character input mode mainly for inputting characters is selected for the display portion 7402 so that characters displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are changed by touch on the display portion 7402 or operation with the operation buttons 7403 of the housing 7401. Alternatively, the screen modes can be changed depending on the kind of image displayed on the display portion 7402. For example, when a signal for an image to be displayed on the display portion is data of moving images, the screen mode is changed to the display mode. When the signal is text data, the screen mode is changed to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by touch on the display portion 7402 with the palm or the finger, whereby personal identification can be performed. Furthermore, when a backlight or a sensing light source which emits near-infrared light is provided for the display portion, an image of a finger vein, a palm vein, or the like can also be taken.

Figure 10A:
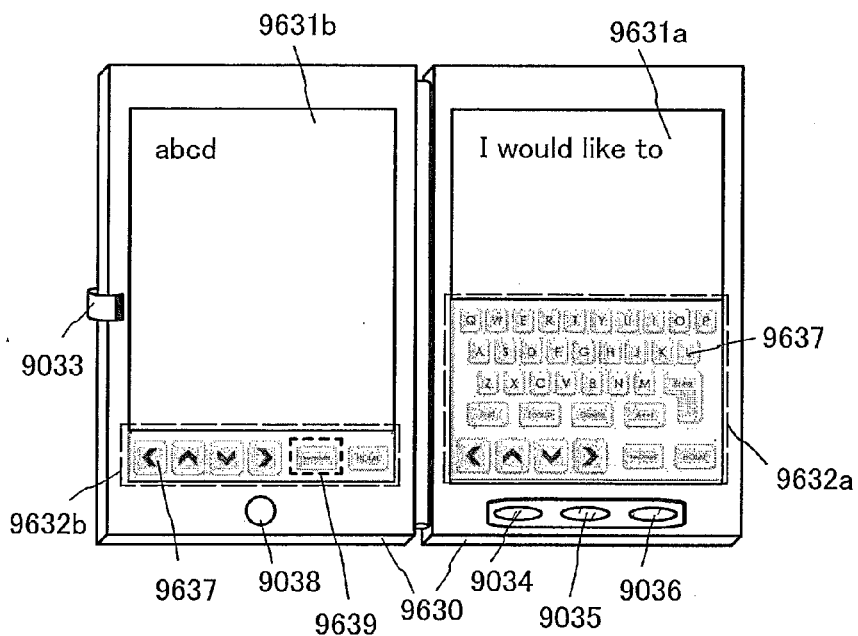
FIGS. 10A to 10C illustrate an electronic device.
Figure 10B:
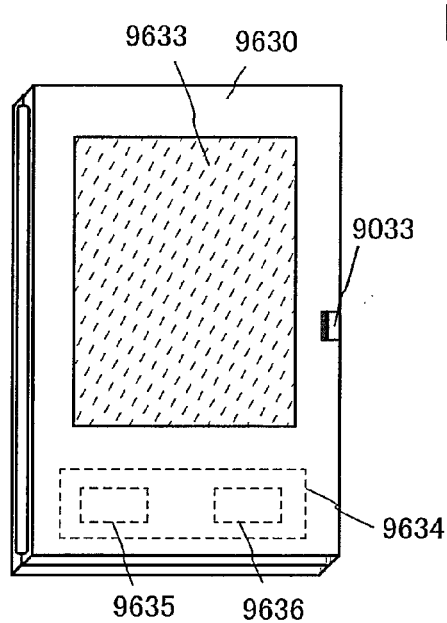

FIGS. 10A and 10B illustrate a foldable tablet terminal. The tablet terminal is opened in FIG. 10A. The tablet terminal includes a housing 9630, a display portion 9631a, a display portion 9631b, a display mode switch 9034, a power switch 9035, a power saver switch 9036, a clasp 9033, and an operation switch 9038. The tablet terminal is manufactured using the light-emitting device for either the display portion 9631a or the display portion 9631b or both.

Part of the display portion 9631a can be a touch panel region 9632a and data can be input when a displayed operation key 9637 is touched. Although a structure in which a half region in the display portion 9631a has only a display function and the other half region also has a touch panel function is shown as an example, the display portion 9631a is not limited to the structure. The whole region in the display portion 9631a may have a touch panel function. For example, the display portion 9631a can display keyboard buttons in the whole region to be a touch panel, and the display portion 9631b can be used as a display screen.

As in the display portion 9631a, part of the display portion 9631b can be a touch panel region 9632b. When a keyboard display switching button 9639 displayed on the touch panel is touched with a finger, a stylus, or the like, a keyboard can be displayed on the display portion 9631b.

Touch input can be performed in the touch panel region 9632a and the touch panel region 9632b at the same time.

The display mode switch 9034 can switch the display between portrait mode, landscape mode, and the like, and between monochrome display and color display, for example. The power saver switch 9036 can control display luminance in accordance with the amount of external light in use of the tablet terminal detected by an optical sensor incorporated in the tablet terminal. In addition to the optical sensor, another detection device including a sensor for detecting inclination, such as a gyroscope or an acceleration sensor, may be incorporated in the tablet terminal.

FIG. 10A shows an example in which the display portion 9631a and the display portion 9631b have the same display area; however, without limitation thereon, one of the display portions may be different from the other display portion in size and display quality. For example, one display panel may be capable of higher-definition display than the other display panel.

The tablet terminal is closed in FIG. 10B. The tablet terminal includes the housing 9630, a solar cell 9633, a charge and discharge control circuit 9634, a battery 9635, and a DCDC converter 9636. In FIG. 10B, a structure including the battery 9635 and the DCDC converter 9636 is illustrated as an example of the charge and discharge control circuit 9634.

Since the tablet terminal is foldable, the housing 9630 can be closed when the tablet terminal is not used. As a result, the display portion 9631a and the display portion 9631b can be protected; thus, a tablet terminal which has excellent durability and excellent reliability in terms of long-term use can be provided.

In addition, the tablet terminal illustrated in FIGS. 10A and 10B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar cell 9633 can be provided on one or both surfaces of the housing 9630 and the battery 9635 can be charged efficiently. The use of a lithium ion battery as the battery 9635 is advantageous in downsizing or the like.

The structure and the operation of the charge and discharge control circuit 9634 illustrated in FIG. 10B will be described with reference to a block diagram in FIG. 10C. The solar cell 9633, the battery 9635, the DCDC converter 9636, a converter 9638, switches SW1 to SW3, and a display portion 9631 are illustrated in FIG. 10C, and the battery 9635, the DCDC converter 9636, the converter 9638, and the switches SW1 to SW3 correspond to the charge and discharge control circuit 9634 illustrated in FIG. 10B.

First, an example of the operation in the case where power is generated by the solar cell 9633 using external light is described. The voltage of power generated by the solar cell 9633 is stepped up or down by the DCDC converter 9636 so that the power has a voltage for charging the battery 9635. Then, when the power from the solar cell 9633 is used for the operation of the display portion 9631, the switch SW1 is turned on and the voltage of the power is stepped up or down by the converter 9638 so as to be a voltage needed for the display portion 9631. In addition, when display on the display portion 9631 is not performed, the switch SW1 is turned off and the switch SW2 is turned on so that the battery 9635 may be charged.

Note that the solar cell 9633 is described as an example of a power generation means; however, without limitation thereon, the battery 9635 may be charged using another power generation means such as a piezoelectric element or a thermoelectric conversion element (Peltier element). For example, a non-contact electric power transmission module which transmits and receives power wirelessly (without contact) to charge the battery 9635, or a combination of the solar cell 9633 and another means for charge may be used.

Figure 10C:
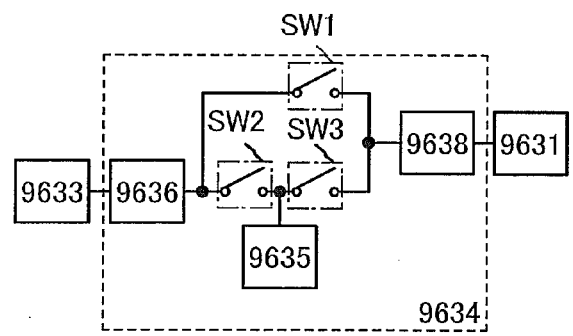

It is needless to say that an embodiment of the present invention is not limited to the electronic device illustrated in FIGS. 10A to 10C as long as the display portion described in the above embodiment is included.

As described above, the electronic devices can be obtained by the use of the light-emitting device which is one embodiment of the present invention. The light-emitting device has a remarkably wide application range, and can be applied to electronic devices in a variety of fields.

Note that the structure described in this embodiment can be combined as appropriate with any of the structures described in the other embodiments.

(Embodiment 7)

In this embodiment, examples of lighting devices will be described with reference to FIG. 11. A light-emitting device including a light-emitting element which is one embodiment of the present invention is applied to the lighting devices.

Figure 11:
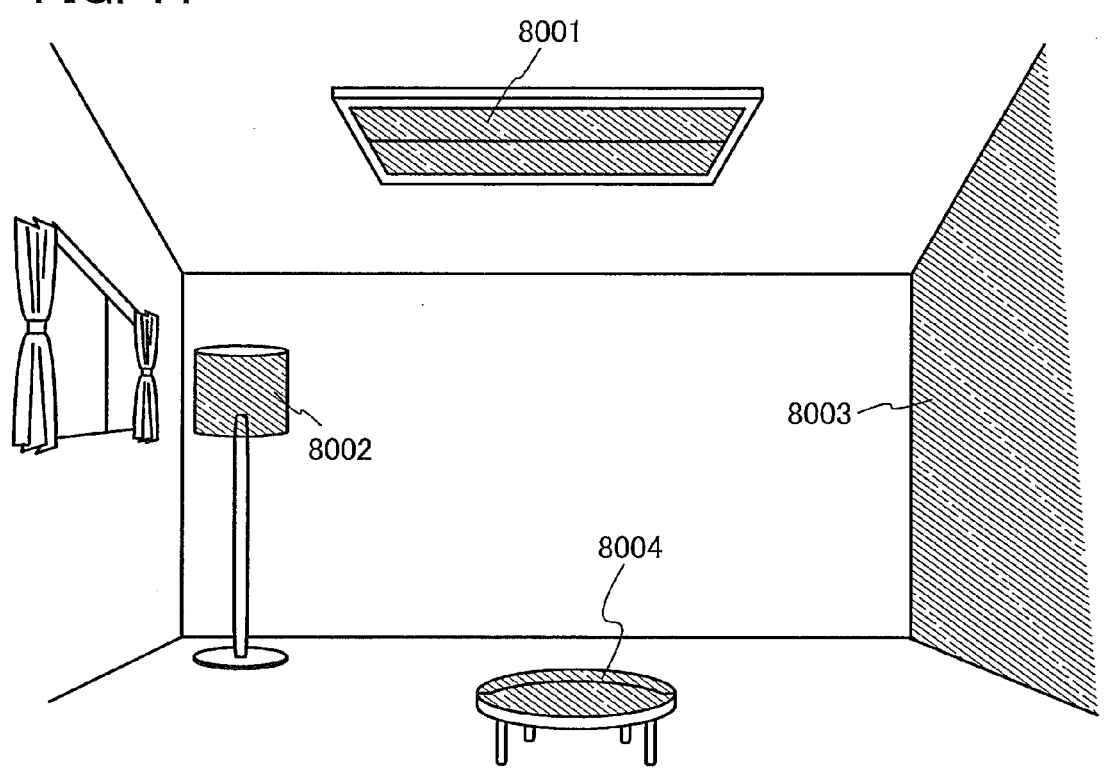
FIG. 11 illustrates lighting devices.

FIG. 11 illustrates an example in which a light-emitting device is used for an interior lighting device 8001. Since the light-emitting device can have a larger area, a lighting device having a large area can also be formed. In addition, a lighting device 8002 in which a light-emitting region has a curved surface can also be formed with the use of a housing with a curved surface. A light-emitting element included in the light-emitting device described in this embodiment is in the form of a thin film, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

The structure described in this embodiment can be combined as appropriate with any of the structures described in the other embodiments.

EXAMPLE 1

Figure 12:
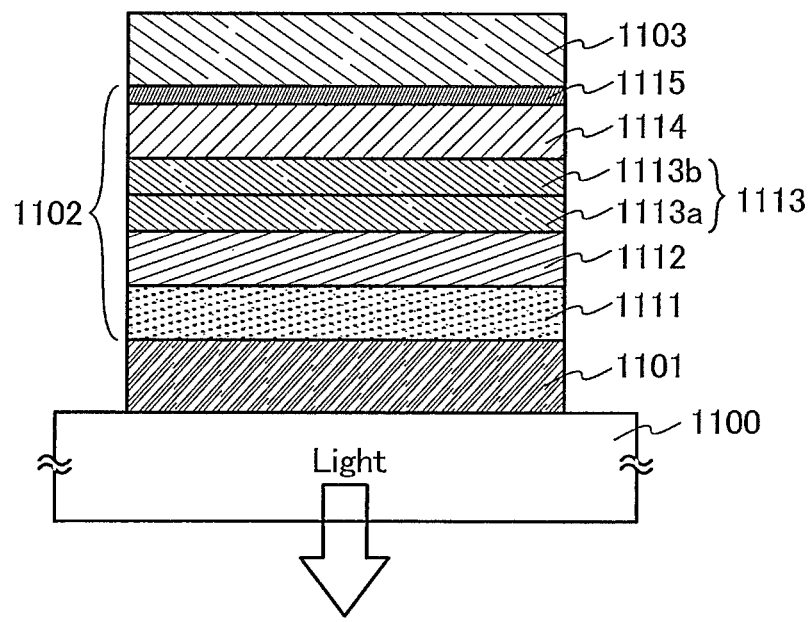
FIG. 12 illustrates a structure of a light-emitting element 1.

In this example, a light-emitting element 1 which is one embodiment of the present invention is described with reference to FIG. 12. Chemical formulae of materials used in this example are shown below.

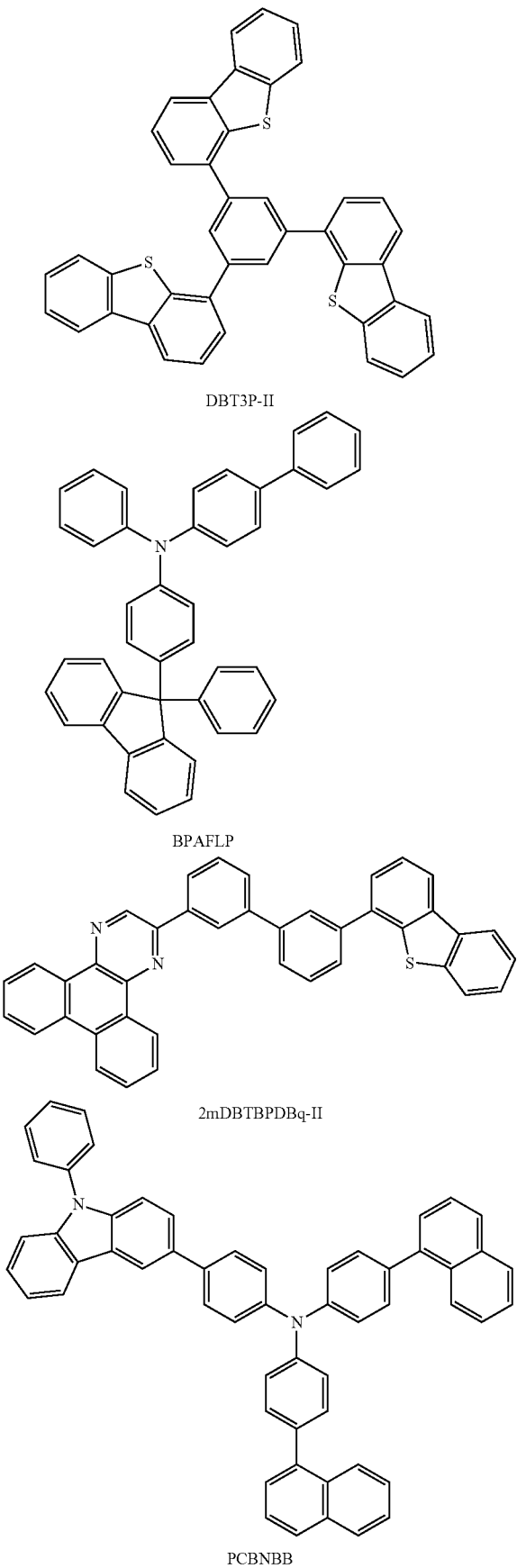

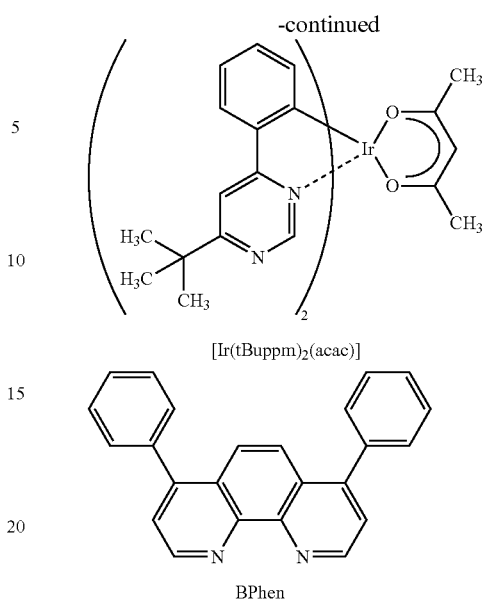

《Fabrication of Light-emitting Element 1》

First, a film of indium tin oxide containing silicon oxide (ITSO) was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element 1 over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder in the vacuum evaporation apparatus so that a surface on which the first electrode 1101 was provided faced downward. In this example, a case is described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

The pressure in the vacuum evaporation apparatus was reduced to about $10^{-4}$ Pa. Then, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was set to 40 nm. Note that co-evaporation is an evaporation method by which a plurality of different substances is concurrently vaporized from respective different evaporation sources.

Next, the hole-transport layer 1112 was formed by evaporation of 4-phenyl-4'-(9-phenylfluoren-9-yl)triphenylamine (abbreviation: BPAFLP) to a thickness of 20 nm.

Next, the light-emitting layer 1113 was formed over the hole-transport layer 1112. The light-emitting layer 1113 having a stacked-layer structure was formed by forming a first light-emitting layer 1113a with a thickness of 20 nm by co-evaporation of 2-[3'-(dibenzothiophen-4-yl)biphenyl-3-yl]dibenzo[f,h]quinoxaline (abbreviation: 2mDBTBPDBq-II), 4,4'-di(1-naphthyl)-4"-(9-phenyl-9H-carbazol-3-yl)triphenylamine (abbreviation: PCBNBB), and (acetylacetonato)bis(6-tert-butyl-4-phenylpyrimidinato)iridium(III) (abbreviation: [Ir(tBuppm)$_2$(acac)]) with a mass ratio of 2mDBTBPDBq-II (abbreviation) to PCBNBB (abbreviation) and [Ir(tBuppm)$_2$(acac)] (abbreviation) being 0.8:0.2:0.05, and then forming a second light-emitting layer 1113b with a thickness of 20 nm by co-evaporation with a mass ratio of 2mDBTBPDBq-II (abbreviation) to [Ir(tBuppm)$_2$(acac)] (abbreviation) being 1:0.05.

Next, over the light-emitting layer 1113, the electron-transport layer 1114 was formed in such a manner that a film of 2mDBTBPDBq-II (abbreviation) was formed by evaporation to a thickness of 10 nm and then a film of bathophenanthroline (abbreviation: BPhen) was formed by evaporation to a thickness of 20 nm. Further, over the electron-transport layer 1114, a film of lithium fluoride was formed by evaporation to a thickness of 1 nm to form the electron-injection layer 1115.

Lastly, over the electron-injection layer 1115, an aluminum film was formed by evaporation to a thickness of 200 nm as a second electrode 1103 functioning as a cathode. Thus, the light-emitting element 1 was fabricated. Note that, in all the above evaporation steps, evaporation was performed by a resistance-heating method.

Table 1 shows an element structure of the light-emitting element 1 obtained as described above.

Figure 14:
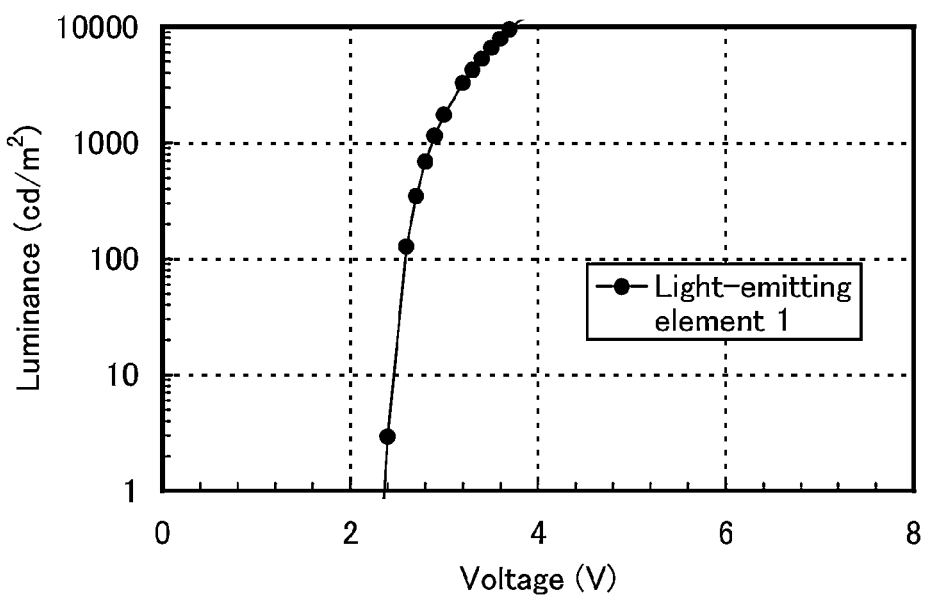
FIG. 14 shows voltage-luminance characteristics of the light-emitting element 1.
Figure 15:
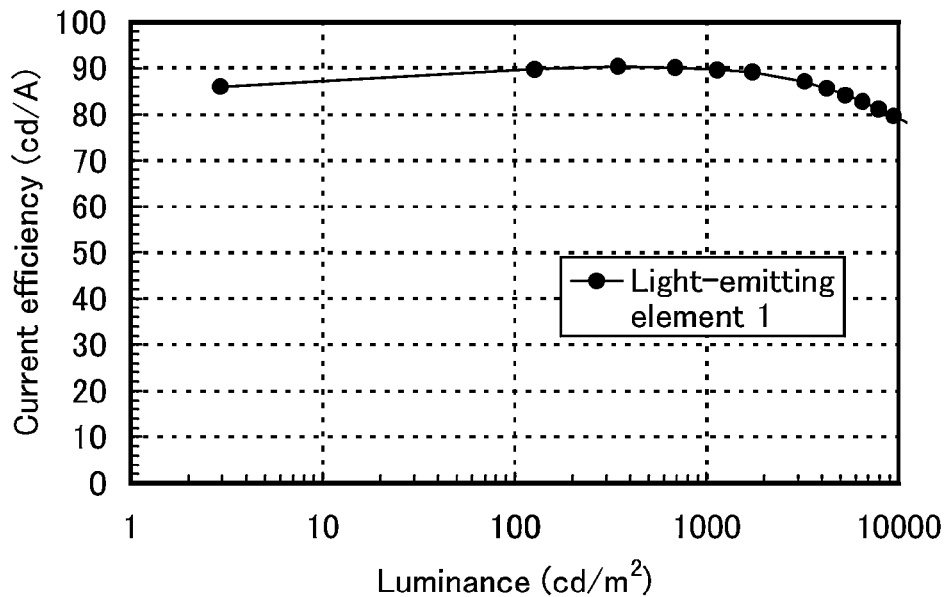
FIG. 15 shows luminance-current efficiency characteristics of the light-emitting element 1.
Figure 16:
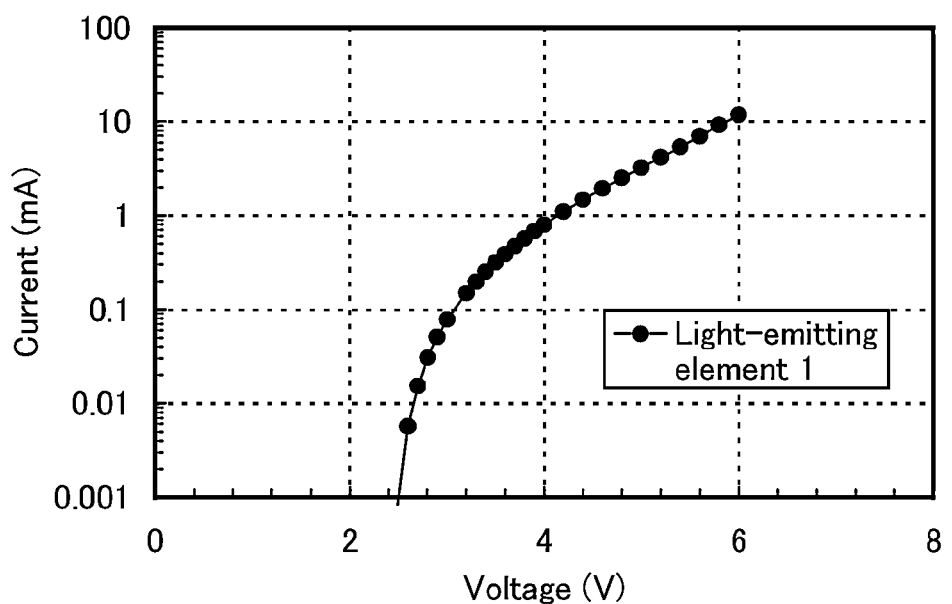
FIG. 16 shows voltage-current characteristics of the light-emitting element 1.

FIG. 14, the vertical axis represents luminance (cd/m$^2$), and the horizontal axis represents voltage (V). FIG. 15 shows luminance-current efficiency characteristics of the light-emitting element 1. In FIG. 15, the vertical axis represents current efficiency (cd/A), and the horizontal axis represents luminance (cd/m$^2$). FIG. 16 shows voltage-current characteristics of the light-emitting element 1. In FIG. 16, the vertical axis represents current (mA), and the horizontal axis represents voltage (V).

FIG. 14 reveals high efficiency of the light-emitting element 1 that is one embodiment of the present invention. Table 2 below shows initial values of main characteristics of the light-emitting element 1 at a luminance of about 1000 cd/m$^2$.

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
| --- | --- | --- | --- | --- | --- | --- | --- | --- |
| Light-emitting element 1 | 2.9 | 0.05 | 1.3 | (0.44, 0.55) | 1100 | 90 | 97 | 25 |

The above results show that the light-emitting element 1 fabricated in this example has high external quantum efficiency, which means its high emission efficiency. Moreover, as for color purity, it can be found that the light-emitting element exhibits yellow-green emission with excellent color purity.

Figure 17:
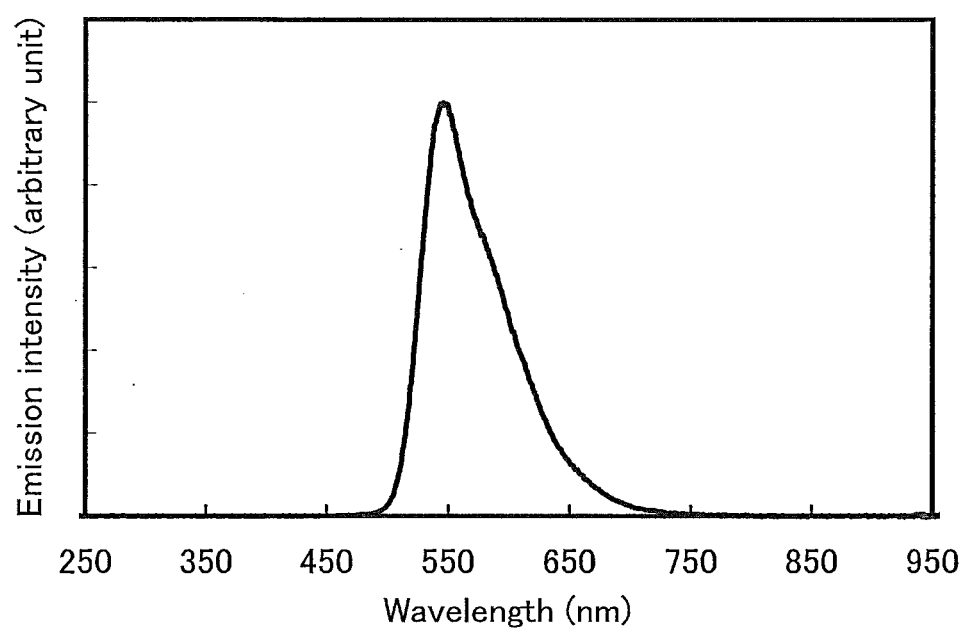
FIG. 17 shows an emission spectrum of the light-emitting element 1.

FIG. 17 shows an emission spectrum when a current at a current density of 25 mA/cm$^2$ was supplied to the light-emitting element 1. FIG. 17 shows that the emission spectrum of the light-emitting element 1 has a peak at around 550 nm, which indicates that the peak is derived from emission from the phosphorescent organometallic iridium complex [Ir(tBuppm)$_2$(acac)].

Figure 18:
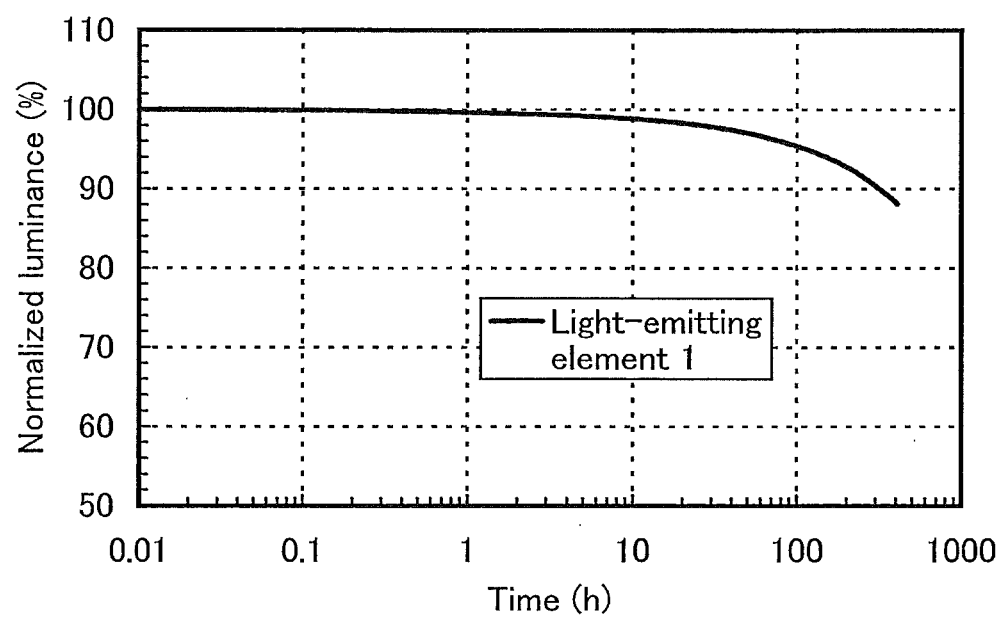
FIG. 18 shows reliability of the light-emitting element 1.

FIG. 18 shows results of a reliability test of the light-emitting element 1. In FIG. 18, the vertical axis represents

TABLE 1

|  | First electrode | Hole-injection layer | Hole-transport layer | Light-emitting layer | | Electron-transport layer | | Electron-injection layer | Second electrode |
| --- | --- | --- | --- | --- | --- | --- | --- | --- | --- |
| Light-emitting element 1 | ITSO (110 nm) | DBT3P-II:MoOx (4:2, 40 nm) | BPAFLP (20 nm) | * | ** | 2mDBTBPDBq-II (10 nm) | BPhen (20 nm) | LiF (1 nm) | Al (200 nm) |

* 2mDBTBPDBq-II:PCBNBB:[Ir(tBuppm)$_2$(acac)] (0.8:0.2:0.05, 20 nm)
** 2mDBTBPDBq-II:[Ir(tBuppm)$_2$(acac)] (1:0.05, 20 nm)

The fabricated light-emitting element 1 was sealed in a glove box containing a nitrogen atmosphere so as not to be exposed to air (specifically, a sealant was applied to an outer edge of the element and heat treatment was performed at 80° C. for 1 hour at the time of sealing).

《Operation Characteristics of Light-emitting Element 1》

Operation characteristics of the fabricated light-emitting element 1 were measured. Note that the measurements were carried out at room temperature (in an atmosphere kept at 25° C.).

Figure 13:
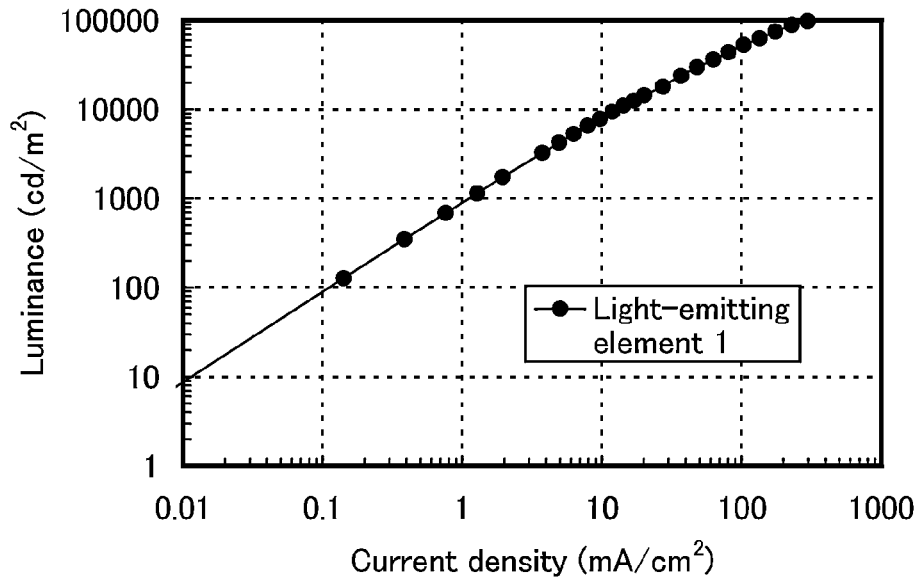
FIG. 13 shows current density-luminance characteristics of the light-emitting element 1.

First, FIG. 13 shows current density-luminance characteristics of the light-emitting element 1. In FIG. 13, the vertical axis represents luminance (cd/m$^2$), and the horizontal axis represents current density (mA/cm$^2$). FIG. 14 shows voltage-luminance characteristics of the light-emitting element 1. In normalized luminance (%) with an initial luminance of 100%, and the horizontal axis represents driving time (h) of the element. Note that in the reliability test, the light-emitting element 1 was driven under the conditions where the initial luminance was set to 5000 cd/m$^2$ and the current density was constant. As a result, the light-emitting element 1 kept about 88% of the initial luminance after 400 hours elapsed.

Thus, the reliability test revealed that the light-emitting element 1 has high reliability and a long lifetime.

Note that a film of 2mDBTBPDBq-II (abbreviation), a film of PCBNBB (abbreviation), and a mixed film of 2mDBTBPDBq-II (abbreviation) and PCBNBB (abbreviation) were manufactured, and photoluminescence (PL) of each of the films was measured. The results are that the photoluminescence (PL) peak wavelength of the evaporation film of 2mDBTBPDBq-II (abbreviation) was 428 nm and the PL peak wavelength of the evaporation film of PCBNBB (abbreviation) was 428 nm, whereas the PL peak wavelength of the mixed film formed by co-evaporation of these substances was 501 nm and significantly shifted to a longer wavelength side. Thus, it can be seen that the combination of 2mDBTBPDBq-II (abbreviation) and PCBNBB (abbreviation) forms an exciplex.

EXAMPLE 2

In this example, a light-emitting element 2 which is one embodiment of the present invention is described. Note that in the description of the light-emitting element 2 in this example, FIG. 12 which is used in the description of the light-emitting element 1 in Example 1 is to be referred to. Chemical formulae of materials used in this example are shown below.

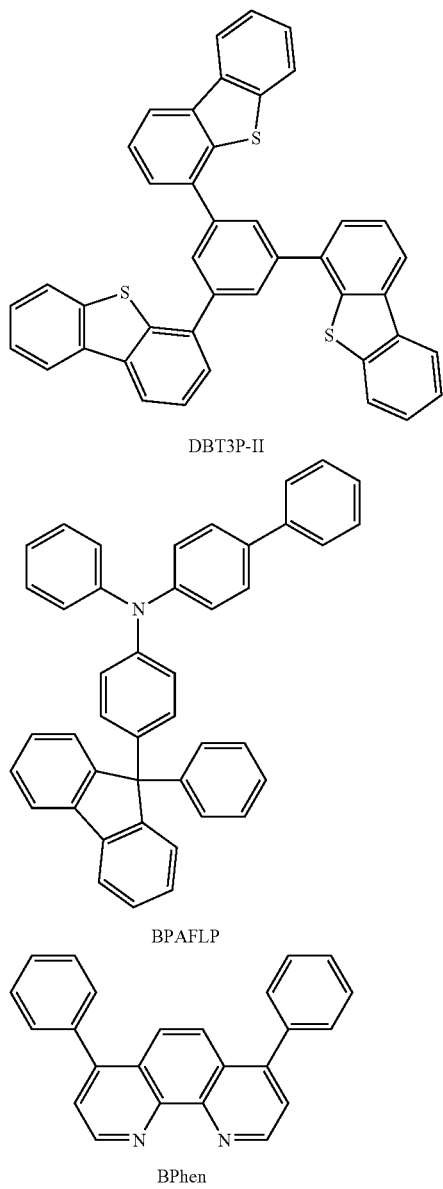

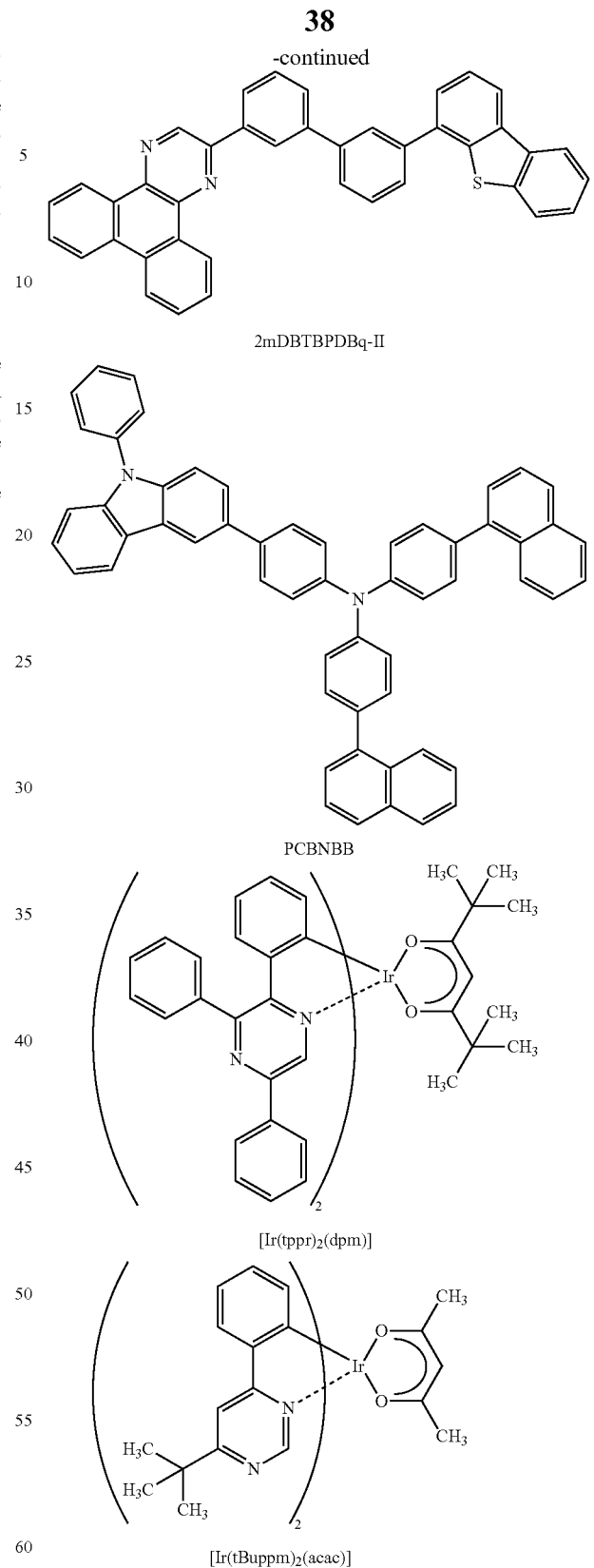

《Fabrication of Light-emitting Element 2》

First, a film of indium tin oxide containing silicon oxide (ITSO) was formed over a glass substrate 1100 by a sputtering method, so that a first electrode 1101 functioning as an anode was formed. Note that the thickness was set to 110 nm and the electrode area was set to 2 mm×2 mm.

Next, as pretreatment for forming the light-emitting element 2 over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder in the vacuum evaporation apparatus so that a surface on which the first electrode 1101 was provided faced downward. In this example, a case is described in which a hole-injection layer 1111, a hole-transport layer 1112, a light-emitting layer 1113, an electron-transport layer 1114, and an electron-injection tion: [Ir(tppr)$_2$(dpm)]) with a mass ratio of 2mDBTBPDBq-II (abbreviation) to [Ir(tppr)$_2$(dpm)] (abbreviation) being 1:0.06.

Next, over the light-emitting layer 1113, the electron-transport layer 1114 was formed in such a manner that a film of 2mDBTBPDBq-II (abbreviation) was formed by evaporation to a thickness of 15 nm and then a film of bathophenanthroline (abbreviation: BPhen) was formed by evaporation to a thickness of 15 nm. Further, over the electron-transport layer 1114, a film of lithium fluoride was formed by evaporation to a thickness of 1 nm to form the electron-injection layer 1115.

Lastly, over the electron-injection layer 1115, an aluminum film was formed by evaporation to a thickness of 200 nm as a second electrode 1103 functioning as a cathode. Thus, the light-emitting element 2 was fabricated. Note that, in all the above evaporation steps, evaporation was performed by a resistance-heating method.

Table 3 shows an element structure of the light-emitting element 2 obtained as described above.

TABLE 3

| | First electrode | Hole-injection layer | Hole-transport layer | Light-emitting layer | | | Electron-transport layer | | Electron-injection layer | Second electrode |
|---|---|---|---|---|---|---|---|---|---|---|
| Light-emitting element 2 | ITSO (110 nm) | DBT3P-II:MoOx (4:2, 33 nm) | BPAFLP (20 nm) | * | ** | 2mDBTBPDBq-II (15 nm) | BPhen (15 nm) | LiF (1 nm) | Al (200 nm) |

\* 2mDBTBPDBq-II:PCBNBB:[Ir(tBuppm)$_2$(acac)] (0 8:0.2:0.05 20 nm)
\*\* 2mDBTBPDBq-II:[Ir(tppr)$_2$(dpm)] (1:0.06 20 nm)

layer 1115 which are included in an EL layer 1102 are sequentially formed by a vacuum evaporation method.

The pressure in the vacuum evaporation apparatus was reduced to about $10^{-4}$ Pa. Then, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was set to 33 nm. Note that co-evaporation is an evaporation method by which a plurality of different substances is concurrently vaporized from respective different evaporation sources.

Next, the hole-transport layer 1112 was formed by evaporation of BPAFLP (abbreviation) to a thickness of 20 nm.

Next, the light-emitting layer 1113 was formed over the hole-transport layer 1112. The light-emitting layer 1113 having a stacked-layer structure was formed by forming a first light-emitting layer 1113a with a thickness of 20 nm by co-evaporation of 2-[3'-(dibenzothiophen-4-yl)biphenyl-3-yl]dibenzo[f,h]quinoxaline (abbreviation: 2mDBTBPDBq-II), 4,4'-di(1-naphthyl)-4"-(9-phenyl-9H-carbazol-3-yl)triphenylamine (abbreviation: PCBNBB), and (acetylacetonato)bis(6-tert-butyl-4-phenylpyrimidinato)iridium(III) (abbreviation: [Ir(tBuppm)$_2$(acac)]) with a mass ratio of 2mDBTBPDBq-II (abbreviation) to PCBNBB (abbreviation) and [Ir(tBuppm)$_2$(acac)] (abbreviation) being 0.8:0.2:0.05, and then forming a second light-emitting layer 1113b with a thickness of 20 nm by co-evaporation of 2mDBTBPDBq-II (abbreviation) and bis(2,3,5-triphenylpyradinato)(dipivaloylmethanato)iridium(III) (abbrevia- The fabricated light-emitting element 2 was sealed in a glove box containing a nitrogen atmosphere so as not to be exposed to air (specifically, a sealant was applied to an outer edge of the element and heat treatment was performed at 80° C. for 1 hour at the time of sealing).

《Operation Characteristics of Light-emitting Element 2》

Operation characteristics of the fabricated light-emitting element 2 were measured. Note that the measurements were carried out at room temperature (in an atmosphere kept at 25° C.).

Figure 19:
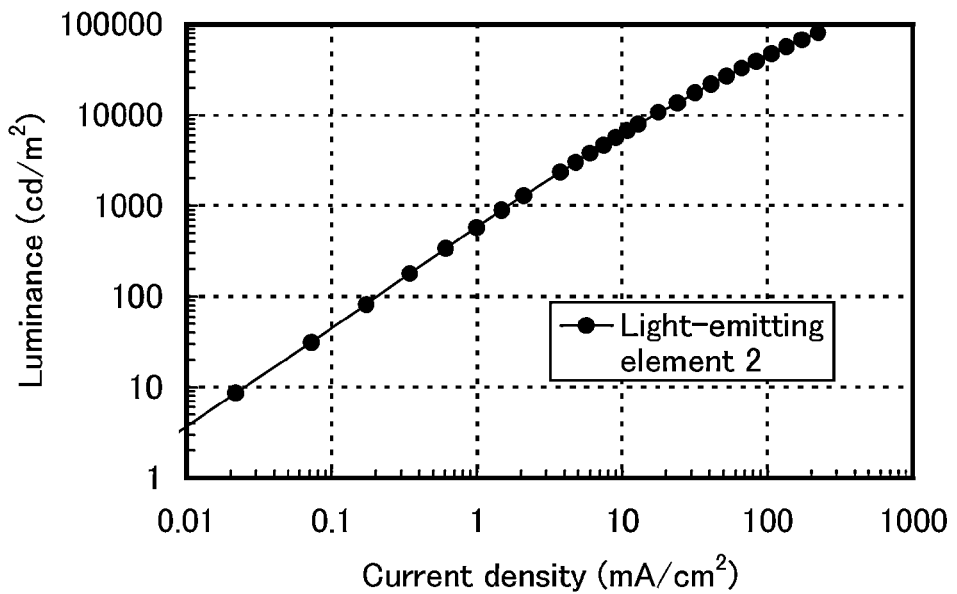
FIG. 19 shows current density-luminance characteristics of a light-emitting element 2.
Figure 20:
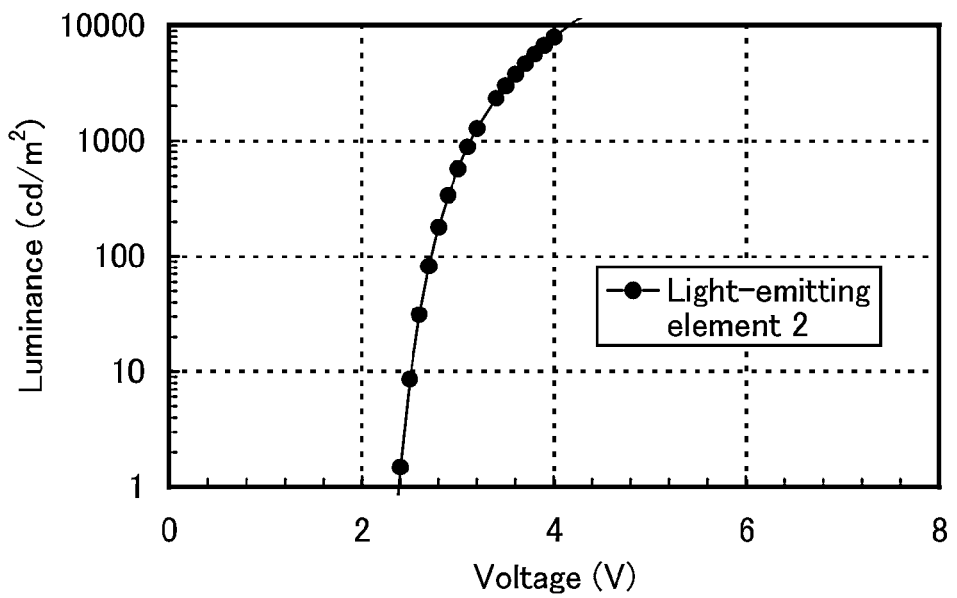
FIG. 20 shows voltage-luminance characteristics of the light-emitting element 2.
Figure 21:
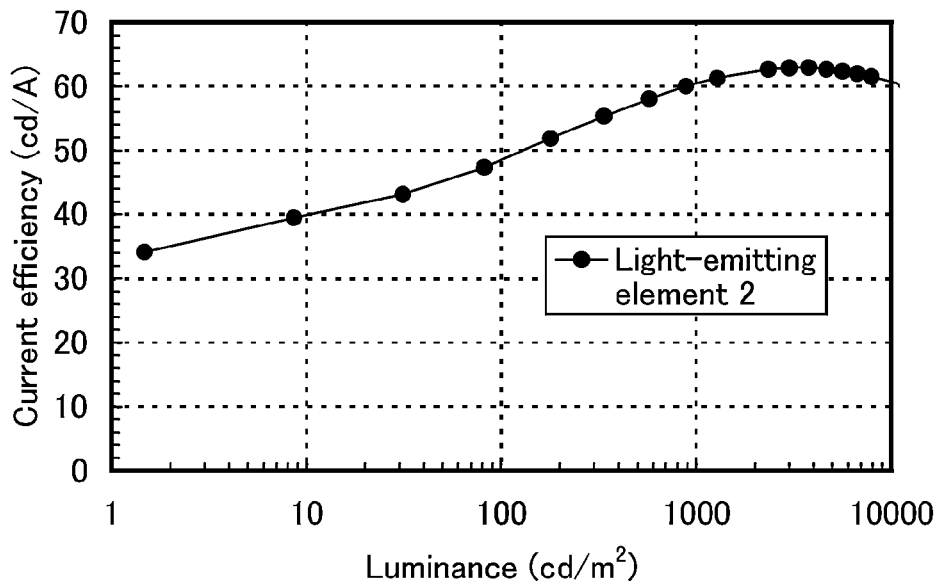
FIG. 21 shows luminance-current efficiency characteristics of the light-emitting element 2.
Figure 22:
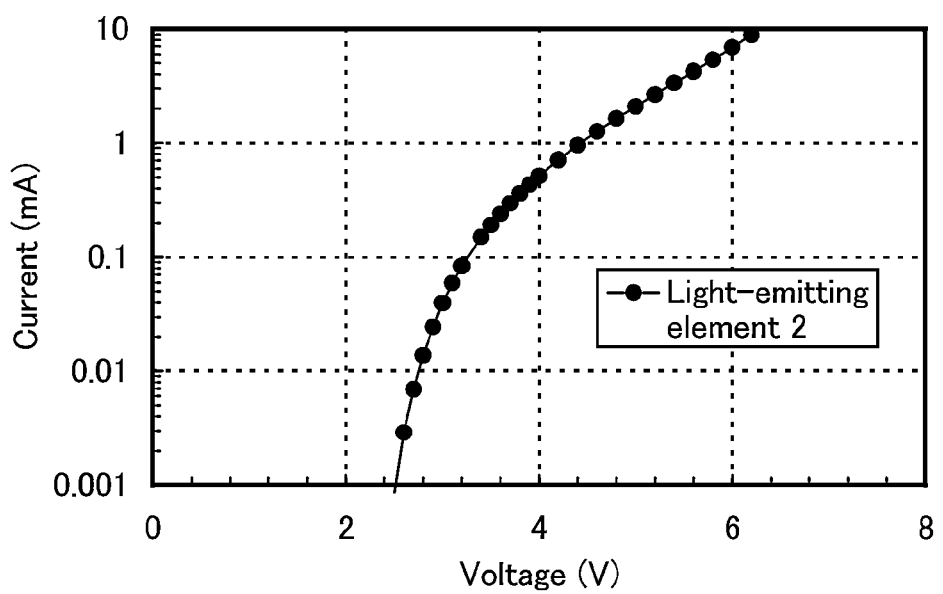
FIG. 22 shows voltage-current characteristics of the light-emitting element 2.

First, FIG. 19 shows current density-luminance characteristics of the light-emitting element 2. In FIG. 19, the vertical axis represents luminance (cd/m$^2$), and the horizontal axis represents current density (mA/cm$^2$). FIG. 20 shows voltage-luminance characteristics of the light-emitting element 2. In FIG. 20, the vertical axis represents luminance (cd/m$^2$), and the horizontal axis represents voltage (V). FIG. 21 shows luminance-current efficiency characteristics of the light-emitting element 2. In FIG. 21, the vertical axis represents current efficiency (cd/A), and the horizontal axis represents luminance (cd/m$^2$). FIG. 22 shows voltage-current characteristics of the light-emitting element 2. In FIG. 22, the vertical axis represents current (mA), and the horizontal axis represents voltage (V).

FIG. 21 reveals high efficiency of the light-emitting element 2 that is one embodiment of the present invention. Table 4 below shows initial values of main characteristics of the light-emitting element 2 at a luminance of about 1000 cd/m$^2$.

TABLE 4

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 2 | 3.1 | 0.059 | 1.5 | (0.50, 0.49) | 890 | 60 | 61 | 22 |

The above results show that the light-emitting element 2 fabricated in this example has high external quantum efficiency, which means its high emission efficiency.

Figure 23:
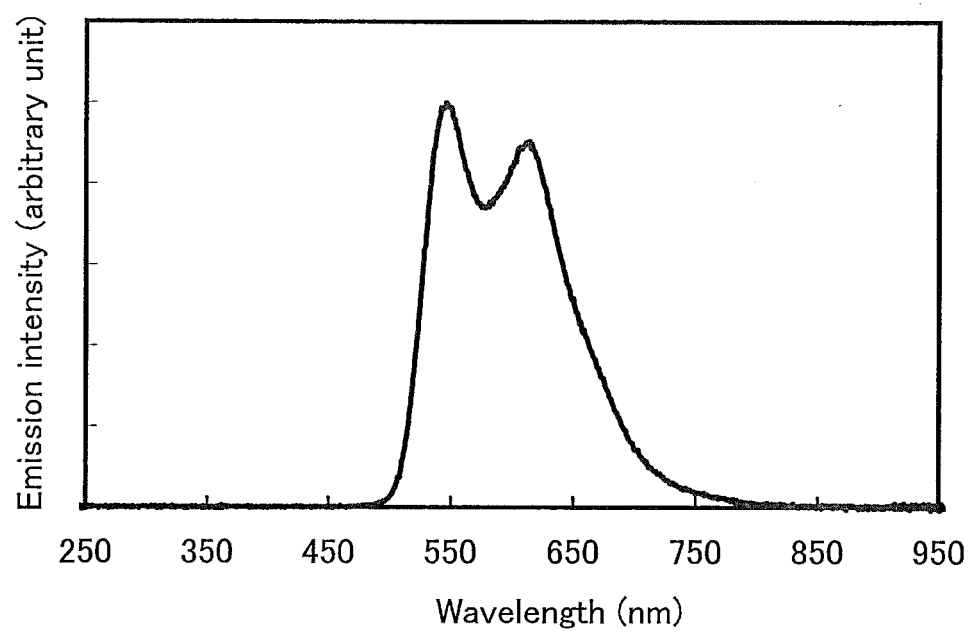
FIG. 23 shows an emission spectrum of the light-emitting element 2.

FIG. 23 shows an emission spectrum when a current at a current density of 25 mA/cm$^2$ was supplied to the light-emitting element 2. FIG. 23 shows that the emission spectrum of the light-emitting element 2 has peaks at around 550 nm and 617 nm, which indicates that the peaks are derived from emission from the phosphorescent organometallic iridium complexes [Ir(tBuppm)$_2$(acac)] (abbreviation) and [Ir(tppr)$_2$(dpm)] (abbreviation).

Figure 24:
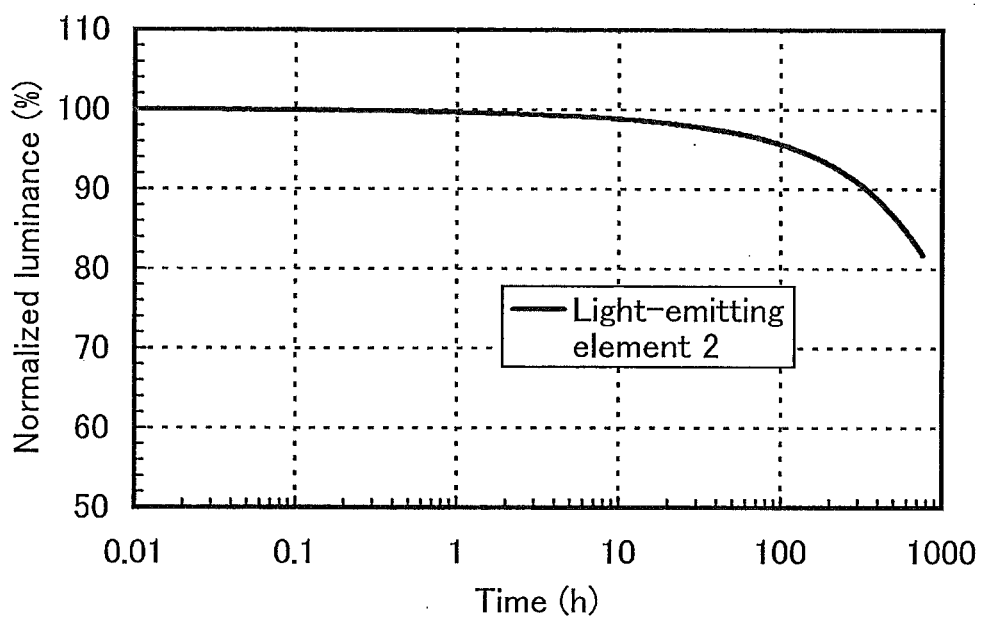
FIG. 24 shows reliability of the light-emitting element 2.

FIG. 24 shows results of a reliability test of the light-emitting element 2. In FIG. 24, the vertical axis represents normalized luminance (%) with an initial luminance of 100%, and the horizontal axis represents driving time (h) of the element. Note that in the reliability test, the light-emitting element 2 was driven under the conditions where the initial luminance was set to 5000 cd/m$^2$ and the current density was constant. As a result, the light-emitting element 2 kept about 97% of the initial luminance after 48 hours elapsed.

Thus, the reliability test revealed that the light-emitting element 2 has high reliability and a long lifetime.

Note that the combination of 2mDBTBPDBq-II (abbreviation) and PCBNBB (abbreviation) forms an exciplex, as described in Example 1.

EXAMPLE 3

Figure 25:
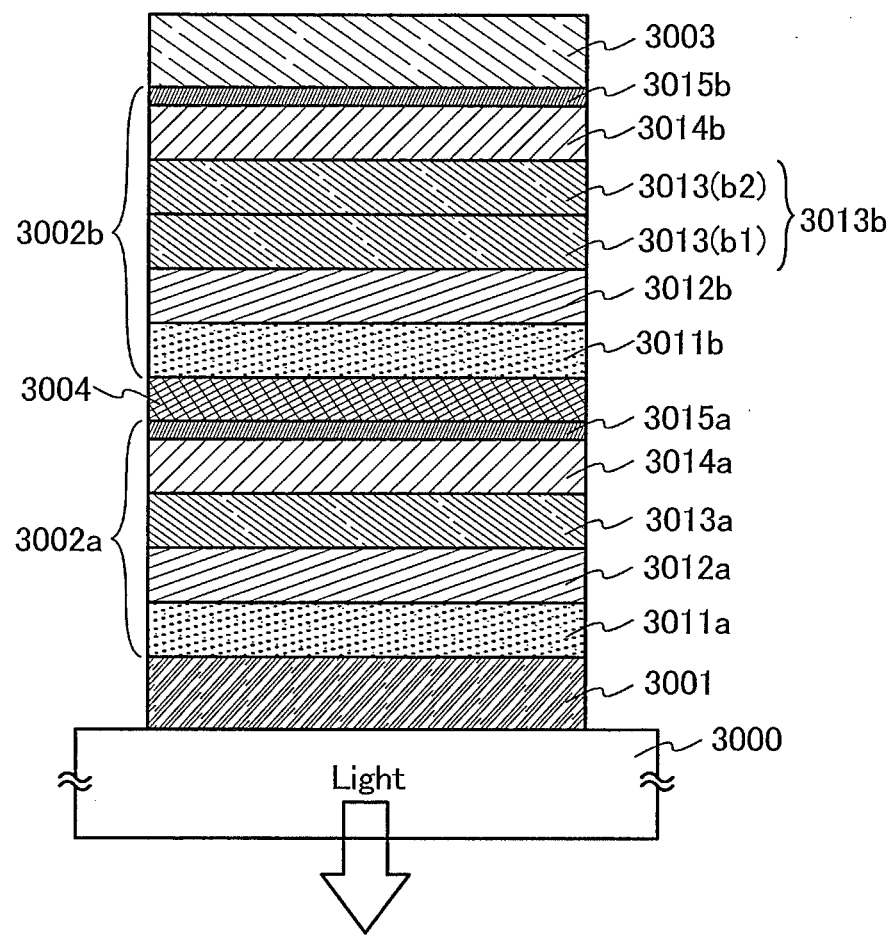
FIG. 25 illustrates a structure of a light-emitting element 3.

In this example, a light-emitting element 3 illustrated in FIG. 25 was fabricated, and its operation characteristics and reliability were measured. Note that the light-emitting element 3 fabricated in this example is a light-emitting element (hereinafter referred to as tandem light-emitting element) in which a charge generation layer is provided between a plurality of EL layers as described in Embodiment 3. Chemical formulae of materials used in this example are shown below.

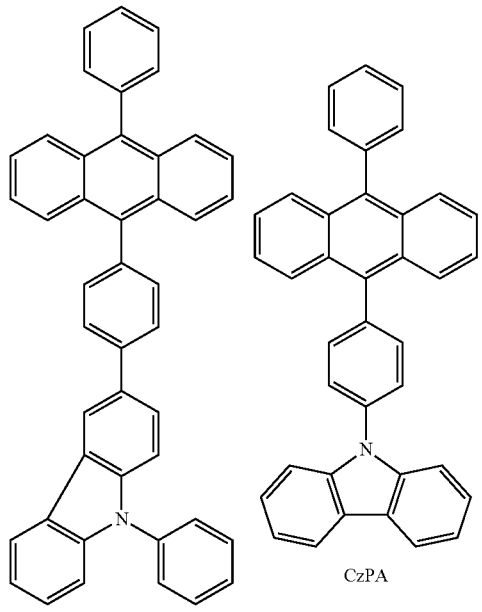

PCzPA

CzPA

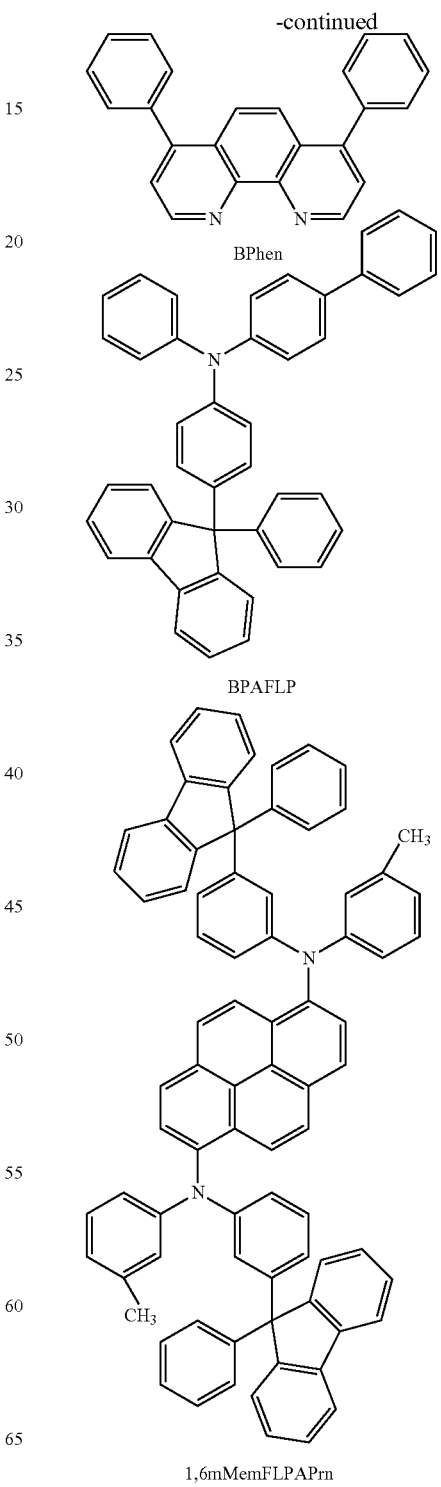

BPhen

BPAFLP 1,6mMemFLPAPrn

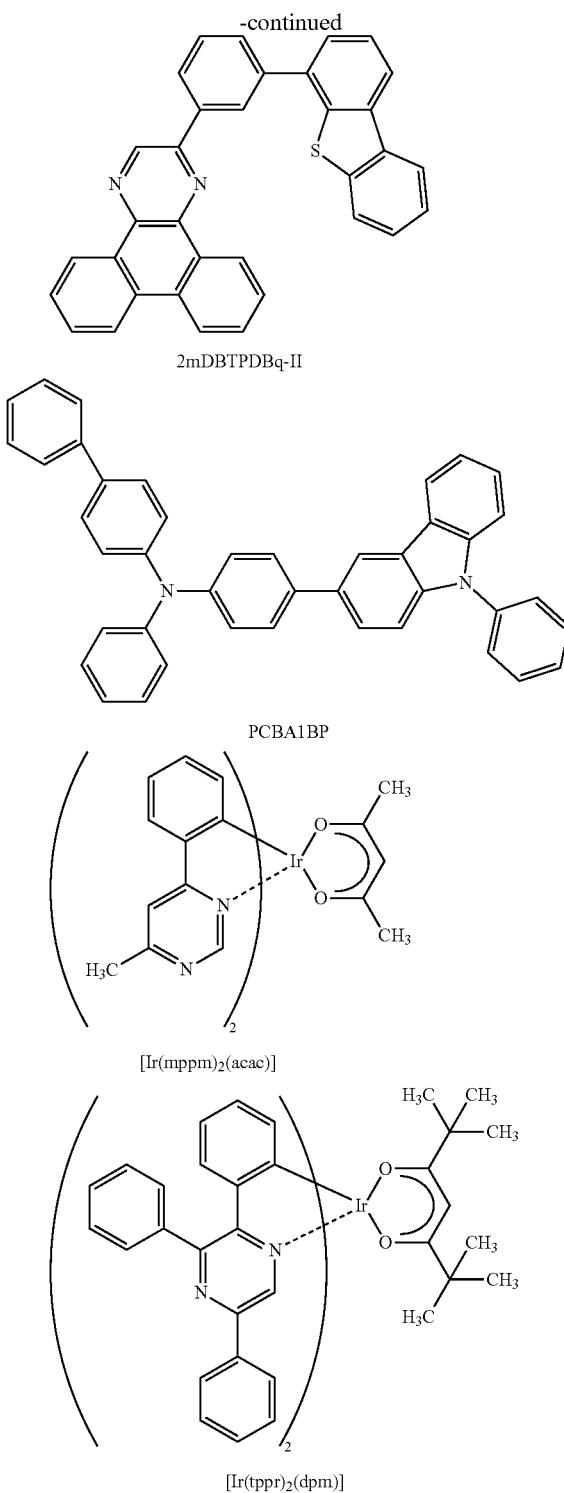

2mDBTPDBq-II

PCBA1BP

[Ir(mppm)₂(acac)]

[Ir(tppr)₂(dpm)]

《Fabrication of Light-emitting Element 3》

First, a film of indium tin oxide containing silicon oxide (ITSO) was formed over a glass substrate 3000 by a sputtering method, so that a first electrode 3001 functioning as an anode was formed. Note that the thickness was set to 110 nm and the electrode area was set to 2 mm×2 mm.

Next, as pretreatment for forming the light-emitting element 3 over the substrate 3000, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 3000 was cooled down for about 30 minutes.

Next, the substrate 3000 was fixed to a holder in the vacuum evaporation apparatus so that a surface on which the first electrode 3001 was provided faced downward. In this example, a case is described in which a first hole-injection layer 3011a, a first hole-transport layer 3012a, a light-emitting layer (A) 3013a, a first electron-transport layer 3014a, and a first electron-injection layer 3015a which are included in a first EL layer 3002a are sequentially formed, a charge generation layer 3004 is formed, and then a second hole-injection layer 3011b, a second hole-transport layer 3012b, a light-emitting layer (B) 3013b, a second electron-transport layer 3014b, and a second electron-injection layer 3015b which are included in a second EL layer 3002b are formed by a vacuum evaporation method.

The pressure in the vacuum evaporation apparatus was reduced to about $10^{-4}$ Pa. Then, 9-[4-(9-phenylcarbazol-3-yl)]phenyl-10-phenylanthracene (abbreviation: PCzPA) and molybdenum(VI) oxide were co-evaporated with a mass ratio of PCzPA (abbreviation) to molybdenum oxide being 1:0.5, whereby the first hole-injection layer 3011a was formed over the first electrode 3001. The thickness of the first hole-injection layer 3011a was set to 60 nm. Note that co-evaporation is an evaporation method by which a plurality of different substances is concurrently vaporized from respective different evaporation sources.

Next, the first hole-transport layer 3012a was formed by evaporation of PCzPA (abbreviation) to a thickness of 30 nm.

Next, the light-emitting layer (A) 3013a was formed over the first hole-transport layer 3012a. The light-emitting layer (A) 3013a was formed by co-evaporation of 9-[4-(10-phenyl-9-anthracenyl)phenyl]-9H-carbazole (abbreviation: CzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) with a mass ratio of CzPA (abbreviation) to 1,6mMemFLPAPrn (abbreviation) being 1:0.05. The thickness of the light-emitting layer (A) 3013a was set to 30 nm.

Next, over the light-emitting layer (A) 3013a, the first electron-transport layer 3014a was formed in such a manner that a film of CzPA (abbreviation) was formed by evaporation to a thickness of 5 nm and then a film of bathophenanthroline (abbreviation: BPhen) was formed by evaporation to a thickness of 15 nm. Further, over the first electron-transport layer 3014a, a film of lithium oxide ($Li_2O$) was formed by evaporation to a thickness of 0.1 nm to form the first electron-injection layer 3015a.

Then, copper phthalocyanine (abbreviation: CuPc) was evaporated to a thickness of 2 nm over the first electron-injection layer 3015a, whereby the charge generation layer 3004 was formed.

Then, 4-phenyl-4'-(9-phenylfluoren-9-yl)triphenylamine (abbreviation: BPAFLP) and molybdenum(VI) oxide were co-evaporated with a mass ratio of BPAFLP (abbreviation) to molybdenum oxide being 1:0.5, whereby the second hole-injection layer 3011b was formed over the charge generation layer 3004. The thickness of the second hole-injection layer 3011b was set to 40 nm.

Next, the second hole-transport layer 3012b was formed by evaporation of BPAFLP (abbreviation) to a thickness of 20 nm.

Next, the light-emitting layer (B) 3013b was formed over the second hole-transport layer 3012b. The light-emitting layer (B) 3013b having a stacked-layer structure was formed by forming a first light-emitting layer 3013(b1) with a thickness of 20 nm by co-evaporation of 2-[3-(dibenzothiophen-4-yl)phenyl]dibenzo[f,h]quinoxaline (abbreviation: 2mDBTPDBq-II), 4-phenyl-4'-(9-phenyl-9H-carbazol-3-yl)triphenylamine (abbreviation: PCBA1BP), and (acetylacetonato)bis(6-methyl-4-phenylpyrimidinato)iridium(III) (abbreviation: [Ir(mppm)$_2$(acac)]) with a mass ratio of 2mDBTPDBq-II (abbreviation) to PCBA1BP (abbreviation) and [Ir(mppm)$_2$(acac)] (abbreviation) being 0.8:0.2:0.06, and then forming a second light-emitting layer 3013(b2) with a thickness of 20 nm by co-evaporation of 2mDBTPDBq-II (abbreviation) and bis(2,3,5-triphenylpyradinato)(dipivaloylmethanato)iridium(III) (abbreviation: [Ir(tppr)$_2$(dpm)]) with a mass ratio of 2mDBTPDBq-II (abbreviation) to [Ir(tppr)$_2$(dpm)] (abbreviation) being 1:0.02.

Next, over the light-emitting layer (B) 3013b, the second electron-transport layer 3014b was formed in such a manner that a film of 2mDBTPDBq-II (abbreviation) was formed by evaporation to a thickness of 15 nm and then a film of BPhen (abbreviation) was formed by evaporation to a thickness of 15 nm. Further, over the second electron-transport layer 3014b, a film of lithium fluoride (LiF) was formed by evaporation to a thickness of 1 nm, whereby the second electron-injection layer 3015b was formed.

Lastly, over the second electron-injection layer 3015b, an aluminum film was formed by evaporation to a thickness of 200 nm as a second electrode 3003 functioning as a cathode. Thus, the light-emitting element 3 was fabricated. Note that, in all the above evaporation steps, evaporation was performed by a resistance-heating method.

Table 5 shows an element structure of the light-emitting element 3 obtained as described above.

The fabricated light-emitting element 3 was sealed in a glove box containing a nitrogen atmosphere so as not to be exposed to air (specifically, a sealant was applied to an outer edge of the element and heat treatment was performed at 80° C. for 1 hour at the time of sealing).

《Operation Characteristics of Light-emitting Element 3》

Operation characteristics of the fabricated light-emitting element 3 were measured. Note that the measurements were carried out at room temperature (in an atmosphere kept at 25° C.).

Figure 26:
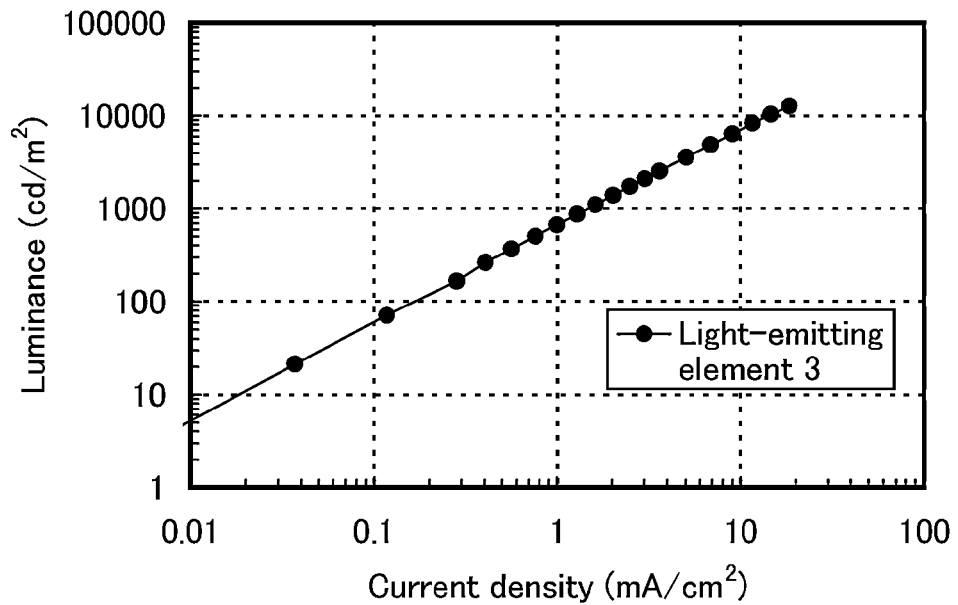
FIG. 26 shows current density-luminance characteristics of the light-emitting element 3.
Figure 27:
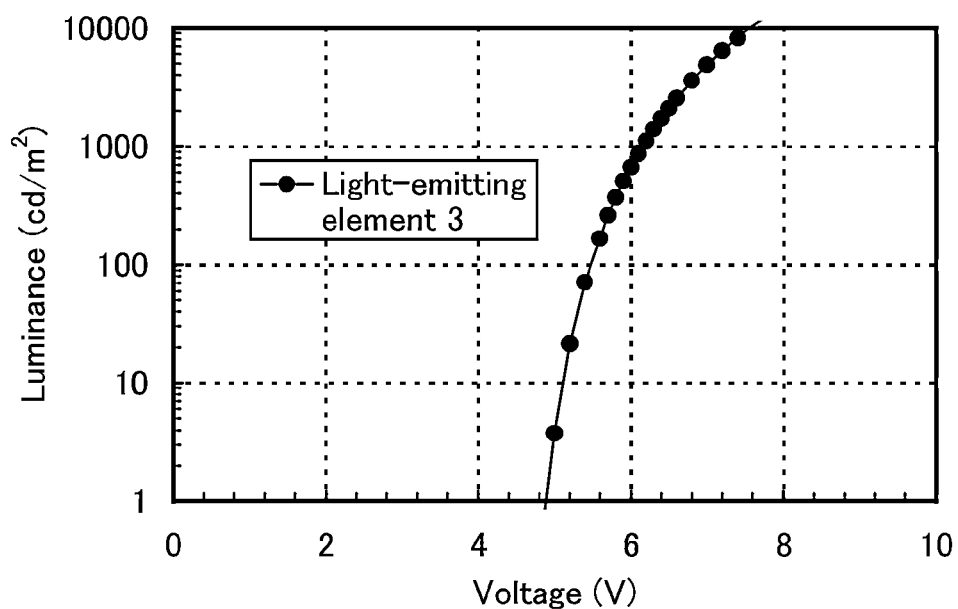
FIG. 27 shows voltage-luminance characteristics of the light-emitting element 3.
Figure 28:
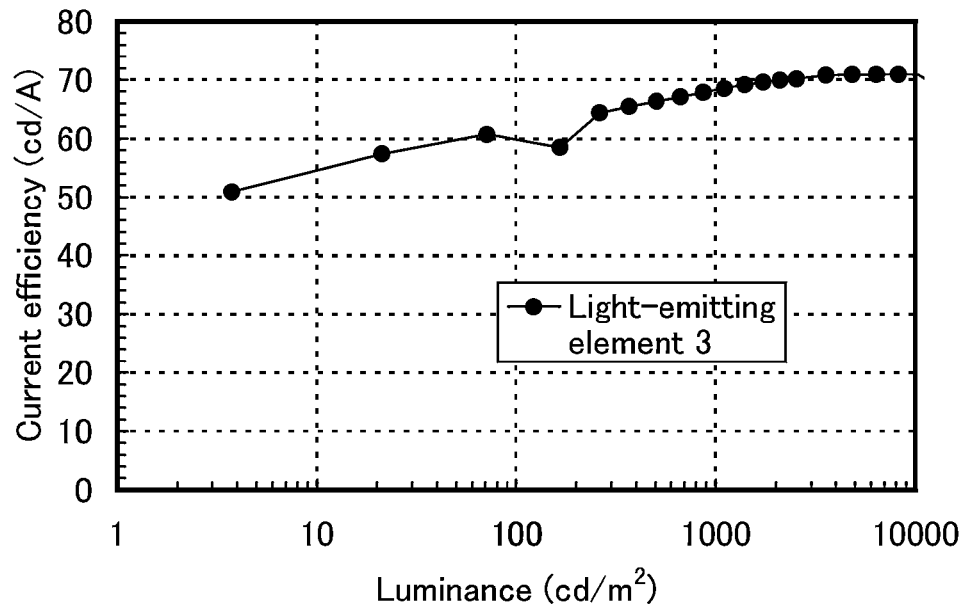
FIG. 28 shows luminance-current efficiency characteristics of the light-emitting element 3.
Figure 29:
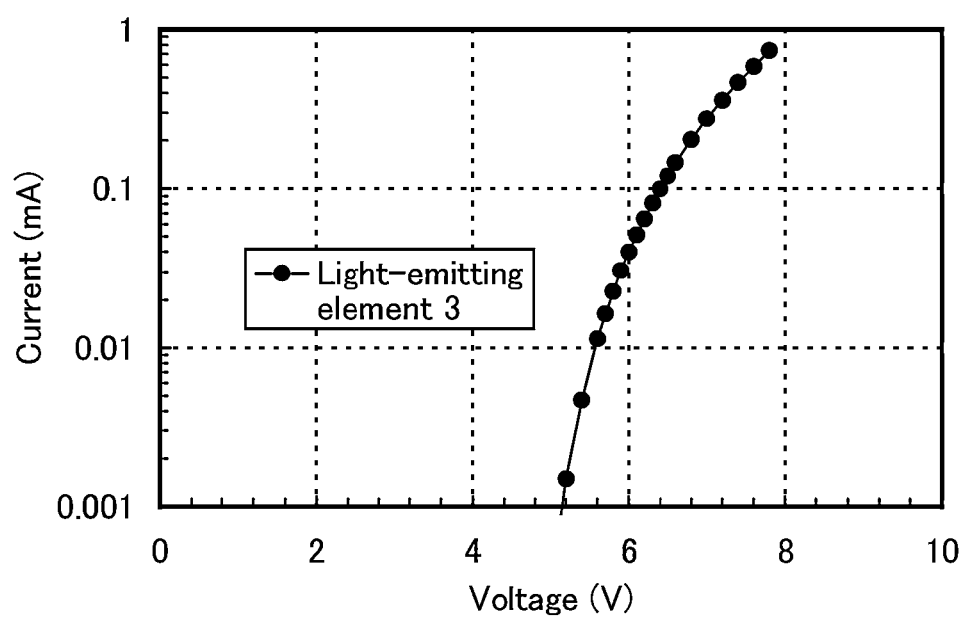
FIG. 29 shows voltage-current characteristics of the light-emitting element 3.

First, FIG. 26 shows current density-luminance characteristics of the light-emitting element 3. In FIG. 26, the vertical axis represents luminance (cd/m$^2$), and the horizontal axis represents current density (mA/cm$^2$). FIG. 27 shows voltage-luminance characteristics of the light-emitting element 3. In FIG. 27, the vertical axis represents luminance (cd/m$^2$), and the horizontal axis represents voltage (V). FIG. 28 shows luminance-current efficiency characteristics of the light-emitting element 3. In FIG. 28, the vertical axis represents current efficiency (cd/A), and the horizontal axis represents luminance (cd/m$^2$). FIG. 29 shows voltage-current characteristics of the light-emitting element 3. In FIG. 29, the vertical axis represents current (mA), and the horizontal axis represents voltage (V).

FIG. 28 reveals high efficiency of the light-emitting element 3 that is one embodiment of the present invention. Table 6 below shows initial values of main characteristics of the light-emitting element 3 at a luminance of about 1000 cd/m$^2$.

TABLE 5

| | First electrode | First hole-injection layer | First hole-transport layer | Light-emitting layer (A) | First eletron-transport layer | First electron-injection layer | Charge generation layer |
|---|---|---|---|---|---|---|---|
| Light-emitting element 3 | ITSO (110 nm) | PCzPA:MoOx (1:0.5, 60 nm) | PCzPA (30 nm) | CzPA:1,6mMemFLPAPrn (1:0.05, 30 nm) | CzPA (5 nm) BPhen (15 nm) | Li$_2$O (0.1 nm) | CuPc (2 nm) |

| | Second hole-injection layer | Second hole-transport layer | Light-emitting layer (B) | Second electron-transport layer | Second electron-injection layer | Second electrode |
|---|---|---|---|---|---|---|
| Light-emitting element 3 | BPAFLP:MoOx (1:0.5, 40 nm) | BPAFLP (20 nm) | * | 2mDBTPDBq-II (15 nm) BPhen (15 nm) | LiF (1 nm) | Al (200 nm) |

* 2mDBTPDBq-II:PCBA1BP:[Ir mppm)$_2$(acac)] (0.8:0.2:0.06, 20 nm)\2mDBTPDBq-II:[Ir(tppr)$_2$(dpm)] (1:0.02, 20 nm)

TABLE 6

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 3 | 6.2 | 0.065 | 1.6 | (0.37, 0.37) | 1100 | 69 | 35 | 29 |

The above results show that the light-emitting element 3 fabricated in this example has high external quantum efficiency, which means its high emission efficiency.

Figure 30:
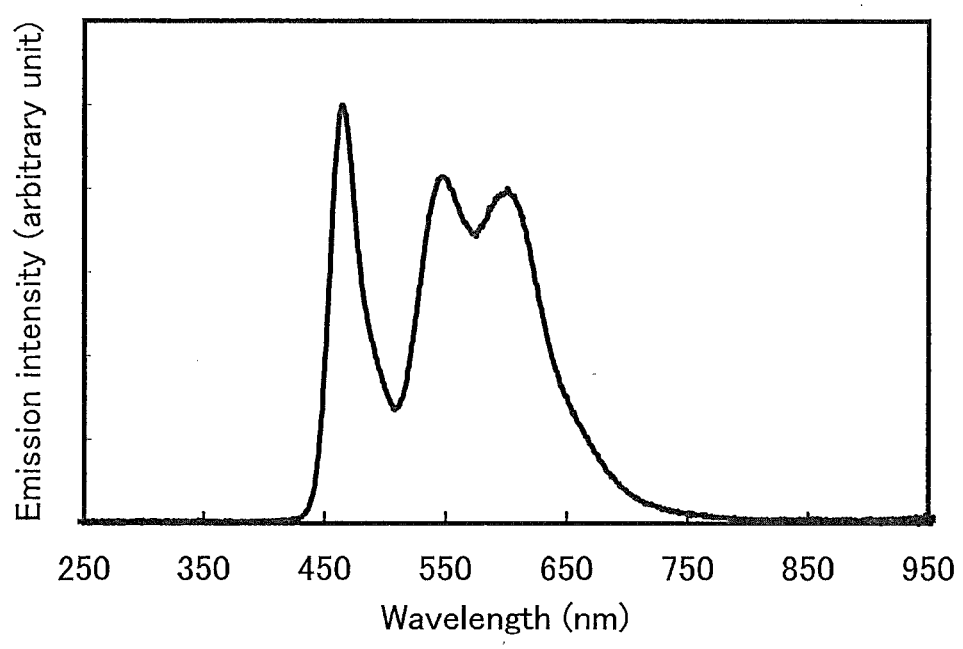
FIG. 30 shows an emission spectrum of the light-emitting element 3.

FIG. 30 shows an emission spectrum when a current at a current density of 25 mA/cm$^2$ was supplied to the light-emitting element 3. FIG. 30 shows that the emission spectrum of the light-emitting element 3 has peaks at around 465 nm, 552 nm, and 604 nm, which indicates that the peaks are derived from emission from the phosphorescent organometallic iridium complexes contained in the light-emitting layers.

Note that a film of 2mDBTPDBq-II (abbreviation), a film of PCBA1BP (abbreviation), and a mixed film of 2mDBTP-DBq-II (abbreviation) and PCBA1BP (abbreviation) were manufactured, and photoluminescence (PL) of each of the films was measured. The results are that the photoluminescence (PL) peak wavelength of the evaporation film of 2mDBTPDBq-II (abbreviation) was 426 nm and the PL peak wavelength of the evaporation film of PCBA1BP (abbreviation) was 416 nm, whereas the PL peak wavelength of the mixed film formed by co-evaporation of these substances was 519 nm and significantly shifted to a longer wavelength side. Thus, it can be seen that the combination of 2mDBTPDBq-II (abbreviation) and PCBA1BP (abbreviation) forms an exciplex.

EXAMPLE 4

Figure 31:
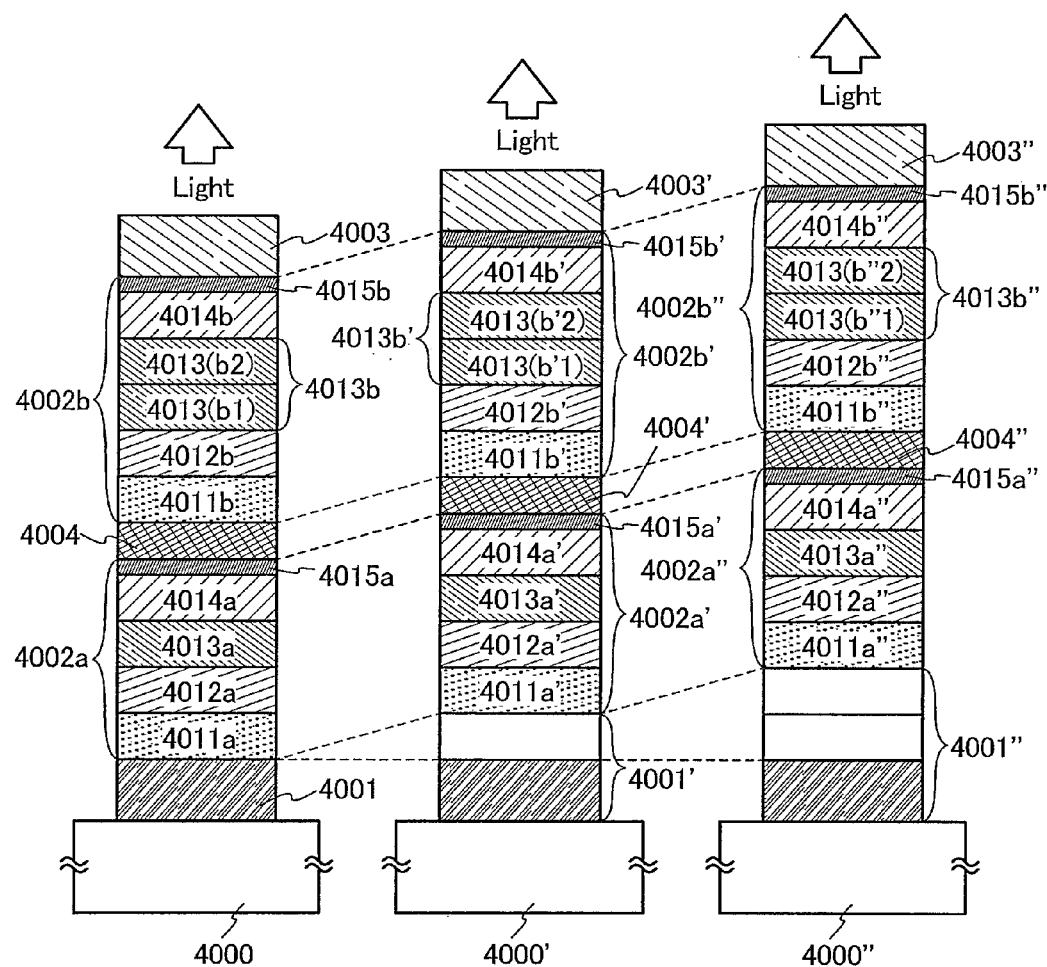
FIGS. 31A to 31C illustrate structures of light-emitting elements 4 to 6.

In this example, light-emitting elements 4 to 6 illustrated in FIGS. 31A to 31C (FIG. 31A illustrates the light-emitting element 4, FIG. 31B illustrates the light-emitting element 5, and FIG. 31C illustrates the light-emitting element 6) were fabricated, and their operation characteristics and reliabilities were measured. Note that when the light-emitting elements 4 to 6 fabricated in this example are formed over the same substrate, a structure can be obtained in which the structure where a charge generation layer is provided between a plurality of EL layers as described in Embodiment 3 is combined with the micro optical resonator (microcavity) structure described in Embodiment 4. Chemical formulae of materials used in this example are shown below.

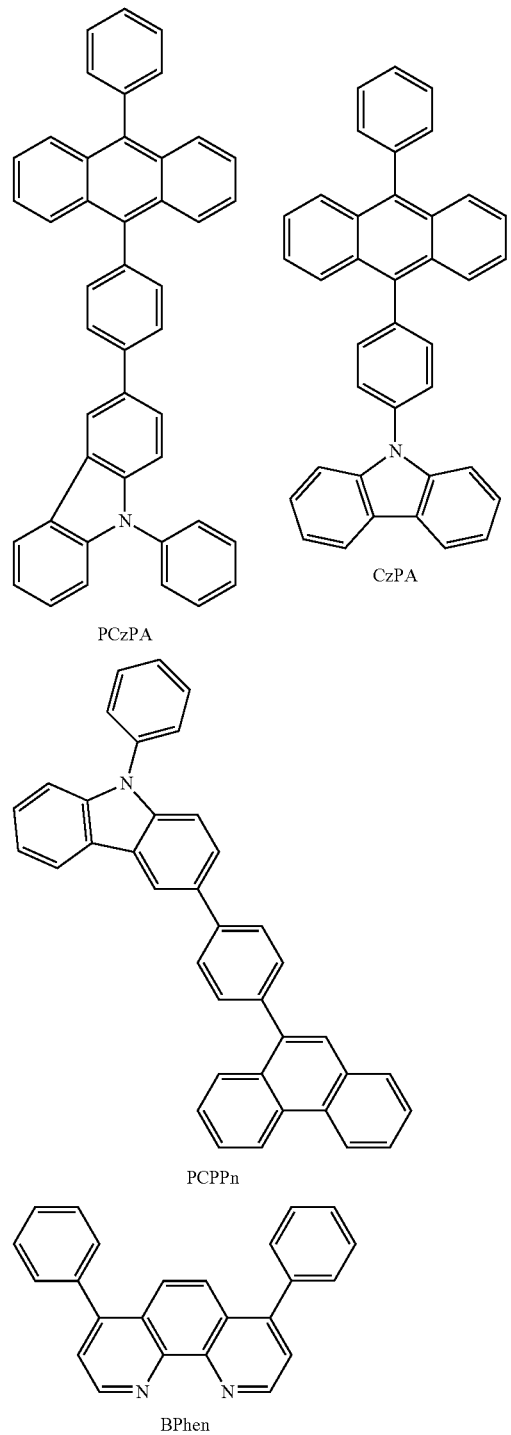

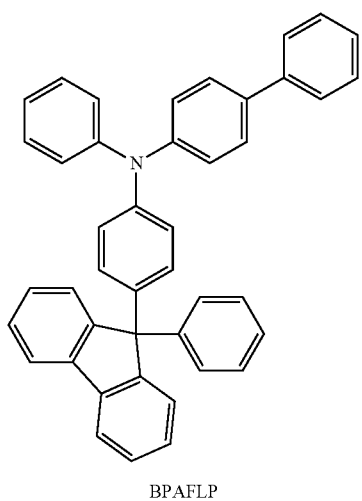
BPAFLP
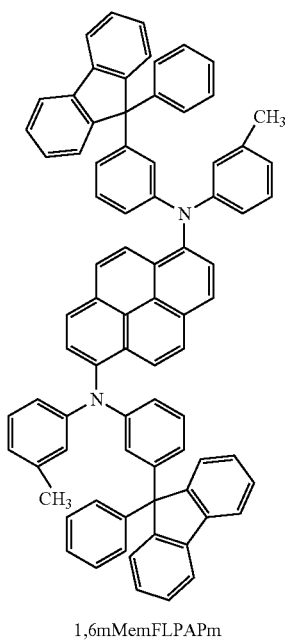
1,6mMemFLPAPm
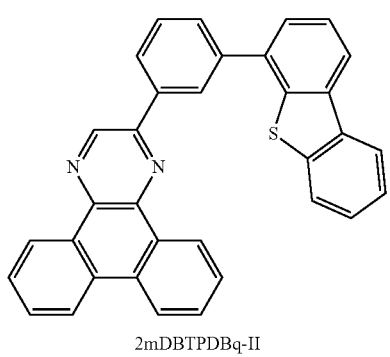
2mDBTPDBq-II
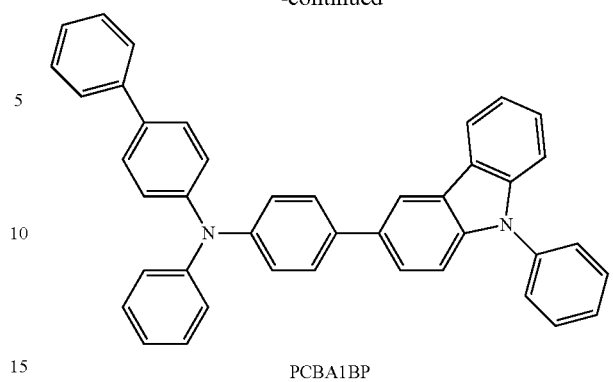
PCBA1BP
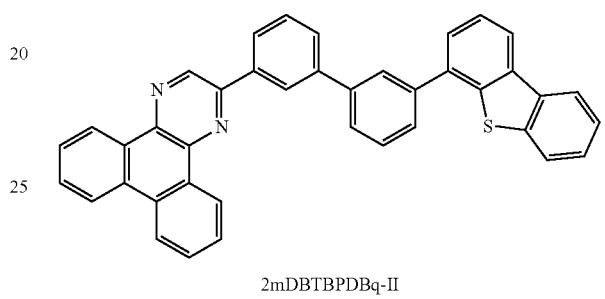
2mDBTBPDBq-II
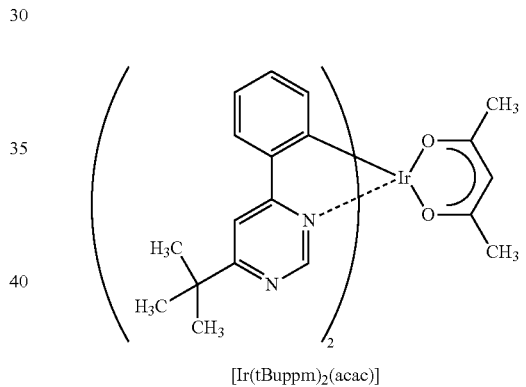
[Ir(tBuppm)$_2$(acac)]
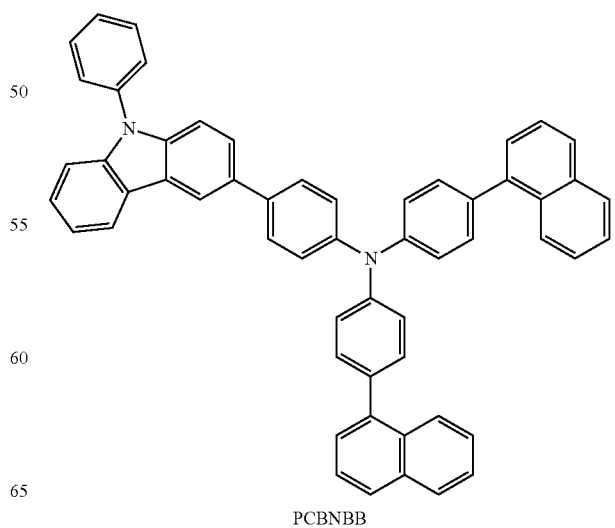
PCBNBB

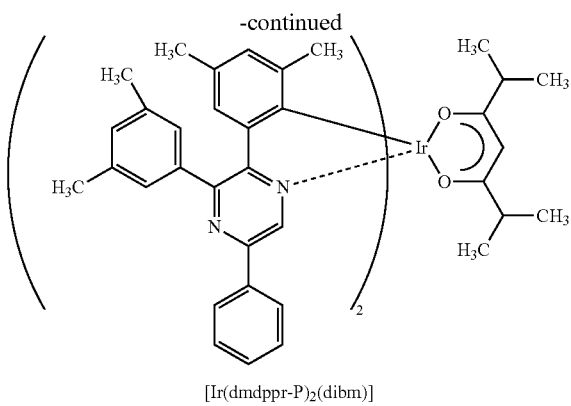

[Ir(dmdppr-P)₂(dibm)]

《Fabrication of Light-emitting Elements 4 to 6》

The only difference between the light-emitting elements 4 to 6 in this example is the structures of a first electrode and a coloring layer; therefore, the other components will be collectively described.

First, over each glass substrate (4000, 4000', 4000''), a film of an aluminum (Al) and titanium (Ti) alloy (Al—Ti) with a thickness of 200 nm was formed by a sputtering method, and then a film of Ti with a thickness of 6 nm was formed by a sputtering method. Accordingly, a first electrode 4001 functioning as an anode of the light-emitting element 4 was formed. Note that a first electrode 4001' functioning as an anode of the light-emitting element 5 was formed by further forming a film of indium tin oxide containing silicon oxide (ITSO) with a thickness of 40 nm by a sputtering method over the film of Ti. A first electrode 4001" functioning as an anode of the light-emitting element 6 was formed by further forming a film of indium tin oxide containing silicon oxide (ITSO) with a thickness of 80 nm by a sputtering method over the film of Ti. At this time, the films of Ti are partially or entirely oxidized and contain titanium oxide. Note that the electrode area was set to 2 mm×2 mm.

Next, as pretreatment, UV ozone treatment was performed on the first electrodes (4001, 4001', 4001") of the light-emitting elements 4 to 6, which were formed over the respective substrates (4000, 4000', 4000"), for 370 seconds after washing of surfaces of the substrates with water and baking that was performed at 200° C. for one hour.

After that, the substrates were transferred into a vacuum evaporation apparatus where the pressure had been reduced to approximately $10^{-4}$ Pa, and were subjected to vacuum baking at 170° C. for 30 minutes in a heating chamber of the vacuum evaporation apparatus, and then the substrates (4000, 4000', 4000") were cooled down for about 30 minutes.

Next, the substrates (4000, 4000', 4000") were fixed to holders in the vacuum evaporation apparatus so that surfaces on which the first electrodes (4001, 4001', 4001") were provided faced downward. In this example, a case is described in which first hole-injection layers (4011a, 4011a', 4011a"), first hole-transport layers (4012a, 4012a', 4012a"), light-emitting layers (A) (4013a, 4013a', 4013a"), first electron-transport layers (4014a, 4014a', 4014a"), and first electron-injection layers (4015a, 4015a', 4015a") which are included in first EL layers (4002a, 4002a', 4002a") are sequentially formed, charge generation layers (4004, 4004', 4004") are formed, and then second hole-injection layers (4011b, 4011b', 4011b"), second hole-transport layers (4012b, 4012b', 4012b"), light-emitting layers (B) (4013b, 4013b', 4013b"), second electron-transport layers (4014b, 4014b', 4014b"), and second electron-injection layers (4015b, 4015b', 4015b") which are included in second EL layers (4002b, 4002b', 4002b") are formed, by a vacuum evaporation method.

The pressure in the vacuum evaporation apparatus was reduced to about $10^{-4}$ Pa. Then, 9-[4-(9-phenylcarbazol-3-yl)]phenyl-10-phenylanthracene (abbreviation: PCzPA) and molybdenum(VI) oxide were co-evaporated with a mass ratio of PCzPA (abbreviation) to molybdenum oxide being 1:0.5, whereby the first hole-injection layers (4011a, 4011a', 4011a") were formed over the first electrodes (4001, 4001', 4001"). The thickness of each of the first hole-injection layers (4011a, 4011a', 4011a") was set to 13 nm Note that co-evaporation is an evaporation method by which a plurality of different substances is concurrently vaporized from respective different evaporation sources.

Next, the first hole-transport layers (4012a, 4012a', 4012a") were each formed by evaporation of 9-{4-(9-H-9-phenylcarbazol-3-yl)-phenylyl}-phenanthrene (abbreviation: PCPPn) to a thickness of 20 nm.

Next, the light-emitting layers (A) (4013a, 4013a', 4013a") were formed over the first hole-transport layers (4012a, 4012a', 4012a"). The light-emitting layers (A) (4013a, 4013a', 4013a") were each formed by co-evaporation of 9-[4-(10-phenyl-9-anthracenyl)phenyl]-9H-carbazole (abbreviation: CzPA) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) with a mass ratio of CzPA (abbreviation) to 1,6mMemFLPAPrn (abbreviation) being 1:0.05. The thickness of each of the light-emitting layers (A) (4013a, 4013a', 4013a") was set to 30 nm.

Next, over the light-emitting layers (A) (4013a, 4013a', 4013a"), the first electron-transport layers (4014a, 4014a', 4014a") were formed in such a manner that a film of CzPA (abbreviation) was formed by evaporation to a thickness of 5 nm and then a film of bathophenanthroline (abbreviation: BPhen) was formed by evaporation to a thickness of 15 nm. Further, over the first electron-transport layers (4014a, 4014a', 4014a"), films of lithium oxide (Li₂O) were formed by evaporation to a thickness of 0.1 nm to form the first electron-injection layers (4015a, 4015a', 4015a").

Then, copper phthalocyanine (abbreviation: CuPc) was evaporated to a thickness of 2 nm over the first electron-injection layers (4015a, 4015a', 4015a"), whereby the charge generation layers (4004, 4004', 4004") were formed.

Then, PCzPA (abbreviation) and molybdenum(VI) oxide were co-evaporated with a mass ratio of PCzPA (abbreviation) to molybdenum oxide being 1:0.5, whereby the second hole-injection layers (4011b, 4011b', 4011b") were formed over the charge generation layers (4004, 4004', 4004"). The thickness of each of the second hole-injection layers (4011b, 4011b', 4011b") was set to 13 nm.

Next, the second hole-transport layers (4012b, 4012b', 4012b") were each formed by evaporation of BPAFLP (abbreviation) to a thickness of 20 nm.

Next, the light-emitting layers (B) (4013b, 4013b', 4013b") were formed over the second hole-transport layers (4012b, 4012b', 4012b"). The light-emitting layers (B) (4013b, 4013b', 4013b") having a stacked-layer structure were formed by forming first light-emitting layers (4013(b1), 4013(b'1), 4013(b"1)) each with a thickness of 20 nm by co-evaporation of 2-[3'-(dibenzothiophen-4-yl)biphenyl-3-yl]dibenzo[f,h]quinoxaline (abbreviation: 2mDBTBPDBq-II), 4,4'-di(1-naphthyl)-4"-(9-phenyl-9H-carbazol-3-yl)triphenylamine (abbreviation: PCBNBB), and (acetylacetonato)bis(6-tert-butyl-4-phenylpyrimidinato)iridium(III) (abbreviation: [Ir(tBuppm)₂(acac)]) with a mass ratio of 2mDBTBPDBq-II (abbreviation) to PCBNBB (abbreviation)

and [Ir(tBuppm)₂(acac)] (abbreviation) being 0.8:0.2:0.06, and then forming second light-emitting layers (4013(*b*2), 4013(*b*'2), 4013(*b*"2)) each with a thickness of 20 nm by co-evaporation of 2mDBTBPDBq-II (abbreviation) and bis{4,6-dimethyl-2-[3-(3,5-dimethylphenyl)-5-phenyl-2-pyrazinyl-κN]phenyl-κC}(2,6-dimethyl-3,5-heptanedionato-κ²O,O')iridium(III) (abbreviation: [Ir(dmdppr-P)₂(dibm)]) with a mass ratio of 2mDBTBPDBq-II (abbreviation) to [Ir(dmdppr-P)₂(dibm)] (abbreviation) being 1:0.02.

Next, over the light-emitting layers (B) (4013*b*, 4013*b*', 4013*b*"), the second electron-transport layers (4014*b*, 4014*b*', 4014*b*") were formed in such a manner that a film of 2mDBT-BPDBq-II (abbreviation) was formed by evaporation to a thickness of 15 nm and then a film of BPhen (abbreviation) was formed by evaporation to a thickness of 15 nm. Further, over the second electron-transport layers (4014*b*, 4014*b*', 4014*b*"), films of lithium fluoride (LiF) were formed by evaporation to a thickness of 1 nm, whereby the second electron-injection layers (4015*b*, 4015*b*', 4015*b*") were formed.

Lastly, second electrodes (4003, 4003', 4003") functioning as cathodes were formed by forming films of an Ag—Mg alloy each with a thickness of 15 nm over the second electron-injection layers (4015*b*, 4015*b*', 4015*b*") and then forming films of indium tin oxide (ITO) each with a thickness of 70 nm by a sputtering method. Thus, the light-emitting elements 4 to 6 were fabricated. At this time, the films of the Ag—Mg alloy were each formed by co-evaporation of Ag and Mg in a mass ratio of Ag to Mg of 10:1. Note that, in all the above evaporation steps, evaporation was performed by a resistance-heating method.

Table 7 shows element structures of the light-emitting elements 4 to 6 obtained as described above.

Note that as shown in Table 7, a counter substrate for the light-emitting element 4 is provided with a blue coloring layer (B); a counter substrate for the light-emitting element 5 is provided with a green coloring layer (G); and a counter substrate for the light-emitting element 6 is provided with a red coloring layer (R). The light-emitting elements 4 to 6 fabricated as described above were sealed by being attached to these counter substrates in a glove box containing a nitrogen atmosphere so as not to be exposed to air (specifically, a sealant was applied to an outer edge of each element and heat treatment was performed at 80° C. for 1 hour at the time of sealing).

《Operation Characteristics of Light-emitting Elements 4 to 6》

Operation characteristics of the fabricated light-emitting elements 4 to 6 were measured. Note that the measurements were carried out at room temperature (in an atmosphere kept at 25° C.).

Figure 32:
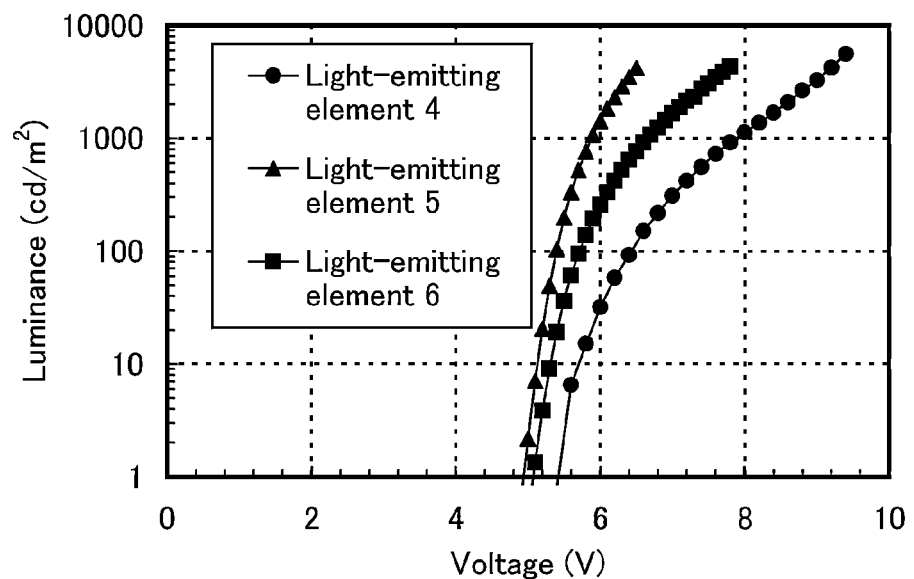
FIG. 32 shows voltage-luminance characteristics of the light-emitting elements 4 to 6.
Figure 33:
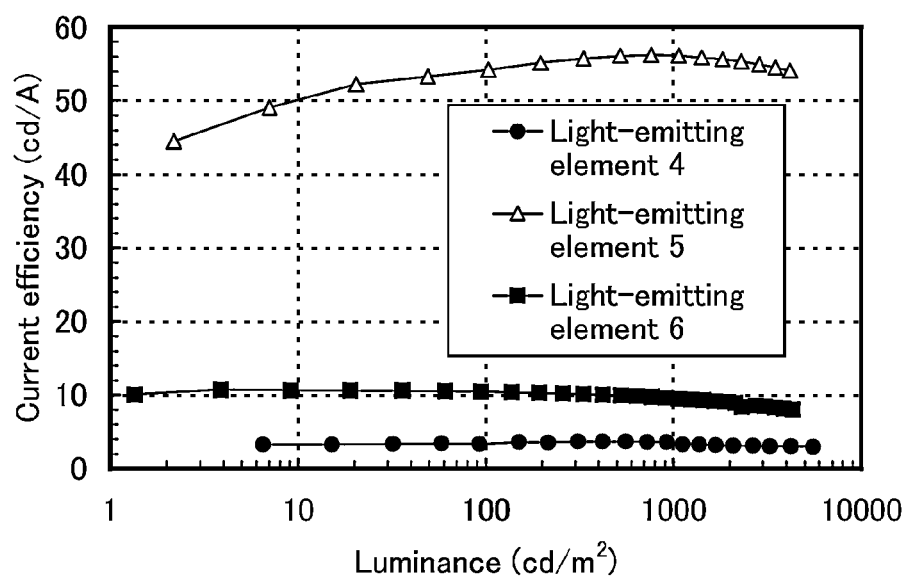
FIG. 33 shows luminance-current efficiency characteristics of the light-emitting elements 4 to 6.
Figure 34:
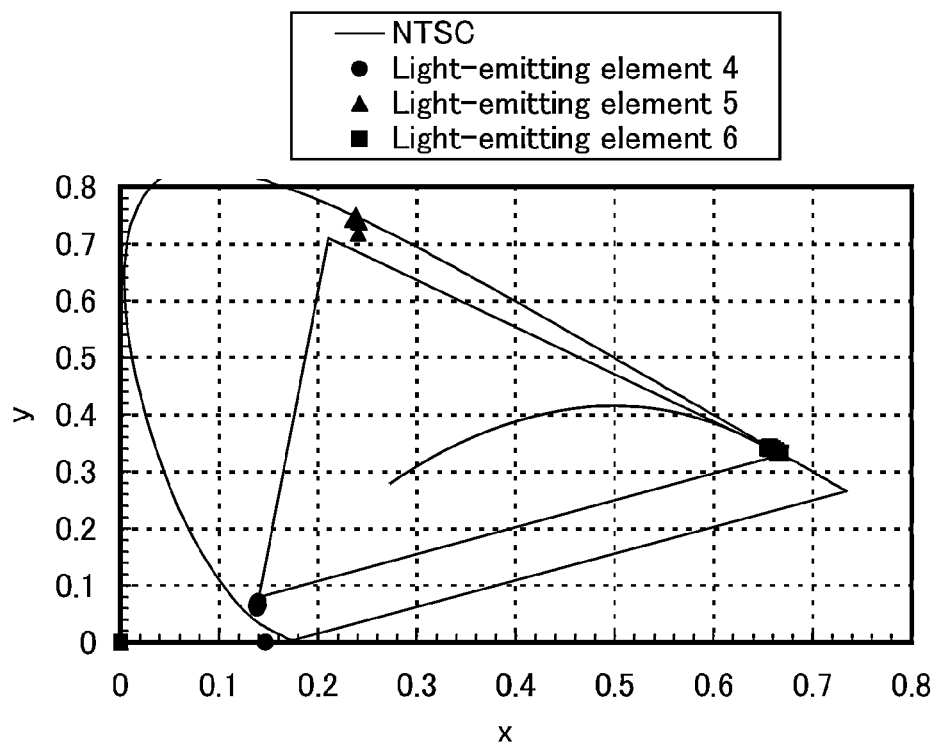
FIG. 34 shows a CIE chromaticity diagram of the light-emitting elements 4 to 6.

First, FIG. 32 shows voltage-luminance characteristics of the light-emitting elements 4 to 6. In FIG. 32, the vertical axis represents luminance (cd/m²), and the horizontal axis represents voltage (V). FIG. 33 shows luminance-current efficiency characteristics of the light-emitting elements 4 to 6. In FIG. 33, the vertical axis represents current efficiency (cd/A), and the horizontal axis represents luminance (cd/m²). FIG. 34 shows a CIE chromaticity diagram of the light-emitting elements 4 to 6. In FIG. 34, the vertical axis represents x-coordinate, and the horizontal axis represents y-coordinate. The solid line in FIG. 34 indicates the color reproduction range defined by the National Television Standards Committee (NTSC).

Table 8 below shows initial values of main characteristics of the light-emitting elements 4 to 6 at a luminance of about 1000 cd/m².

TABLE 7

| | First electrode | | First hole-injection layer | First hole-transport layer | Light-emitting layer (A) | First eletron-transport layer | First electron-injection layer | Charge generation layer |
|---|---|---|---|---|---|---|---|---|
| Light-emitting element 4 | Al—Ti\Ti (200 nm\6 nm) | | PCzPA:MoOx (1:0.5, 13 nm) | PCPPn (20 nm) | CzPA:1,6mMemFLPAPrn (1:0.05, 30 nm) | CzPA (5 nm) | Bphen (15 nm) | Li₂O (0.1 nm) | CuPc (2 nm) |
| Light-emitting element 5 | Al—Ti\Ti (200 nm\6 nm) | ITSO (40 nm) | | | | | | |
| Light-emitting element 6 | Al—Ti\Ti (200 nm\6 nm) | ITSO (80 nm) | | | | | | |

| | Second hole-injection layer | Second hole-transport layer | Light-emitting layer (B) | Second electron-transport layer | | Second electron-injection layer | Second electrode | | CF |
|---|---|---|---|---|---|---|---|---|---|
| Light-emitting element 4 | PCzPA:MoOx (1:0.5, 13 nm) | BPAFLP (20 nm) | * | 2mDBTBPDBq-II (15 nm) | Bphen (15 nm) | LiF (1 nm) | Ag:Mg (1:0.1, 15 nm) | ITO (70 nm) | B |
| Light-emitting element 5 | | | | | | | | | G |
| Light-emitting element 6 | | | | | | | | | R |

* 2mDBTBPDBq-II:PCBNBB:[Ir(tBuppm)₂(acac)] (0.8:0.2:0.06, 20 nm)\2mDBTBPDBq-II:[Ir(dmdppr-P)₂(dibm)] (1:0.02, 20 nm)

TABLE 8

| | Voltage (V) | Current (mA) | Current density (mA/cm$^2$) | Chromaticity (x, y) | Luminance (cd/m$^2$) | Power efficiency (lm/W) |
|---|---|---|---|---|---|---|
| Light-emitting element 4 | 7.8 | 1.000 | 26 | (0.14, 0.07) | 920 | 1.4 |
| Light-emitting element 5 | 5.9 | 0.076 | 1.9 | (0.24, 0.74) | 1100 | 30 |
| Light-emitting element 6 | 6.7 | 0.450 | 11 | (0.66, 0.34) | 1100 | 4.5 |

The above results show that the light-emitting elements 4 to 6 fabricated in this example exhibit light emissions of red (R), green (G), and blue (B), which are distinctly different from each other. Although the light-emitting elements 4 to 6 are formed over separate substrates in this example, they can be formed over the same substrate. The above finding indicates that the light-emitting elements 4 to 6 are suitable for full-color display when formed over the same substrate.

Figure 35:
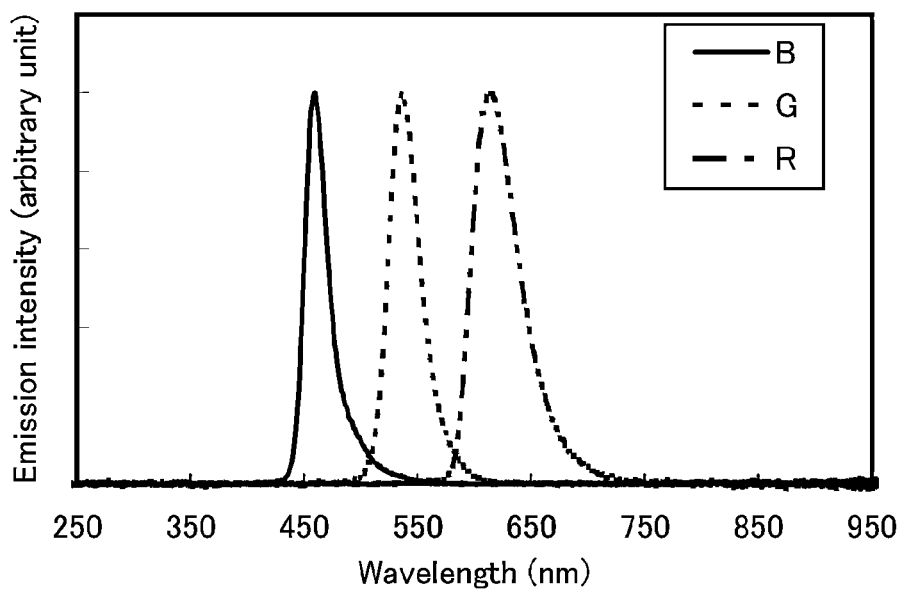
FIG. 35 shows emission spectra of the light-emitting elements 4 to 6.

FIG. 35 shows emission spectra when a current at a current density of 25 mA/cm$^2$ was supplied to the light-emitting elements 4 to 6. FIG. 35 shows that the emission spectrum of the light-emitting element 4 has a peak at around 460 nm, the emission spectrum of the light-emitting element 5 has a peak at around 537 nm, and the emission spectrum of the light-emitting element 6 has a peak at around 617 nm, which indicates that the peaks of the light-emitting elements 5 and 6 are derived from emission from the phosphorescent organometallic iridium complexes contained in the light-emitting layers.

Note that the combination of 2mDBTBPDBq-II (abbreviation) and PCBNBB (abbreviation) forms an exciplex, as described in Example 1.

REFERENCE SYNTHESIS EXAMPLE

In this example, a synthesis method of bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), the organometallic iridium complex used in this example, is described. The structure of [Ir(dmdppr-P)$_2$(dibm)] (abbreviation) is shown below.

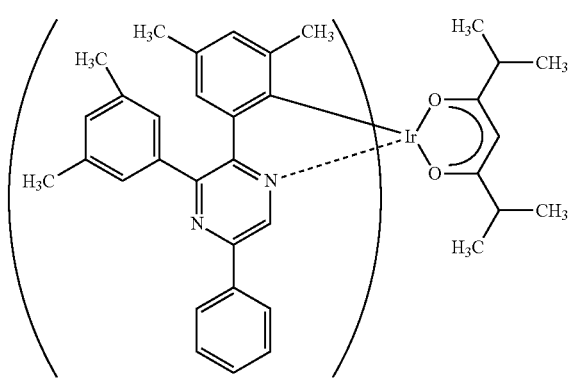

[Ir(dmdppr-P)$_2$(dibm)]

Step 1: Synthesis of 2,3-Bis(3,5-dimethylphenyl)pyrazine (abbreviation: Hdmdppr)

First, 5.00 g of 2,3-dichloropyrazine, 10.23 g of 3,5-dimethylphenylboronic acid, 7.19 g of sodium carbonate, 0.29 g of bis(triphenylphosphine)palladium(II) dichloride (abbreviation: Pd(PPh$_3$)$_2$Cl$_2$), 20 mL of water, and 20 mL of acetonitrile were put into a recovery flask equipped with a reflux pipe, and the air in the flask was replaced with argon. This reaction container was subjected to irradiation with microwaves (2.45 GHz, 100 W) for 60 minutes to be heated. Here, into the flask were further put 2.55 g of 3,5-dimethylphenylboronic acid, 1.80 g of sodium carbonate, 0.070 g of Pd(PPh$_3$)$_2$Cl$_2$, 5 mL of water, and 5 mL of acetonitrile, and irradiation with microwaves (2.45 GHz, 100 W) was performed again for 60 minutes so that heating was performed.

Then, water was added to this solution and the organic layer was extracted with dichloromethane. The obtained organic layer was washed with a saturated aqueous solution of sodium hydrogen carbonate, water, and a saturated aqueous solution of sodium chloride, and was dried with magnesium sulfate. After the drying, the solution was filtered. The solvent of this solution was distilled off, and the obtained residue was purified by flash column chromatography using hexane and ethyl acetate as a developing solvent in a volume ratio of 5:1. The solvent was distilled off, and the obtained solid was purified by flash column chromatography using dichloromethane and ethyl acetate as a developing solvent in a volume ratio of 10:1, so that Hdmdppr (abbreviation), which was the pyrazine derivative to be produced, was obtained as a white powder in a yield of 44%. Note that the irradiation with microwaves was performed using a microwave synthesis system (Discover, manufactured by CEM Corporation). A synthesis scheme of Step 1 is shown in (a-1).

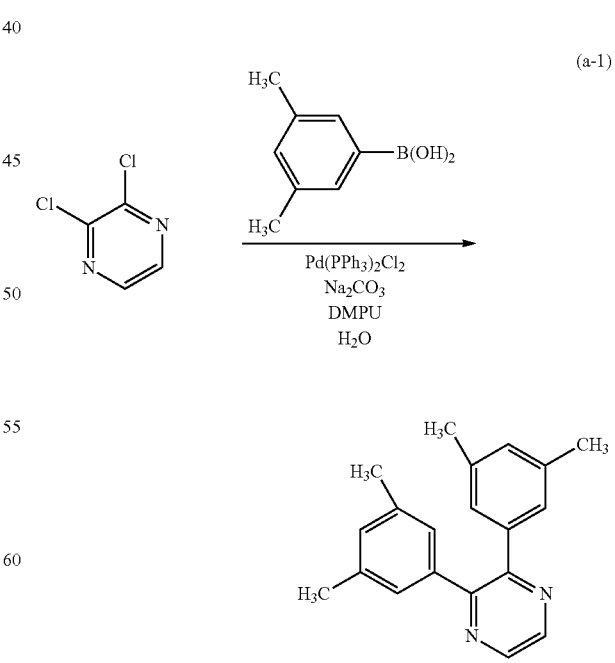

(a-1)

Hdmdppr

Step 2: Synthesis of 2,3-Bis(3,5-dimethylphenyl)-5-phenylpyrazine (abbreviation: Hdmdppr-P)

First, 4.28 g of Hdmdppr (abbreviation) obtained in Step 1 and 80 mL of dry THF were put into a three-neck flask and the air in the flask was replaced with nitrogen. After the flask was cooled with ice, 9.5 mL of phenyl lithium (1.9M solution of phenyl lithium in butyl ether) was added dropwise, and the mixture was stirred at room temperature for 23.5 hours. The reacted solution was poured into water and the solution was subjected to extraction with chloroform. The obtained organic layer was washed with water and a saturated aqueous solution of sodium chloride, and dried with magnesium sulfate. Manganese oxide was added to the obtained mixture and the mixture was stirred for 30 minutes. Then, the solution was filtered and the solvent was distilled off. The obtained residue was purified by silica gel column chromatography using dichloromethane as a developing solvent, so that Hdmdppr-P (abbreviation), which was the pyrazine derivative to be produced, was obtained as an orange oil in a yield of 26%. A synthesis scheme of Step 2 is shown in (a-2).

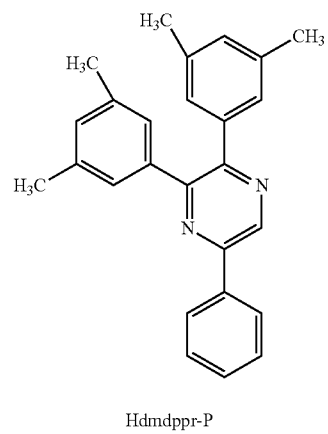

Hdmdppr-P

Step 3: Synthesis of Di-μ-chloro-tetrakis{4,6-dimethyl-2-[3-(3,5-dimethylphenyl)-5-phenyl-2-pyrazinyl-κN]phenyl-κC}diiridium(III) (abbreviation: [Ir(dmdppr-P)$_2$Cl]$_2$)

Next, into a recovery flask equipped with a reflux pipe were put 15 mL of 2-ethoxyethanol, 5 mL of water, 1.40 g of Hdmdppr-P (abbreviation) obtained in Step 2, and 0.51 g of iridium chloride hydrate (IrCl$_3$.H$_2$O) (produced by Sigma-Aldrich Corporation), and the air in the flask was replaced with argon. After that, irradiation with microwaves (2.45 GHz, 100 W) was performed for 1 hour to cause a reaction. The solvent was distilled off, and then the obtained residue was suction-filtered and washed with ethanol to give [Ir(dmdppr-P)$_2$Cl]$_2$ (abbreviation) that is a dinuclear complex as a reddish brown powder in a yield of 58%. A synthesis scheme of Step 3 is shown in (a-3).

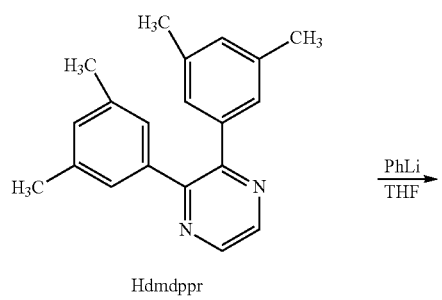

(a-2)

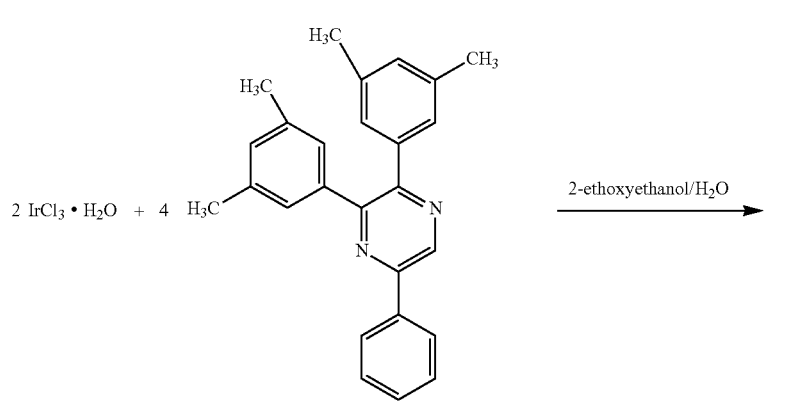

(a-3)

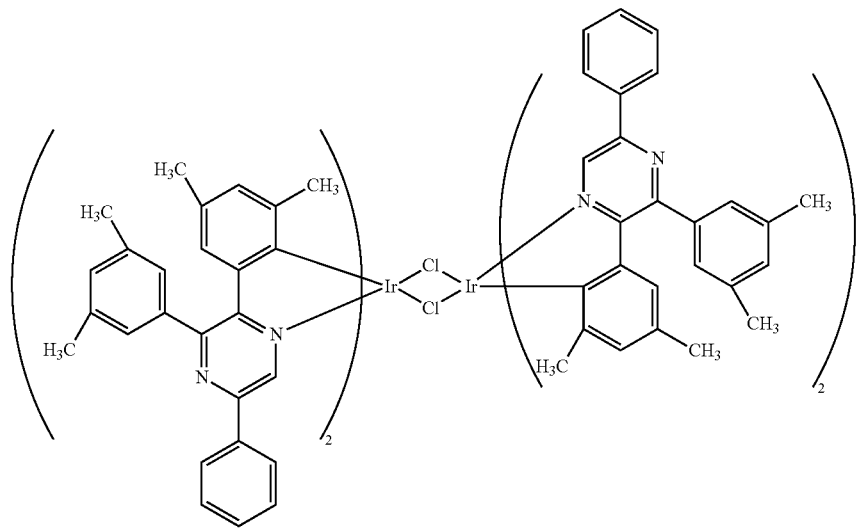

[Ir(dmdppr-P)₂Cl]₂

Step 4: Synthesis of Bis{4,6-dimethyl-2-[3-(3,5-dimethylphenyl)-5-phenyl-2-pyrazinyl-κN]phenyl-κC}(2,6-dimethyl-3,5-heptanedionato-κ²O,O')iridium(III) (abbreviation: [Ir(dmdppr-P)₂(dibm)])

Further, into a recovery flask equipped with a reflux pipe were put 30 mL of 2-ethoxyethanol, 0.94 g of [Ir(dmdppr-P)₂Cl]₂ that is the dinuclear complex obtained in Step 3, 0.23 g of diisobutyrylmethane (abbreviation: Hdibm), and 0.52 g of sodium carbonate, and the air in the flask was replaced with argon. After that, the mixture was heated by irradiation with microwaves (2.45 GHz, 120 W) for 60 minutes. The solvent was distilled off, and the obtained residue was suction-filtered with ethanol. The obtained solid was washed with water and ethanol and recrystallization was carried out with a mixed solvent of dichloromethane and ethanol, so that [Ir(dmdppr-P)₂(dibm)] (abbreviation), the organometallic complex in one embodiment of the present invention, was obtained as a dark red powder in a yield of 75%. A synthesis scheme of Step 4 is shown in (a-4).

(a-4)

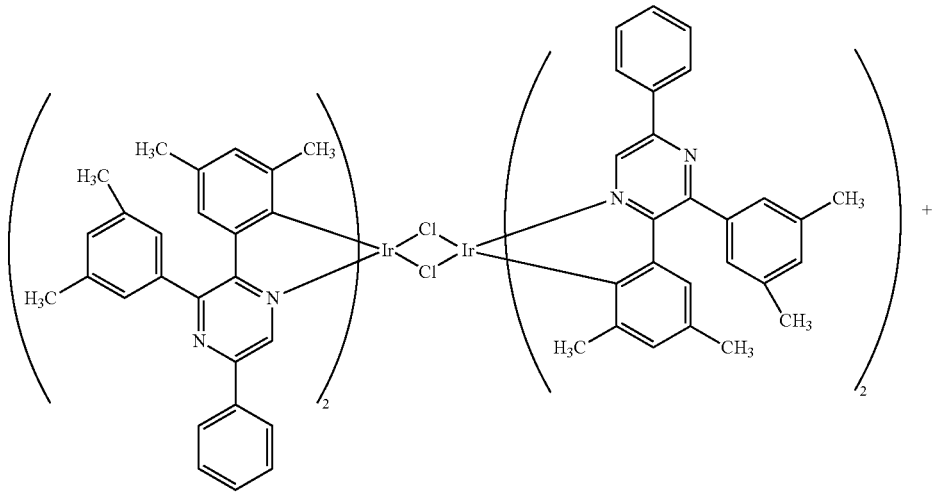

[Ir(dmdppr-P)₂Cl]₂

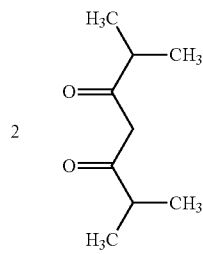
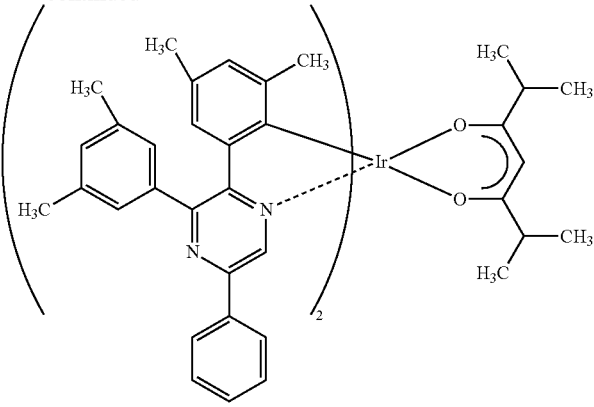

[Ir(dmdppr-P)₂(dibm)]

An analysis result by nuclear magnetic resonance (¹H-NMR) spectroscopy of the dark red powder obtained by the above-described synthesis method is described below. These results revealed that the organometallic complex [Ir(dmdppr-P)₂(dibm)] (abbreviation) was obtained in this synthesis example.

¹H-NMR. δ(CDCl₃): 0.79 (d, 6H), 0.96 (d, 6H), 1.41 (s, 6H), 1.96 (s, 6H), 2.24-2.28 (m, 2H), 2.41 (s, 12H), 5.08 (s, 1H), 6.46 (s, 2H), 6.82 (s, 2H), 7.18 (s, 2H), 7.39-7.50 (m, 10H), 8.03 (d, 4H), 8.76 (s, 2H).

EXPLANATION OF REFERENCE

101: anode, 102: cathode, 103: EL layer, 104: hole-injection layer, 105: hole-transport layer, 106: light-emitting layer, 106a: first light-emitting layer, 106b: second light-emitting layer, 107: electron-transport layer, 108: electron-injection layer, 109a: first phosphorescent compound, 109b: second phosphorescent compound, 110: first organic compound, 111: second organic compound, 201: first electrode (anode), 202: second electrode (cathode), 203: EL layer, 204: hole-injection layer, 205: hole-transport layer, 206: light-emitting layer, 206a: first light-emitting layer, 206b: second light-emitting layer, 207: electron-transport layer, 208: electron-injection layer, 209a: first phosphorescent compound, 209b: second phosphorescent compound, 210: first organic compound, 211: second organic compound, 301: first electrode, 302(1): first EL layer, 302(2): second EL layer, 304: second electrode, 305: charge generation layer (I), 305(1): first charge generation layer (I), 305(2): second charge generation layer (II), 401: reflective electrode, 402: semi-transmissive and semi-reflective electrode, 403a: first transparent conductive layer, 403b: second transparent conductive layer, 404B: first light-emitting layer (B), 404G: second light-emitting layer (G), 404R: third light-emitting layer (R), 405: EL layer, 410R: first light-emitting element (R), 410G: second light-emitting element (G), 410B: third light-emitting element (B), 501: element substrate, 502: pixel portion, 503: driver circuit portion (source line driver circuit), 504a, 504b: driver circuit portion (gate line driver circuit), 505: sealant, 506: sealing substrate, 507: lead wiring, 508: flexible printed circuit (FPC), 509: n-channel TFT, 510: p-channel TFT, 511: switching TFT, 512: current control TFT, 513: first electrode (anode), 514: insulator, 515: EL layer, 516: second electrode (cathode), 517: light-emitting element, 518: space, 1100: substrate, 1101: first electrode, 1102: EL layer, 1103: second electrode, 1111: hole-injection layer, 1112: hole-transport layer, 1113: light-emitting layer, 1114: electron-transport layer, 1115: electron-injection layer, 3000: substrate, 3001: first electrode, 3002a: first EL layer, 3002b: second EL layer, 3011a: first hole-injection layer, 3011b: second hole-injection layer, 3012a: first hole-transport layer, 3012b: second hole-transport layer, 3013a: light-emitting layer (A), 3013b: light-emitting layer (B), 3013(b1): first light-emitting layer, 3013(b2): second light-emitting layer, 3014a: first electron-transport layer, 3014b: second electron-transport layer, 3015a: first electron-injection layer, 3015b: second electron-injection layer, 3003: second electrode, 3004: charge generation layer, 4000, 4000', 4000'': substrate, 4001, 4001', 4001'': first electrode, 4002a: first EL layer, 4002b: second EL layer, 4003, 4003', 4003'': second electrode, 4004, 4004', 4004'': charge generation layer, 4011a, 4011a', 4011a'': first hole-injection layer, 4011b, 4011b', 4011b'': second hole-injection layer, 4012a, 4012a', 4012a'': first hole-transport layer, 4012b, 4012b', 4012b'': second hole-transport layer, 4013a, 4013a', 4013a'': light-emitting layer (A), 4013b, 4013b', 4013b'': light-emitting layer (B), 4013(b1), 4013(b1)', 4013(b1)'': first light-emitting layer, 4013(b2), 4013(b2)', 4013(b2)'': second light-emitting layer, 4014a, 4014a', 4014a'': first electron-transport layer, 4014b, 4014b', 4014b'': second electron-transport layer, 4015a, 4015a', 4015a'': first electron-injection layer, 4015b, 4015b', 4015b'': second electron-injection layer, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7312: microphone, 7400: cellular phone, 7401: housing, 7402: display portion, 7403: operation button, 7404: external connection port, 7405: speaker, 7406: microphone, 8001: lighting device, 8002: lighting device, 8003: lighting device, 8004: lighting device, 9033: clasp, 9034: display mode switch, 9035: power switch, 9036: power saver switch, 9038:

operation switch, 9630: housing, 9631: display portion, 9631a: display portion, 9631b: display portion, 9632a: touch panel region, 9632b: touch panel region, 9633: solar cell, 9634: charge and discharge control circuit, 9635: battery, 9636: DCDC converter, 9637: operation key, 9638: converter, and 9639: button.

This application is based on Japanese Patent Application serial no. 2012-087050 filed with Japan Patent Office on Apr. 6, 2012, the entire contents of which are hereby incorporated by reference.

The invention claimed is:

1. A light-emitting device comprising:
a first electroluminescent layer over an anode, and a second electroluminescent layer over the first electroluminescent layer, at least one of the first electroluminescent layer and the second electroluminescent layer comprising a first light-emitting layer and a second light-emitting layer over the first light-emitting layer; and
a charge generation layer between the first electroluminescent layer and the second electroluminescent layer, the charge generation layer being configured to inject electrons into the first electroluminescent layer and inject holes into the second electroluminescent layer,
a cathode over the second electroluminescent layer,
wherein the first light-emitting layer comprises a first phosphorescent compound, a first organic compound having an electron-transport property, and a second organic compound having a hole-transport property,
wherein the second light-emitting layer comprises a second phosphorescent compound and the first organic compound,
wherein the first phosphorescent compound is not the same compound as the second phosphorescent compound, and
wherein an emission spectrum of an exciplex of the first organic compound and the second organic compound overlaps with an absorption spectrum of the first phosphorescent compound.

2. The light-emitting device according to claim 1, wherein light emitted from the first light-emitting layer has a shorter wavelength than light emitted from the second light-emitting layer.

3. The light-emitting device according to claim 1, wherein a peak of the emission spectrum of the exciplex has a longer wavelength than a peak of the absorption spectrum of the first phosphorescent compound.

4. The light-emitting device according to claim 1, wherein a peak of the emission spectrum of the exciplex has a longer wavelength than a peak of an emission spectrum of each of the first organic compound and the second organic compound.

5. The light-emitting device according to claim 1, wherein at least one of the first phosphorescent compound and the second phosphorescent compound is an organometallic complex.

6. The light-emitting device according to claim 1, wherein the first organic compound is a π-electron deficient heteroaromatic compound.

7. The light-emitting device according to claim 1, wherein the second organic compound is a π-electron rich heteroaromatic compound or an aromatic amine compound.

8. The light-emitting device according to claim 1, wherein the light-emitting device is incorporated in an electronic device.

9. The light-emitting device according to claim 1, wherein the light-emitting device is incorporated in a lighting device.

10. A light-emitting device comprising:
a first electroluminescent layer comprising a first light-emitting layer over an anode;
a charge generation layer over the first electroluminescent layer;
a second electroluminescent layer over the charge generation layer;
a cathode over the second electroluminescent layer,
wherein the charge generation layer is configured to inject electrons into the first electroluminescent layer and inject holes into the second electroluminescent layer,
wherein the second electroluminescent layer comprises a second light-emitting layer and a third light-emitting layer over the second light-emitting layer,
wherein the second light-emitting layer comprises a first phosphorescent compound, a first organic compound having an electron-transport property, and a second organic compound having a hole-transport property,
wherein the third light-emitting layer comprises a second phosphorescent compound and the first organic compound,
wherein the first phosphorescent compound is not the same compound as the second phosphorescent compound, and
wherein an emission spectrum of an exciplex of the first organic compound and the second organic compound overlaps with an absorption spectrum of the first phosphorescent compound.

11. The light-emitting device according to claim 10, wherein light emitted from the second light-emitting layer has a shorter wavelength than light emitted from the third light-emitting layer.

12. The light-emitting device according to claim 10, wherein a peak of the emission spectrum of the exciplex has a longer wavelength than a peak of the absorption spectrum of the first phosphorescent compound.

13. The light-emitting device according to claim 10, wherein a peak of the emission spectrum of the exciplex has a longer wavelength than a peak of an emission spectrum of each of the first organic compound and the second organic compound.

14. The light-emitting device according to claim 10, wherein at least one of the first phosphorescent compound and the second phosphorescent compound is an organometallic complex.

15. The light-emitting device according to claim 10, wherein the first organic compound is a π-electron deficient heteroaromatic compound.

16. The light-emitting device according to claim 10, wherein the second organic compound is a π-electron rich heteroaromatic compound or an aromatic amine compound.

17. The light-emitting device according to claim 10, wherein a material of the first light-emitting layer is different from a material of the second light-emitting layer and a material of the third light-emitting layer.

18. The light-emitting device according to claim 10, wherein the light-emitting device is incorporated in an electronic device.

19. The light-emitting device according to claim 10, wherein the light-emitting device is incorporated in a lighting device.

* * * * *